US008980278B2

(12) United States Patent
Steinberg et al.

(10) Patent No.: US 8,980,278 B2
(45) Date of Patent: Mar. 17, 2015

(54) BIO-FUNCTIONALIZED STIMULUS-RESPONSIVE DISSOLVABLE PEG-HYDROGELS

(75) Inventors: Thorsten Steinberg, Mannheim (DE); Wilfried Weber, Freiburg (DE); Raphael Guebeli, Buetschwil (CH); Pascal Tomakidi, Freiburg (DE); Dougal Laird, Freiburg (DE)

(73) Assignees: Universitaetsklinikum Freiburg, Freiburg (DE); Albert-Ludwigs-Universitaet Freigburg, Freiburg (DE)

( * ) Notice: Subject to any disclaimer, the term of this patent is extended or adjusted under 35 U.S.C. 154(b) by 0 days.

(21) Appl. No.: 13/988,252

(22) PCT Filed: Nov. 18, 2011

(86) PCT No.: PCT/EP2011/005820
§ 371 (c)(1),
(2), (4) Date: Jul. 23, 2013

(87) PCT Pub. No.: WO2012/065751
PCT Pub. Date: May 24, 2012

(65) Prior Publication Data
US 2013/0315996 A1    Nov. 28, 2013

(30) Foreign Application Priority Data

Nov. 19, 2010 (EP) ..................... 10014788

(51) Int. Cl.
| | | |
|---|---|---|
| *A61K 6/00* | (2006.01) | |
| *A61K 38/00* | (2006.01) | |
| *C08L 101/02* | (2006.01) | |
| *A61K 47/48* | (2006.01) | |
| *A61K 47/10* | (2006.01) | |
| *A61K 38/16* | (2006.01) | |
| *A61K 38/18* | (2006.01) | |
| *A61K 9/00* | (2006.01) | |
| *A61K 9/06* | (2006.01) | |

(52) U.S. Cl.
CPC ........... *A61K 47/48215* (2013.01); *A61K 47/10* (2013.01); *A61K 47/48784* (2013.01); *A61K 38/16* (2013.01); *A61K 38/18* (2013.01); *A61K 9/0014* (2013.01); *A61K 9/0043* (2013.01); *A61K 9/0046* (2013.01); *A61K 9/0048* (2013.01); *A61K 9/006* (2013.01); *A61K 9/0063* (2013.01); *A61K 9/0085* (2013.01); *A61K 9/06* (2013.01); *C07K 2319/20* (2013.01); *C07K 2319/30* (2013.01); *C07K 2319/33* (2013.01); *Y10S 514/801* (2013.01)
USPC ...... 424/197.11; 424/423; 424/486; 424/443; 424/484; 623/1.38; 623/1.42; 514/772.3; 514/773; 514/801

(58) Field of Classification Search
CPC ......... A61K 6/00; A61K 9/00; A61K 9/0024; A61K 9/10; A61K 9/70; A61K 38/00; A61K 47/00; C08L 101/00; C08L 101/02; C08L 101/12; A61B 2017/00898; A61B 2017/00831; A61L 24/00; A61L 24/0031; A61L 24/0047; A61L 24/04; A61L 2430/00
USPC .............. 424/423, 486, 443, 499, 197.1, 484; 623/1.38, 1.42; 514/772.3, 773, 801
See application file for complete search history.

(56) References Cited

U.S. PATENT DOCUMENTS 7,112,668 B2 *    9/2006    Rastelli et al. ............... 536/23.5

FOREIGN PATENT DOCUMENTS

| WO | WO 2009/146929 A1 | 12/2009 |
| WO | WO 2009146929 A1 * | 12/2009 |

OTHER PUBLICATIONS

Greenspan et al. 1999 (Defining epitopes: It's not as easy as it seems; Nature Biotechnology, 17:936-937).*
Shpigel et al. 2000 (Expression, purification, and applications of staphylococcal protein A to cellulose-binding domain; Biotechnol. Appl. Biochem. 31:197-203).*
Ito et al. 2010 (Reversible hydrogel formation driven by protein-peptide-specific interaction and chondrocyte entrapment; Biomaterials 31:58-66).*
Brockelbank et al. 2006 (Recombinant *Escherichia coli* Strain Produces a ZZ Domain Displaying Granules Suitable for Immunoglobulin G Purification; Applied and Environmental Microbiology, 72(11):7394-7397).*

(Continued)

*Primary Examiner* — J. Hines
*Assistant Examiner* — Mary Lyons
(74) *Attorney, Agent, or Firm* — Squire Patton Boggs (US) LLP

(57) ABSTRACT

The present invention is directed to a bio-functionalized stimulus-responsive dissolvable PEG-hydrogel. This inventive stimulus-responsive dissolvable PEG-hydrogel comprises a matrix of PEG-polymers, which are modified to contain at least one multifunctional fusion protein, the multifunctional fusion protein preferably comprising as components a substrate binding peptide (SBP), preferably a repetitive RGD-binding peptide and/or a ZZ-binding domain, preferably a tag for purification, and at least one N- and/or C-terminal linker. The present invention is furthermore directed to the use of such inventive stimulus-responsive dissolvable PEG-hydrogels in the treatment of lesions, in surgical dressings, for wound treating, for soft and hard tissue regeneration, for the treatment of wounds in the oral cavity, in the field of ophthalmology, in the field of periodontal defects, etc. The invention also describes a method of treatment for such diseases. Additionally, the present invention provides a kit comprising the inventive stimulus-responsive dissolvable PEG-hydrogel and optionally further components.

12 Claims, 32 Drawing Sheets

(56) References Cited

OTHER PUBLICATIONS

Figure 1:
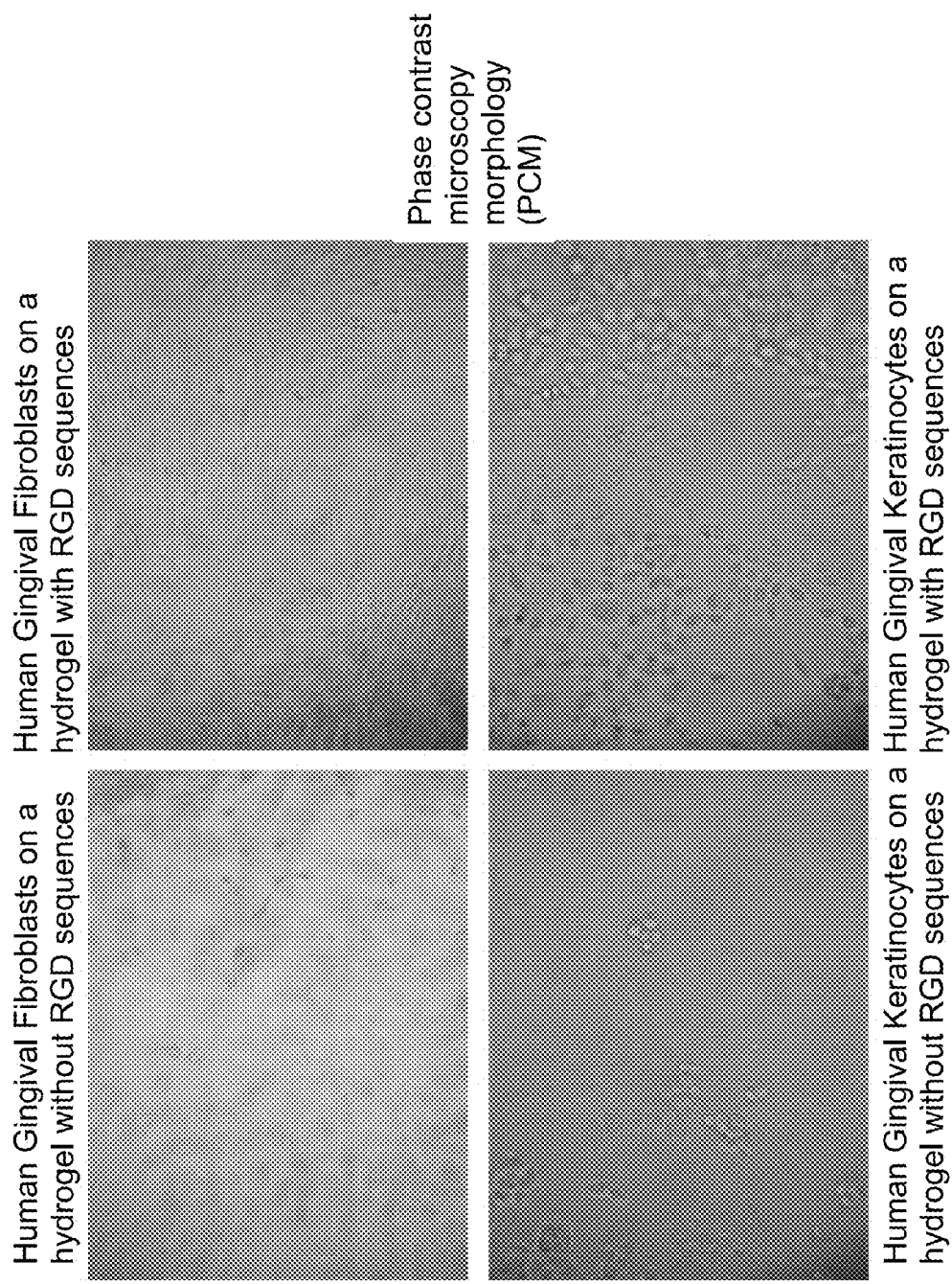

Wikman 2005 (Rational and combinatorial protein engineering for vaccine delivery and drug targeting; School of Biotechnology, Royal Institute of Technology, Stockholm, Sweden; 2005; ISBN 91-7178-003-03; 102 pp.).*

Lowenadler et al. 1987 (A gene fusion system for generating antibodies against short peptides; GENE 58: 87-97).*

International Search Report and Written Opinion dated Feb. 2, 2012 corresponding to International Patent Application No. PCT/EP2011/005820.

Fuyu Ito et al., "Reversible hydrogel formation driven by protein-peptide-specific interaction and chondrocyte entrapment," Biomaterials 2010, ElSevier, vol. 31, No. 1, Jan. 2010, pp. 58-66, XP002628885.

Pilar Valderrama et al., "Evaluation of Parathyroid Hormone Bound to a Synthetic Matrix for Guided Bone Regeneration Around Dental Implants: A Histomorphomertric Study in Dogs," Journal of Periodontology, vol. 81, No. 5, May 2010, pp. 737-747, XP008134407.

Matthias P. Lutolf et al., "Repair of Bone Defects Using Synthetic Mimetrics of Collagenous Extracellular Matrices," Nature Biotechnology, Nature Publishing Group, vol. 21, No. 5, May 1, 2003, pp. 513-518, XP002508395.

* cited by examiner

GyrB

Nucleotide sequence:
ATGTCGAATTCTTATGACTCCTCCAGTATCAAAGTCCTGAAAGGGCTGGA
TGCGGTGCGTAAGCGCCCGGGTATGTATATCGGCGACACGGATGACGGCA
CCGGTCTGCACCACATGGTATTCGAGGTGGTAGATAACGCTATCGACGAA
GCGCTCGCGGGTCACTGTAAAGAATTATCGTCACCATTCACGCCGATAA
CTCTGTCTCTGTACAGGATGACGGGCGCGGCATTCCGACCGGTATTCACC
CGGAAGAGGGCGTATCGGCGGCGGAAGTGATCATGACCGTTCTGCACGCA
GGCGGTAAATTTGACGATAACTCCTATAAAGTGTCCGGCGGTCTGCACGG
CGTTGGTGTTTCGGTAGTAAACGCCCTGTCGCAAAAACTGGAGCTGGTTA
TCCAGCGCGAGGGTAAAATTCACCGTCAGATCTACGAACACGGTGTACCG
CAGGCCCCGCTGGCGGTTACCGGCGAGACTGAAAAAACCGGCACCATGGT
GCGTTTCTGGCCCAGCCTCGAAACCTTCACCAATGTGACCGAGTTCGAAT
ATGAAATTCTGGCGAAACGTCTGCGTGAGTTGTCGTTCCTCAACTCCGGC
GTTTCCATTCGTCTGCGCGACAAGCGCGACGGCAAAGAAGACCACTTCCA
CTATGAAGGC Protein sequence:
MSNSYDSSSIKVLKGLDAVRKRPGMYIGDTDDGTGLHHMVFEVVDNAIDEALA
GHCKEIIVTIHADNSVSVQDDGRGIPTGIHPEEGVSAAEVIMTVLHAGGKFDD
NSYKVSGGLHGVGVSVVNALSQKLELVIQREGKIHRQIYEHGVPQAPLAVTGE
TEKTGTMVRFWPSLETFTNVTEFEYEILAKRLRELSFLNSGVSIRLRDKRDGK
EDHFHYEG

Figure 5 pRG107

Nucleotide sequence:

ATGTGCTCGAATTCTTATGACTCCTCCAGTATCAAAGTCCTGAAAGGGCT
GGATGCGGTGCGTAAGCGCCCGGGTATGTATATCGGCGACACGGATGACG
GCACCGGTCTGCACCACATGGTATTCGAGGTGGTAGATAACGCTATCGAC
GAAGCGCTCGCGGGTCACTGTAAAGAATTATCGTCACCATTCACGCCGA
TAACTCTGTCTCTGTACAGGATGACGGGCGCGGCATTCCGACCGGTATTC
ACCCGGAAGAGGGCGTATCGGCGGCGGAAGTGATCATGACCGTTCTGCAC
GCAGGCGGTAAATTTGACGATAACTCCTATAAAGTGTCCGGCGGTCTGCA
CGGCGTTGGTGTTTCGGTAGTAAACGCCCTGTCGCAAAAACTGGAGCTGG
TTATCCAGCGCGAGGGTAAAATTCACCGTCAGATCTACGAACACGGTGTA
CCGCAGGCCCCGCTGGCGGTTACCGGCGAGACTGAAAAAACCGGCACCAT
GGTGCGTTTCTGGCCCAGCCTCGAAACCTTCACCAATGTGACCGAGTTCG
AATATGAAATTCTGGCGAAACGTCTGCGTGAGTTGTCGTTCCTCAACTCC
GGCGTTTCCATTCGTCTGCGCGACAAGCGCGACGGCAAAGAAGACCACTT
CCACTATGAAGGCGGCCGTGGCGATAGCCCTGGTCGTGGTGACTCTCCAC
ATCATCACCATCACCATTGCTGA

Figure 6 pRG107

```
Protein sequence:
MCSNSYDSSSIKVLKGLDAVRKRPGMYIGDTDDGTGLHHMVFEVVDNAIDEAL
AGHCKEIIVTIHADNSVSVQDDGRGIPTGIHPEEGVSAAEVIMTVLHAGGKFD
DNSYKVSGGLHGVGVSVVNALSQKLELVIQREGKIHRQIYEHGVPQAPLAVTG
ETEKTGTMVRFWPSLETFTNVTEFEYEILAKRLRELSFLNSGVSIRLRDKRDG
KEDHFHYEGGRGDSPGRGDSPHHHHHHC Subunits:
AA1: Methionine start
AA2: cysteine 1 for coupling to the PEG-VS
AA3-221: GyrB(1-220)
AA222-233: double-GRGDSP-motif
AA234-239: hexahistidine tag
AA240: cysteine 2 for coupling to the PEG-VS
```

Figure 6 (cont.)

pRG111
nucleotide sequence:

ATGGCGCAACACGATGAAGCCGTAGACAACAAATTCAACAAAGAACAACA
AAACGCGTTCTATGAGATCTTACATTTACCTAACTTAAACGAAGAACAAC
GAAACGCCTTCATCCAAAGTTTAAAAGATGACCCAAGCCAAAGCGCTAAC
CTTTTAGCAGAAGCTAAAAAGCTAAATGATGCTCAGGCGCCGAAAGTAGA
CAACAAATTCAACAAAGAACAACAAAACGCGTTCTATGAGATCTTACATT
TACCTAACTTAAACGAAGAACAACGAAACGCCTTCATCCAAAGTTTAAAA
GATGACCCAAGCCAAAGCGCTAACCTTTTAGCAGAAGCTAAAAAGCTAAA
TGATGCTCAGGCGCCGAAAGTAGACGCGAATTCGAGCATGTCGAATTCTT
ATGACTCCTCCAGTATCAAAGTCCTGAAAGGGCTGGATGCGGTGCGTAAG
CGCCCGGGTATGTATATCGGCGACACGGATGACGGCACCGGTCTGCACCA
CATGGTATTCGAGGTGGTAGATAACGCTATCGACGAAGCGCTCGCGGGTC
ACTGTAAAGAAATTATCGTCACCATTCACGCCGATAACTCTGTCTCTGTA
CAGGATGACGGGCGCGGCATTCCGACCGGTATTCACCCGGAAGAGGGCGT
ATCGGCGGCGGAAGTGATCATGACCGTTCTGCACGCAGGCGGTAAATTTG
ACGATAACTCCTATAAAGTGTCCGGCGGTCTGCACGGCGTTGGTGTTTCG
GTAGTAAACGCCCTGTCGCAAAAACTGGAGCTGGTTATCCAGCGCGAGGG
TAAAATTCACCGTCAGATCTACGAACACGGTGTACCGCAGGCCCCGCTGG
CGGTTACCGGCGAGACTGAAAAAACCGGCACCATGGTGCGTTTCTGGCCC
AGCCTCGAAACCTTCACCAATGTGACCGAGTTCGAATATGAAATTCTGGC
GAAACGTCTGCGTGAGTTGTCGTTCCTCAACTCCGGCGTTTCCATTCGTC
TGCGCGACAAGCGCGACGGCAAAGAAGACCACTTCCACTATGAAGGCCAT
CATCACCATCACCATTGCTGA

Figure 7 pRG111 protein sequence:

MAQHDEAVDNKFNKEQQNAFYEILHLPNLNEEQRNAFIQSLKDDPSQSANLLA
EAKKLNDAQAPKVDNKFNKEQQNAFYEILHLPNLNEEQRNAFIQSLKDDPSQS
ANLLAEAKKLNDAQAPKVDANSSMSNSYDSSSIKVLKGLDAVRKRPGMYIGDT
DDGTGLHHMVFEVVDNAIDEALAGHCKEIIVTIHADNSVSVQDDGRGIPTGIH
PEEGVSAAEVIMTVLHAGGKFDDNSYKVSGGLHGVGVSVVNALSQKLELVIQR
EGKIHRQIYEHGVPQAPLAVTGETEKTGTMVRFWPSLETFTNVTEFEYEILAK
RLRELSFLNSGVSIRLRDKRDGKEDHFHYEGHHHHHHC

Subunits:
AA1-129: ZZ-binding domain, derived from pEZZ-18 (commercial vector, GE healthcare)
AA130-349: GyrB(1-220)
AA350-355: hexahistidine tag
AA356: cysteine for coupling to the PEG-VS

Figure 7 (cont.)

pRG116 nucleotide sequence:
ATGTCGAATTCTTATGACTCCTCCAGTATCAAAGTCCTGAAAGGGCTGGA
TGCGGTGCGTAAGCGCCCGGGTATGTATATCGGCGACACGGATGACGGCA
CCGGTCTGCACCACATGGTATTCGAGGTGGTAGATAACGCTATCGACGAA
GCGCTCGCGGGTCACTGTAAAGAAATTATCGTCACCATTCACGCCGATAA
CTCTGTCTCTGTACAGGATGACGGGCGCGGCATTCCGACCGGTATTCACC
CGGAAGAGGGCGTATCGGCGGCGGAAGTGATCATGACCGTTCTGCACGCA
GGCGGTAAATTTGACGATAACTCCTATAAAGTGTCCGGCGGTCTGCACGG
CGTTGGTGTTTCGGTAGTAAACGCCCTGTCGCAAAAACTGGAGCTGGTTA
TCCAGCGCGAGGGTAAAATTCACCGTCAGATCTACGAACACGGTGTACCG
CAGGCCCCGCTGGCGGTTACCGGCGAGACTGAAAAAACCGGCACCATGGT
GCGTTTCTGGCCCAGCCTCGAAACCTTCACCAATGTGACCGAGTTCGAAT
ATGAAATTCTGGCGAAACGTCTGCGTGAGTTGTCGTTCCTCAACTCCGGC
GTTTCCATTCGTCTGCGCGACAAGCGCGACGGCAAAGAAGACCACTTCCA
CTATGAAGGCGGCCGTGGCGATAGCCCTGGTCGTGGTGACTCTCCACATC
ATCACCATCACCATTGCTGA protein sequence:
MSNSYDSSSIKVLKGLDAVRKRPGMYIGDTDDGTGLHHMVFEVVDNAIDEALA
GHCKEIIVTIHADNSVSVQDDGRGIPTGIHPEEGVSAAEVIMTVLHAGGKFDD
NSYKVSGGLHGVGVSVVNALSQKLELVIQREGKIHRQIYEHGVPQAPLAVTGE
TEKTGTMVRFWPSLETFTNVTEFEYEILAKRLRELSFLNSGVSIRLRDKRDGK
EDHFHYEGGRGDSPGRGDSPHHHHHC Subunits:
AA1-220: GyrB(1-220)
AA221-232: double-GRGDSP-motif
AA233-238: hexahistidine tag
AA239: cysteine 2 for coupling to the PEG-VS

Figure 8

FGF-7-Fc-His:

Nucleotide sequence:

ATGCACAAATGGATACTGACATGGATCCTGCCAACTTTGCTCTACAGATC
ATGCTTTCACATTATCTGTCTAGTGGGTACTATATCTTTAGCTTGCAATG
ACATGACTCCAGAGCAAATGGCTACAAATGTGAACTGTTCCAGCCCTGAG
CGACACACAAGAAGTTATGATTACATGGAAGGAGAGGATATAAGAGTGAG
AAGACTCTTCTGTCGAACACAGTGGTACCTGAGGATCGATAAAAGAGGCA
AAGTAAAAGGGACCCAAGAGATGAAGAATAATTACAGTAAGGGTAACTAT
AACGGTCCTAAGGTAGCGAGTGGTGGAGGCGGTTCAGGCGGAGGTGGCTC
TGGCGGTGGCGGATCGCCCAGAGGGCCCACAATCAAGCCCTGTCCTCCAT
GCAAATGCCCAGCACCTAACCTCGAGGGTGGACCATCCGTCTTCATCTTC
CCTCCAAAGATCAAGGATGTACTCATGATCTCCCTGAGCCCCATAGTCAC
ATGTGTGGTGGTGGATGTGAGCGAGGATGACCCAGATGTCCAGATCAGCT
GGTTTGTGAACAACGTGGAAGTACACACAGCTCAGACACAAACCCATAGA
GAGGATTACAACAGTACTCTCCGGGTGGTCAGTGCCCTCCCCATCCAGCA
CCAGGACTGGATGAGTGGCAAGGCGTTCGCATGCGCGGTCAACAACAAAG
ACCTCCCAGCGCCCATCGAGAGAACCATCTCAAAACCCAAAGGGTCAGTA
AGAGCTCCACAGGTATATGTCTTGCCTCCACCAGAAGAAGAGATGACTAA
GAAACAGGTCACTCTGACCTGCATGGTCACAGACTTCATGCCTGAAGACA
TTTACGTGGAGTGGACCAACAACGGGAAAACAGAGCTAAACTACAAGAAC
ACTGAACCAGTCCTGGACTCTGATGGTTCTTACTTCATGTACAGCAAGCT
GAGAGTGGAAAAGAAGAACTGGGTGGAAAGAAATAGCTACTCCTGTTCAG
TGGTCCACGAGGGTCTGCACAATCACCACACGACTAAGAGCTTCTCCCGG
ACTCCGGGTAAACACCATCACCATCACCATTGA

Figure 9

FGF-7-Fc-His:

Protein sequence:

MHKWILTWILPTLLYRSCFHIICLVGTISLACNDMTPEQMATNVNCSSPERHT
RSYDYMEGEDIRVRRLFCRTQWYLRIDKRGKVKGTQEMKNNYSKGNYNGPKVA
SGGGGSGGGGSGGGGSPRGPTIKPCPPCKCPAPNLEGGPSVFIFPPKIKDVLM
ISLSPIVTCVVVDVSEDDPDVQISWFVNNVEVHTAQTQTHREDYNSTLRVVSA
LPIQHQDWMSGKAFACAVNNKDLPAPIERTISKPKGSVRAPQVYVLPPPEEEM
TKKQVTLTCMVTDFMPEDIYVEWTNNGKTELNYKNTEPVLDSDGSYFMYSKLR
VEKKNWVERNSYSCSVVHEGLHNHHTTKSFSRTPGKHHHHHH

Subunits:
AA1-106: FGF-7 (=KGF)
AA107-122: serine-glycine linker
AA123-354: Fc domain
AA355-360: hexahistidine tag

Figure 9 (cont.)

```
gacgtgtaccacgacggcgcctgccccgaagtgaagcccgtggacaactt
cgactggtcccagtaccacggcaagtggtgggaggtggccaagtacccca
gccccaacggcaagtatggcaagtgcggctggattgagtacaccccgag
ggcaagagcgtgaaggtgtccagatacgacgtgatccacggcaagaata
cttcatggaaggcaccgcctaccccgtgggcgacagcaagatcggcaaga
tctaccacagccggaccgtgggcggctacaccaagaagaccgtgttcaac
gtgctgtccaccgacaacaagaactacatcatcggctaccgctgccgcta
cgacgaggacaagaagggccactgggaccacgtgtgggtgctgtcccggt
ccatggtgctgaccggcgaggccaagaccgccgtggagaactacctgatc
ggcagccccgtggtggacagccagaaactggtgtacagcgacttcagcga
ggccgcctgcaaagtgaacaac
```

```
MDVYHDGACPEVKPVDNFDWSQYHGKWWEVAKYPSPNGKYGKCGWIEYTP
EGKSVKVSRYDVIHGKEYFMEGTAYPVGDSKIGKIYHSRTVGGYTKKTVF
NVLSTDNKNYIIGYRCRYDEDKKGHWDHVWVLSRSMVLTGEAKTAVENYL
IGSPVVDSQKLVYSDFSEAACKVNN
```

Figure 18

```
Gacgtgtaccacgacggcgcctgccccgaagtgaagcccgtggacaactt
cgactggtcccagtaccacggcaagtggtggcaggtggccgcttatcccg
accacatcaccaagtacggcaagtgcggctgggccgagtacacccccgag
ggcaagagcgtgaaggtgtcccggtacagcgtgatccacggcaaagagta
cttcagcgagggcaccgcctacctgtgggcgacagcaagatcggcaaga
tctaccacagctacaccatcggcggcgtgacccaggagggcgtgttcaac
gtgctgtccaccgacaacaagaactacatcatcggctacttttgcagata
cgacgaggacaagaagggccacatggacttggtgtgggtgctgtcccggt
ccatggtgctgaccggcgaggccaagaccgccgtggagaactacctgatc
ggcagccccgtggtggacagccagaaactggtgtacagcgacttctccga
ggccgcctgcaaagtgaacaacagcaactggtcccaccccagttcgaaa
ag
```

MDVYHDGACPEVKPVDNFDWSQYHGKWWQVAAYPDHITKYGKCGWAEYTP
EGKSVKVSRYSVIHGKEYFSEGTAYPVGDSKIGKIYHSYTIGGVTQEGVF
NVLSTDNKNYIIGYFCSYDEDKKGHMDLVWVLSRSMVLTGEAKTAVENYL
IGSPVVDSQKLVYSDFSEAACKVNNSNWSHPQFEK

Figure 19 acgcggggaaagaaaagaaactaacaaggcataaaattcaaatgaaggaa
ggaaaacactttgttttagtacatggtgcatgccatggaggttggagttg
gtacaagctaaagccactgctagaagctgcaggccataaggttacagccc
ttgatttagcagcttctggcactgatttgagaaaaatagaggagcttcgc
acactttatgattatactttgccattgatggagttgatggaatctctttc
agcagatgagaaggttatattgtggggcatagtcttggtggtatgaatt
tgggacttgctatggaaaagtatccacaaaagatctatgctgctgttttc
ttggctgctttcatgcctgattctgttcacaactcctcctttgttttgga
acagtataatgagcggacgccagccgagaattggttggatactcagtttt
taccatatggttccctgaagagccactgacatccatgttttttggccca
aagttcttggctcacaagctctaccagctatgctctcctgaggatcttgc
attagcatcatcattggtgagaccaagctctttgtttatggaagacctat
cgaaggccaagtatttcacagatgaacggtttggatcagtgaagagagtt
tacattgtgtgcactgaggataaaggcataccagaagaattccagcgatg
gcaaattgacaacattggtgtcactgaagcaatagagattaaaggtgctg
atcacatggcaatgctatgcgagccccaaaaactttgcgcctctctcttg
gaaattgcccataaatacaactgatctctacattatgtcttcgtctcatg
tcaagattttcagtgcatgctgtaatttttttctattttcgaccggcgc
ataactgtctttgcctattttaaggattgcagtaatttcactcttctagt
gtggaaggcttccacataaggattgttctgtttctccattcaagtgtgtg
ttatgttagatacttaaaccgtatcaattcttgtaatgaaacttcttct
ttccttttgaaaaaaaaaaaaaaaaaa MKEGKHFVLVHGACHGGWSWYKLKPLLEAAGHKVTALDLAASGTDLRKIE
ELRTLYDYTLPLMELMESLSADEKVILVGHSLGGMNLGLAMEKYPQKIYA
AVFLAAFMPDSVHNSSFVLEQYNERTPAENWLDTQFLPYGSPEEPLTSMF
FGPKFLAHKLYQLCSPEDLALASSLVRPSSLFMEDLSKAKYFTDERFGSV
KRVYIVCTEDKGIPEEFQRWQIDNIGVTEAIEIKGADHMAMLCEPQKLCA
SLLEIAHKYN

Figure 20

```
acgcggggaaagaaaagaaactaacaaggcataaaattcaaatgaaggaa
ggaaaacactttgttttagtacatggtgcatgccatggaggttggagttg
gtacaagctaaagccactgctagaagctgcaggccataaggttacagccc
ttgatttagcagcttctggcactgatttgagaaaaatagaggagcttcgc
acactttatgattatactttgccattgatggagttgatggaagctctttc
agcagatgagaaggttatattagtggggcatagtcttggtggtatgaatt
tgggacttgctatggaaaagtatccacaaaagatctatgctgctgtttc
ttggctgctttcatgcctgattctgttcacaactcctcctttgttttgga
acagtataatgagcggacgccagccgagaattggttggatactcagtttt
taccatatggttccctgaagagccactgacatccatgttttttggccca
aagttcttggctcacaagctctaccagctatgctcctgaggatcttgc
attagcatcatcattggtgagaccaagctctttgtttatggaagacctat
cgaaggccaagtatttcacagatgaacggtttggatcagtgaagagagtt
tacattgtgtgcactgaggataaaggcataccagaagaattccagcgatg
gcaaattgacaacattggtgtcactgaagcaatagagattaaggtgctg
atcacatggcaatgctatgcgagccccaaaaactttgcgcctctcttg
gaaattgcccataaatacaactgatctctacattatgtcttcgtctcatg
tcaagattttcagtgcatgctgtaatttttttctattttttgaccggcgc
ataactgtctttgcctattttaaggattgcagtaatttcactcttctagt
gtggaaggcttccacataaggattgttctgtttctccattcaagtgtgtg
ttatgttgagatacttaaaccgtatcaattcttgtaatgaaacttcttct
ttccttttgaaaaaaaaaaaaaaaaaa
```

MKEGKHFVLVHGACHGGWSWYKLKPLLEAAGHKVTALDLAASGTDLRKIE
ELRTLYDYTLPLMELMESLSADEKVILVGHALGGMNLGLAMEKYPQKIYA
AVFLAAFMPDSVHNSSFVLEQYNERTPAENWLDTQFLPYGSPEEPLTSMF
FGPKFLAHKLYQLCSPEDLALASSLVRPSSLFMEDLSKAKYFTDERFGSV
KRVYIVCTEDKGIPEEFQRWQIDNIGVTEAIEIKGADHMAMLCEPQKLCA
SLLEIAHKYN

Figure 21

```
   1 ATGGATGAAT CTCTGGAGCA TCAAACTCAA ACACATGACC AAGAGAGCGA
  51 AATAGTTACT GAAGGAAGTG CCGTTGTGCA TAGTGAGCCA TCTCAAGAGG
 101 GTAATGTTCC TCCTAAAGTT GATAGTGAAG CTGAGGTCTT GGATGAGAAA
 151 GTCAGTAAGC AGATTATAAA GGAAGGTCAC GGTTCCAAAC CATCCAAGTA
 201 CTCTACATGC TTTTTGCACT ACAGGGCATG GACCAAAAAC TCGCAGCACA
 251 AATTTGAGGA TACATGGCAT GAGCAGCAAC CTATTGAATT GGTTCTTGGA
 301 AAAGAGAAAA AAGAACTAGC CGGTTTAGCC ATCGGTGTTG CTAGCATGAA
 351 GTCTGGTGAA CGTGCGCTTG TGCATGTTGG CTGGGAATTA GCTTATGGA
 401 AAGAAGGAAA CTTTTCTTTT CCGAATGTTC CACCTATGGC AGACTTGTTA
 451 TATGAGGTGG AAGTTATTGG GTTTGATGAA ACAAAGGAGG GAAAAGCTCG
 501 CAGTGATATG ACTGTAGAGG AAAGGATTGG TGCAGCAGAC AGAAGAAAAA
 551 TGGATGGAA TTCTCTTTTT AAGGAGGAGA ACTGGAGGA AGCCATGCAA
 601 CAGTATGAAA TGGCCATAGC ATACATGGGG GACGATTTTA TGTTTCAGCT
 651 GTATGGGAAG TACCAGGATA TGGCTTTAGC AGTTAAAAAC CCATGCCATC
 701 TTAACATAGC AGCTTGCCTC ATCAAACTAA ACGATACGA TGAAGCAATT
 751 GGTCACTGCA ACATTGTGTT GACAGAAGAA GAGAAAAACC CAAAAGCACT
 801 GTTCAGAAGA GGGAAAGCAA AGGCAGAGCT AGGACAGATG GACTCAGCAC
 851 GTGATGATTT CCGAAAGGCA CAAAAGTATG CTCCTGACGA CAAGGCGATT
 901 AGAAGAGAGC TACGAGCACT TGCAGAGCAA GAGAAAGCCT TGTACCAAAA
 951 GCAGAAAGAA ATGTACAAAG AATATTCAA AGGGAAAGAT GAAGGTGGTG
1001 CTAAGTCAAA GAGCCTTTTT TGGTTGATAG TGTTATGGCA ATGGTTTGTT
1051 TCCCTTTTCT CCCGTATCTT TCGACGCCAC AGAGTTAAAG CAGATTAA
```

```
   1 ATGGATGAAT CTCTGGAGCA TCAAACTCAA ACACATGACC AAGAGAGCGA
  51 AATAGTTACT GAAGGAAGTG CCGTTGTGCA TAGTGAGCCA TCTCAAGAGG
 101 GTAATGTTCC TCCTAAAGTT GATAGTGAAG CTGAGGTCTT GGATGAGAAA
 151 GTCAGTAAGC AGATTATAAA GGAAGGTCAC GGTTCCAAAC CATCCAAGTA
 201 CTCTACATGC TTTTTGCACT ACAGGGCATG GACCAAAAAC TCGCAGCACA
 251 AATTTGAGGA TACATGGCAT GAGCAGCAAC CTATTGAATT GGTTCTTGGA
 301 AAAGAGAAAA AAGAACTAGC CGGTTTAGCC ATCGGTGTTG CTAGCATGAA
 351 GTCTGGTGAA CGTGCGCTTG TGCATGTTGG CTGGGAATTA GCTTATGGA
 401 AAGAAGGAAA CTTTTCTTTT CCGAATGTTC CACCTATGGC AGACTTGTTA
 451 TATGAGGTGG AAGTTATTGG GTTTGATGAA ACAAAGGAGG TAA
```

MDESLEHQTQTHDQESEIVTEGSAVVHSEPSQEGNVPPKVDSEAEVLDEKVSKQIIKEGH
GSKPSKYSTCFLHYRAWTKNSQHKFEDTWHEQQPIELVLGKEKKELAGLAIGVASMKSGE
RALVHVGWELAYGKEGNFSFPNVPPMADLLYEVEVIGFDETKE

Figure 22

ATGCTCAGATCCGGTCTGGCTTCGTTAATCGTCGATGTCAATTTGCGGCGCACGTTACGTCC
ATCCCCAACCTTTTCTTTTCCGGCGCATCTTAGCCGTTGCATTATCACTTCCCGTTACTCCT
CCCGTACATCTCTAAGGTTTCCGATTCAAATATCTCGCCACCAACACCGTCTATCCTACTTT
TCTTCATCCTCTTCGTCGGAGCAAAGCAGACCAACTTCCTCTTCCCGAAACAGTTTCAGTGG
TCACGGTCAGCTTGATAGTGATGATAATTCTTCACCGCCTCCGTCGCAATCATCTTCCAAAG
TTCTTACATTGCCTACCGTATTAACACTTGGTCGTGTCGCCGCCGTCCCGCTTCTCGTCGCA
ACCTTTTACGTTGATAGTTGGTGGGAACAACTGCTACAACAAGCATTTTCATTGCAGCAGC
CATTACAGACTGGCTTGACGGCTATCTTGCCCGCAAGATGAGGTTAGGTTCTGCGTTTGGTG
CCTTTTTGGATCCAGTTGCTGATAAGCTTATGGTTGCAGCTACATTGATTTTACTGTGTACA
AAACCTATCCAAGTTGCTGAATTAGGACCACTTCCATGGTTATTGACCGTACCTTCTATTGC
AATCATTGGTAGGGAGATTACTATGTCCGCAGTAAGAGAATGGGCTGCATCTCAAAATGGAA
AGCTTTTAGAGGCAGTTGCTGTAAATAACTTGGGCAAGTGGAAAACCGCCACGCAGATGACA
GCACTAACCATACTTCTTGCAAGCCGAGATAGCAATGTTGGATGGCTCGTAGCTTCAGGTGC
TGGCTTGCTTTATGTATCAGCAGGACTATCTGTTTGGTCTTTAGCCGTTTATATGAGGAAGA
TATGGAAAGTACTAATGAAGTAG

MLRSGLASLIVDVNLRRTLRPSPTFSFPAHLSRCIITSRYSSRTSLRFPIQISRHQHRLS
YFSSSSSEQSRPTSSSRNSFSGHGQLDSDDNSSPPPSQSSSKVLTLPTVLTLGRVAAVP
LLVATFYVDSWWGTTATTSIFIAAAITDWLDGYLARKMRLGSAFGAFLDPVADKLMVAAT
LILLCTKPIQVAELGPLPWLLTVPSIAIIGREITMSAVREWAASQNGKLLEAVAVNNLGK
WKTATQMTALTILLASRDSNVGWLVASGAGLLYVSAGLSVWSLAVYMRKIWKVLMK

Figure 23

```
                                              cac tggctcctga
4921 tttcatcaaa ggtggtcaag ctatgcggtc tgttttcgaa cttcttgacc ggaaaaccga
4981 gattgaacct gatgatcctg ataccacccc ggtcccagac cggttacgtg gtgaagtcga
5041 gctcaaacat atcgatttct cttacccttc aaggccagac atccagattt tccgtgacct
5101 tagccttcgt gctagagctg gcaaaaccct agctcttgtg ggtccaagcg ggtgcggaaa
5161 aagctcagtt atctccctca tccagagatt ctacgaacct cctcaggcc gagtcatgat
5221 cgacgggaaa gacataagga aatacaacct gaaagccata aggaaacaca tagccatagt
5281 ccctcaagag ccgtgcttgt tcggaactac catttacgaa acattgcat atggacatga
5341 atgtgcgacc gaagcagaga tcatacaagc cgcgactcta gccagtgcgc acaaattcat
5401 atccgcgcta ccagaaggtt acaaaacgta tgttggcgag agaggcgttc agctctcggg
5461 aggacagaaa cagaggatcg cgatcgcacg tgccctcgtg aggaaagcag agatcatgct
5521 gcttgacgag gctacaagcg ctcttgatgc agagtccgag agatcagtcc aagaagcatt
5581 agaccaggct tgctctggta gaacatcaat agtcgtggct cataggctat ctacaatcag
5641 gaacgcacac gtgatcgctg tcatcgatga tggaaaagtg gctgaacaag gatcgcattc
5701 gcatcttctc aagaaccatc ctgatggaat ctacgcgcga atgatacagt tgcaaagatt
5761 tacgcataca caagtgattg gtatgacgtc aggttcaagt tctagggtta aggaagatga
5821 tgcttag 980                         tlapdfikgg qamrsvfell drkteiepdd pdttpvpdrl
1021 rgevelkhid fsypsrpdiq ifrdlslrar agktlalvgp sgcgkssvis liqrfyepss
1081 grvmidgkdi rkynlkairk hiaivpqepc lfgttiyeni ayghecatea eiiqaatlas
1141 ahkfisalpe gyktyvgerg vqlsggqkqr iaiaralvrk aeimlldeat saldaesers
1201 vqealdqacs grtsivvahr lstirnahvi aviddgkvae qgshshllkn hpdgiyarmi
1261 qlqrfthtqv igmtsgsssr vkedda
```

Figure 24

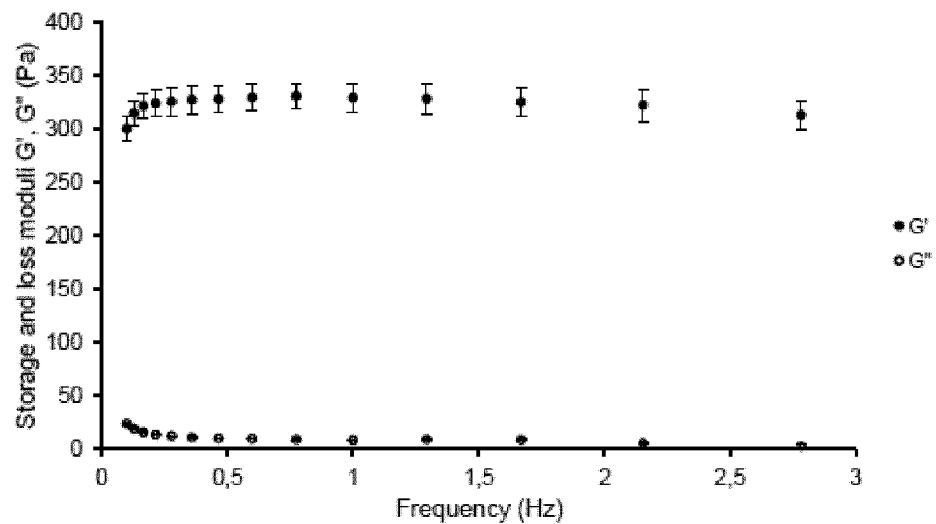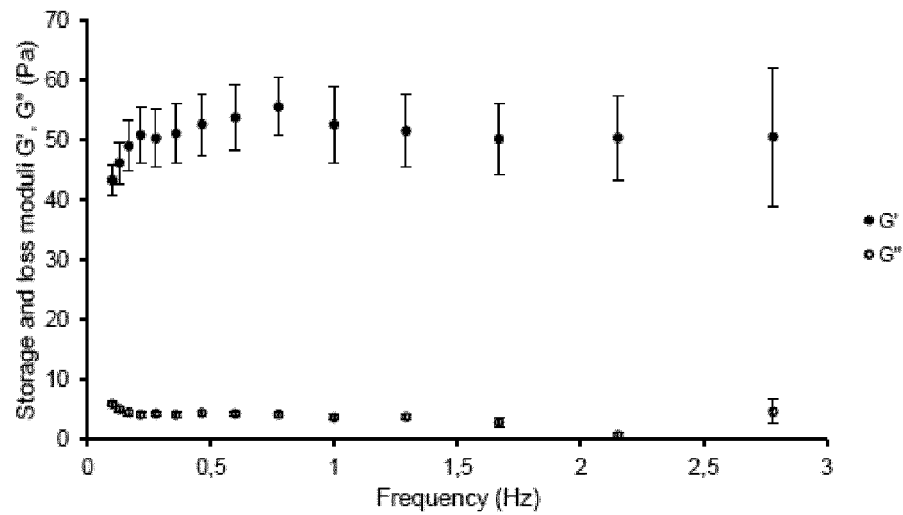
Figure 29

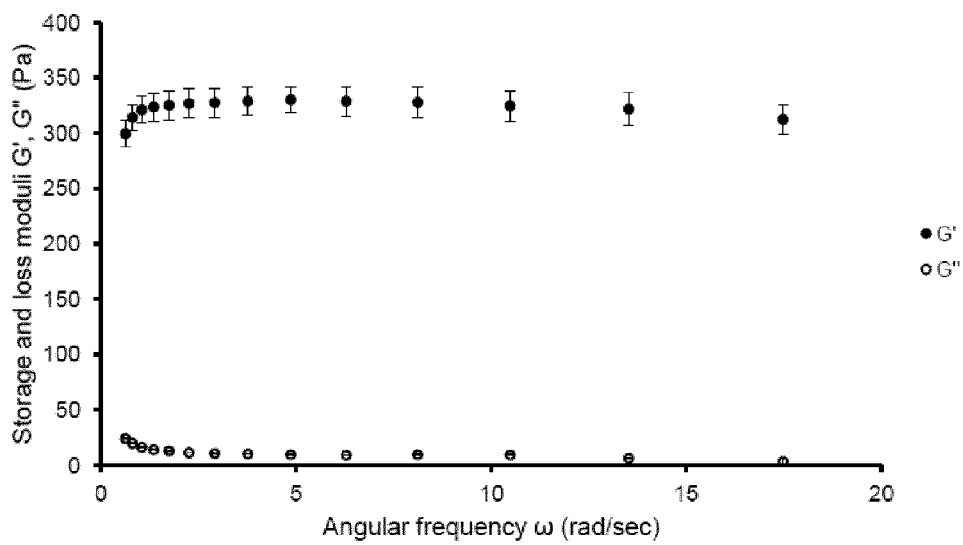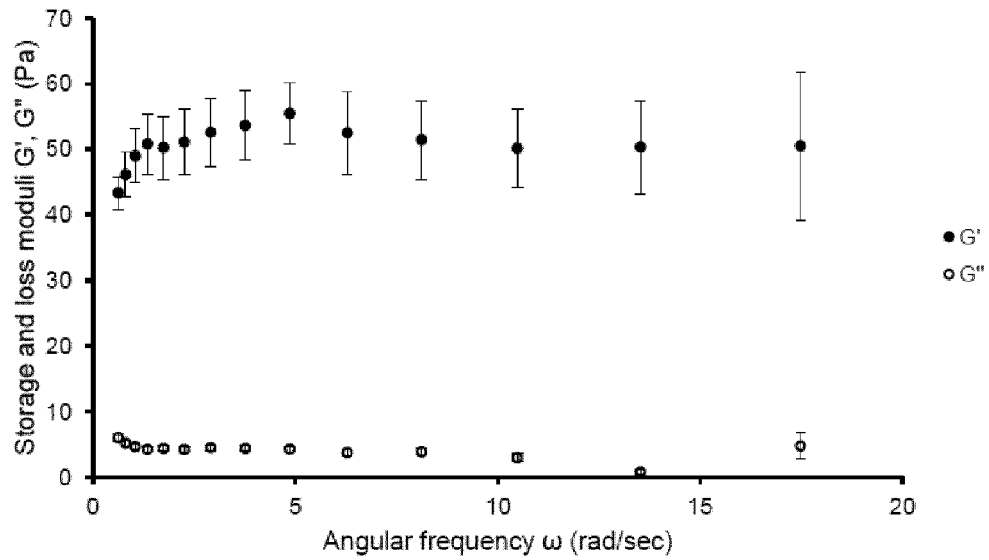
Figure 30

QVQLVESGGNLVQPGGSLRLSCAASGFTFGSFAMSWVRQAPGGGLEWVAGLSARSSLTHY
ADSVKGRFTISRDNAKNSVYLQMNSLRVEDTAVYYCARRSYDSSGYWGHFYSYMDVWGQG
TLVTVSSGGGGSGGGGSGGGGSQSVLTQPSSVSAAPGQKVTISCSGSTSNIGNAYVSWYQ
QHPGKAPKLMIYDVSKRPSGVPDRFSGSKSGNSASLDISGLQSEDEADYYCAAWDDSLSE
FLFGTGTKLTVLGASGADHHHHHH

Figure 33

SEQUENCE LISTING

```
<160> NUMBER OF SEQ ID NOS: 69

<210> SEQ ID NO 1
<211> LENGTH: 660
<212> TYPE: DNA
<213> ORGANISM: Escherichia coli
<220> FEATURE:
<221> NAME/KEY: misc_feature
<223> OTHER INFORMATION: GyrB nucleotide sequence

<400> SEQUENCE: 1
atgtcgaatt cttatgactc ctccagtatc aaagtcctga aagggctgga tgcggtgcgt      60
aagcgcccgg gtatgtatat cggcgacacg gatgacggca ccggtctgca ccacatggta     120
ttcgaggtgg tagataacgc tatcgacgaa gcgctcgcgg gtcactgtaa agaaattatc     180
gtcaccattc acgccgataa ctctgtctct gtacaggatg acgggcgcgg cattccgacc     240
ggtattcacc cggaagaggg cgtatcggcg gcggaagtga tcatgaccgt tctgcacgca     300
ggcggtaaat ttgacgataa ctcctataaa gtgtccggcg gtctgcacgg cgttggtgtt     360
tcggtagtaa acgccctgtc gcaaaaactg gagctggtta tccagcgcga gggtaaaatt     420
caccgtcaga tctacgaaca cggtgtaccg caggcccgc tggcggttac cggcgagact     480
gaaaaaaccg gcaccatggt gcgtttctgg cccagcctcg aaaccttcac caatgtgacc     540
gagttcgaat atgaaattct ggcgaaacgt ctgcgtgagt tgtcgttcct caactccggc     600
gtttccattc gtctgcgcga caagcgcgac ggcaaagaag accacttcca ctatgaaggc     660

<210> SEQ ID NO 2
<211> LENGTH: 220
<212> TYPE: PRT
<213> ORGANISM: Escherichia coli
<220> FEATURE:
<221> NAME/KEY: misc_feature
<223> OTHER INFORMATION: GyrB Protein sequence

<400> SEQUENCE: 2

Met Ser Asn Ser Tyr Asp Ser Ser Ser Ile Lys Val Leu Lys Gly Leu
1               5                   10                  15

Asp Ala Val Arg Lys Arg Pro Gly Met Tyr Ile Gly Asp Thr Asp Asp
            20                  25                  30
```

-continued

```
Gly Thr Gly Leu His His Met Val Phe Glu Val Val Asp Asn Ala Ile
        35                  40                  45

Asp Glu Ala Leu Ala Gly His Cys Lys Glu Ile Ile Val Thr Ile His
 50                  55                  60

Ala Asp Asn Ser Val Ser Val Gln Asp Gly Arg Gly Ile Pro Thr
 65                  70                  75                  80

Gly Ile His Pro Glu Glu Gly Val Ser Ala Ala Glu Val Ile Met Thr
                 85                  90                  95

Val Leu His Ala Gly Gly Lys Phe Asp Asp Asn Ser Tyr Lys Val Ser
            100                 105                 110

Gly Gly Leu His Gly Val Gly Val Ser Val Val Asn Ala Leu Ser Gln
        115                 120                 125

Lys Leu Glu Leu Val Ile Gln Arg Glu Gly Lys Ile His Arg Gln Ile
130                 135                 140

Tyr Glu His Gly Val Pro Gln Ala Pro Leu Ala Val Thr Gly Glu Thr
145                 150                 155                 160

Glu Lys Thr Gly Thr Met Val Arg Phe Trp Pro Ser Leu Glu Thr Phe
                165                 170                 175

Thr Asn Val Thr Glu Phe Glu Tyr Glu Ile Leu Ala Lys Arg Leu Arg
            180                 185                 190

Glu Leu Ser Phe Leu Asn Ser Gly Val Ser Ile Arg Leu Arg Asp Lys
        195                 200                 205

Arg Asp Gly Lys Glu Asp His Phe His Tyr Glu Gly
    210                 215                 220

<210> SEQ ID NO 3
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: "RGD" at positions 1-3 may repeat indefinitely

<400> SEQUENCE: 3

Arg Gly Asp
1

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide

<400> SEQUENCE: 4

Arg Gly Asp Ser
1

<210> SEQ ID NO 5
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(4)
<223> OTHER INFORMATION: "RGDS" at positions 1-4 may repeat indefinitely
```

```
<400> SEQUENCE: 5

Arg Gly Asp Ser
1

<210> SEQ ID NO 6
<211> LENGTH: 4
<212> TYPE: PRT
<213> ORGANISM: Artificial Sequence
<220> FEATURE:
<223> OTHER INFORMATION: Synthetic peptide

<400> SEQUENCE: 6

Gly Arg Gly Asp
1

<210> SEQ ID NO 7
<211> LENGTH: 4
<212> TYPE: PRT
<213> ORGANISM: Artificial Sequence
<220> FEATURE:
<223> OTHER INFORMATION: Synthetic peptide

<400> SEQUENCE: 7

Arg Gly Asp Val
1

<210> SEQ ID NO 8
<211> LENGTH: 4
<212> TYPE: PRT
<213> ORGANISM: Artificial Sequence
<220> FEATURE:
<223> OTHER INFORMATION: Synthetic peptide

<400> SEQUENCE: 8

Arg Gly Asp Thr
1

<210> SEQ ID NO 9
<211> LENGTH: 5
<212> TYPE: PRT
<213> ORGANISM: Artificial Sequence
<220> FEATURE:
<223> OTHER INFORMATION: Synthetic peptide

<400> SEQUENCE: 9

Gly Arg Gly Asp Gly
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic peptide

<400> SEQUENCE: 10

Gly Arg Gly Asp Ser
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic peptide

<400> SEQUENCE: 11
```

```
Gly Arg Gly Asp Tyr
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic peptide

<400> SEQUENCE: 12

Gly Arg Gly Asp Phe
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic peptide

<400> SEQUENCE: 13

Tyr Arg Gly Asp Ser
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic peptide

<400> SEQUENCE: 14

Tyr Arg Gly Asp Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic peptide

<400> SEQUENCE: 15

Tyr Gly Arg Gly Asp
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic peptide

<400> SEQUENCE: 16

Gly Arg Gly Asp Ser Pro
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic peptide

<400> SEQUENCE: 17
```

```
Gly Arg Gly Asp Ser Gly
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic peptide

<400> SEQUENCE: 18

Gly Arg Gly Asp Ser Pro
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic peptide

<400> SEQUENCE: 19

Gly Arg Gly Asp Ser Tyr
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic peptide

<400> SEQUENCE: 20

Gly Arg Gly Asp Val Tyr
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide

<400> SEQUENCE: 21

Gly Arg Gly Asp Ser Pro Lys
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic peptide

<400> SEQUENCE: 22

Cys Gly Arg Gly Asp Ser Pro Lys
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic peptide

<400> SEQUENCE: 23

Cys Gly Arg Gly Asp Ser Tyr
```

```
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic peptide

<400> SEQUENCE: 24

Tyr Ala Val Thr Gly Arg Gly Asp Ser
1               5

<210> SEQ ID NO 25
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 25

Cys Gly Gly Asn Gly Glu Pro Arg Gly Asp
1               5                   10

<210> SEQ ID NO 26
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: AMIDATION

<400> SEQUENCE: 26

Tyr Arg Ala Tyr
1

<210> SEQ ID NO 27
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 27

Gly Cys Gly Tyr Gly Arg Gly Asp Ser Pro Gly
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic

<400> SEQUENCE: 28

Arg Gly Asp Ser Pro Ala Ser Ser Lys Pro
1               5                   10
```

```
<210> SEQ ID NO 29
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 29

Gly Arg Gly Asp Ser Pro Ala Ser Ser Lys Gly
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is beta-alanine
<220> FEATURE:
<221> NAME/KEY: misc_feature
<222> LOCATION: (2)..(2)
<223> OTHER INFORMATION: Xaa is modified amino acid Dap (2,3-diamino
      propionic acid)

<400> SEQUENCE: 30

Xaa Xaa Glu Pro Arg Gly Asp Asn Tyr Arg Cys
1               5                   10

<210> SEQ ID NO 31
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: D-amino acid variant of phenylalanine

<400> SEQUENCE: 31

Lys Arg Gly Asp Phe
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: Penicillin in between Gly at position 1 and
      Gly at position 2

<400> SEQUENCE: 32

Gly Gly Arg Gly Asp Ser Pro Cys Ala
1               5

<210> SEQ ID NO 33
<211> LENGTH: 5
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: D-amino acid variant of valine

<400> SEQUENCE: 33

Val Arg Gly Asp Glu
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic peptide: FLAG tag

<400> SEQUENCE: 34

Asp Tyr Lys Asp Asp Asp Asp Lys
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic epitope derived from the Influenza
      protein haemagglutinin (HA)

<400> SEQUENCE: 35

Tyr Pro Tyr Asp Val Pro
1               5

<210> SEQ ID NO 36
<211> LENGTH: 10
<212> TYPE: PRT
<213> ORGANISM: Artificial Sequence
<220> FEATURE:
<223> OTHER INFORMATION: Synthetic epitope derived from the human
      proto-oncoprotein MYC

<400> SEQUENCE: 36

Ile Leu Lys Lys Ala Thr Ala Tyr Ile Leu
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Synthetic epitope derived from the human
      proto-oncoprotein MYC

<400> SEQUENCE: 37

Glu Gln Lys Leu Ile Ser Glu Glu Asp Leu
1               5                   10

<210> SEQ ID NO 38
<211> LENGTH: 39
<212> TYPE: PRT
<213> ORGANISM: Artificial Sequence
<220> FEATURE:
<223> OTHER INFORMATION: Synthetic amino acid

<400> SEQUENCE: 38

Ala Lys His Gln Ala Lys Cys Asn Ile Cys Lys Glu Cys Pro Ile Ile
1               5                   10                  15
```

Gly Phe Arg Tyr Arg Ser Leu Lys His Phe Asn Tyr Asp Ile Cys Gln
            20                  25                  30

Ser Cys Phe Phe Ser Gly Arg
        35

<210> SEQ ID NO 39
<211> LENGTH: 39
<212> TYPE: PRT
<213> ORGANISM: Artificial Sequence
<220> FEATURE:
<223> OTHER INFORMATION: Synthetic amino acid

<400> SEQUENCE: 39

Ala Lys His Gln Ala Lys Cys Asn Ile Cys Lys Glu Cys Pro Ile Val
1               5                   10                  15

Gly Phe Arg Tyr Arg Ser Leu Lys His Phe Asn Tyr Asp Val Cys Gln
            20                  25                  30

Ser Cys Phe Phe Ser Gly Arg
        35

<210> SEQ ID NO 40
<211> LENGTH: 129
<212> TYPE: PRT
<213> ORGANISM: Artificial Sequence
<220> FEATURE:
<223> OTHER INFORMATION: Synthetic amino acid
<220> FEATURE:
<221> NAME/KEY: misc_feature
<222> LOCATION: (1)..(1)
<223> OTHER INFORMATION: Met at position 1 may or may not be present

<400> SEQUENCE: 40

Met Ala Gln His Asp Glu Ala Val Asp Asn Lys Phe Asn Lys Glu Gln
1               5                   10                  15

Gln Asn Ala Phe Tyr Glu Ile Leu His Leu Pro Asn Leu Asn Glu Glu
            20                  25                  30

Gln Arg Asn Ala Phe Ile Gln Ser Leu Lys Asp Asp Pro Ser Gln Ser
        35                  40                  45

Ala Asn Leu Leu Ala Glu Ala Lys Lys Leu Asn Asp Ala Gln Ala Pro
    50                  55                  60

Lys Val Asp Asn Lys Phe Asn Lys Glu Gln Gln Asn Ala Phe Tyr Glu
65                  70                  75                  80

Ile Leu His Leu Pro Asn Leu Asn Glu Glu Gln Arg Asn Ala Phe Ile
                85                  90                  95

Gln Ser Leu Lys Asp Asp Pro Ser Gln Ser Ala Asn Leu Leu Ala Glu
            100                 105                 110

Ala Lys Lys Leu Asn Asp Ala Gln Ala Pro Lys Val Asp Ala Asn Ser
        115                 120                 125

Ser

<210> SEQ ID NO 41
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(4)
<223> OTHER INFORMATION: "SGGG" at positions 1 to 4 may repeat
      indefinitely

<400> SEQUENCE: 41

Ser Gly Gly Gly
1

<210> SEQ ID NO 42
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: "SGGGG" at positions 1 to 5 may repeat
      indefinitely

<400> SEQUENCE: 42

Ser Gly Gly Gly Gly
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(6)
<223> OTHER INFORMATION: "SGGGGG" at positions 1 to 6 may repeat
      indefinitely

<400> SEQUENCE: 43

Ser Gly Gly Gly Gly Gly
1               5

<210> SEQ ID NO 44
<211> LENGTH: 723
<212> TYPE: DNA
<213> ORGANISM: Artificial Sequence
<220> FEATURE:
<223> OTHER INFORMATION: Synthetic pRG107 Nucleotide sequence

<400> SEQUENCE: 44
atgtgctcga attcttatga ctcctccagt atcaaagtcc tgaaagggct ggatgcggtg    60
cgtaagcgcc cgggtatgta tatcggcgac acgatgacg gcaccggtct gcaccacatg   120
gtattcgagg tggtagataa cgctatcgac gaagcgctcg cgggtcactg taaagaaatt   180
atcgtcacca ttcacgccga taactctgtc tctgtacagg atgacgggcg cggcattccg   240
accggtattc acccggaaga gggcgtatcg gcggcggaag tgatcatgac cgttctgcac   300
gcaggcggta aatttgacga taactcctat aaagtgtccg cgcgtctgca cggcgttggt   360
gtttcggtag taaacgccct gtcgcaaaaa ctggagctgg ttatccagcg cgagggtaaa   420 attaccgtc agatctacga acacggtgta ccgcaggccc cgctggcggt taccggcgag   480
actgaaaaaa ccggcaccat ggtgcgtttc tggcccagcc tcgaaacctt caccaatgtg   540
accgagttcg aatatgaaat tctggcgaaa cgtctgcgtg agttgtcgtt cctcaactcc   600
ggcgtttcca ttcgtctgcg cgacaagcgc gacggcaaag aagaccactt ccactatgaa   660
ggcggccgtg gcgatagccc tggtcgtggt gactctccac atcatcacca tcaccattgc   720
tga                                                                  723

<210> SEQ ID NO 45

<211> LENGTH: 240
<212> TYPE: PRT
<213> ORGANISM: Artificial Sequence
<220> FEATURE:
<223> OTHER INFORMATION: Synthetic pRG107 Protein sequence

<400> SEQUENCE: 45

```
Met Cys Ser Asn Ser Tyr Asp Ser Ser Ile Lys Val Leu Lys Gly
1               5                  10                  15

Leu Asp Ala Val Arg Lys Arg Pro Gly Met Tyr Ile Gly Asp Thr Asp
            20                  25                  30

Asp Gly Thr Gly Leu His His Met Val Phe Glu Val Val Asp Asn Ala
        35                  40                  45

Ile Asp Glu Ala Leu Ala Gly His Cys Lys Glu Ile Ile Val Thr Ile
50                  55                  60

His Ala Asp Asn Ser Val Ser Val Gln Asp Asp Gly Arg Gly Ile Pro
65                  70                  75                  80

Thr Gly Ile His Pro Glu Glu Gly Val Ser Ala Ala Glu Val Ile Met
                85                  90                  95

Thr Val Leu His Ala Gly Gly Lys Phe Asp Asp Asn Ser Tyr Lys Val
            100                 105                 110

Ser Gly Gly Leu His Gly Val Gly Val Ser Val Val Asn Ala Leu Ser
        115                 120                 125

Gln Lys Leu Glu Leu Val Ile Gln Arg Glu Gly Lys Ile His Arg Gln
130                 135                 140

Ile Tyr Glu His Gly Val Pro Gln Ala Pro Leu Ala Val Thr Gly Glu
145                 150                 155                 160

Thr Glu Lys Thr Gly Thr Met Val Arg Phe Trp Pro Ser Leu Glu Thr
                165                 170                 175

Phe Thr Asn Val Thr Glu Phe Glu Tyr Glu Ile Leu Ala Lys Arg Leu
            180                 185                 190

Arg Glu Leu Ser Phe Leu Asn Ser Gly Val Ser Ile Arg Leu Arg Asp
        195                 200                 205

Lys Arg Asp Gly Lys Glu Asp His Phe His Tyr Glu Gly Gly Arg Gly
    210                 215                 220

Asp Ser Pro Gly Arg Gly Asp Ser Pro His His His His His His Cys
225                 230                 235                 240
```

<210> SEQ ID NO 46
<211> LENGTH: 1071
<212> TYPE: DNA
<213> ORGANISM: Artificial Sequence
<220> FEATURE:
<223> OTHER INFORMATION: Synthetic pRG111 nucleotide sequence

<400> SEQUENCE: 46

```
atggcgcaac acgatgaagc cgtagacaac aaattcaaca agaacaaca aaacgcgttc      60 tatgagatct acatttacc taacttaaac gaagaacaac gaaacgcctt catccaaagt     120
ttaaaagatg acccaagcca aagcgctaac ctttttagcag aagctaaaaa gctaaatgat     180
gctcaggcgc cgaaagtaga caacaaattc aacaagaac aacaaaacgc gttctatgag     240
atcttacatt tacctaactt aaacgaagaa caacgaaacg ccttcatcca agtttttaaaa    300 gatgacccaa gccaaagcgc taacctttta gcagaagcta aaaagctaaa tgatgctcag    360
gcgccgaaag tagacgcgaa ttcgagcatg tcgaattctt atgactcctc cagtatcaaa    420
gtcctgaaag ggctggatgc ggtgcgtaag cgcccgggta tgtatatcgg cgacacggat    480
```

```
gacggcaccg gtctgcacca catggtattc gaggtggtag ataacgctat cgacgaagcg    540
ctcgcgggtc actgtaaaga aattatcgtc accattcacg ccgataactc tgtctctgta    600
caggatgacg ggcgcggcat tccgaccggt attcacccgg aagagggcgt atcggcggcg    660
gaagtgatca tgaccgttct gcacgcaggc ggtaaatttg acgataactc ctataaagtg    720
tccggcggtc tgcacggcgt tggtgtttcg gtagtaaacg ccctgtcgca aaaactggag    780
ctggttatcc agcgcgaggg taaaattcac cgtcagatct acgaacacgg tgtaccgcag    840
gccccgctgg cggttaccgg cgagactgaa aaaccggca ccatggtgcg tttctggccc    900
agcctcgaaa ccttcaccaa tgtgaccgag ttcgaatatg aaattctggc gaaacgtctg    960
cgtgagttgt cgttcctcaa ctccggcgtt tccattcgtc tgcgcgacaa gcgcgacggc    1020
aaagaagacc acttccacta tgaaggccat catcaccatc accattgctg a              1071

<210> SEQ ID NO 47
<211> LENGTH: 356
<212> TYPE: PRT
<213> ORGANISM: Artificial Sequence
<220> FEATURE:
<223> OTHER INFORMATION: Synthetic pRG111 protein sequence

<400> SEQUENCE: 47

Met Ala Gln His Asp Glu Ala Val Asp Asn Lys Phe Asn Lys Glu Gln
1               5                   10                  15

Gln Asn Ala Phe Tyr Glu Ile Leu His Leu Pro Asn Leu Asn Glu Glu
            20                  25                  30

Gln Arg Asn Ala Phe Ile Gln Ser Leu Lys Asp Asp Pro Ser Gln Ser
        35                  40                  45

Ala Asn Leu Leu Ala Glu Ala Lys Lys Leu Asn Asp Ala Gln Ala Pro
    50                  55                  60

Lys Val Asp Asn Lys Phe Asn Lys Glu Gln Gln Asn Ala Phe Tyr Glu
65                  70                  75                  80

Ile Leu His Leu Pro Asn Leu Asn Glu Glu Gln Arg Asn Ala Phe Ile
                85                  90                  95

Gln Ser Leu Lys Asp Asp Pro Ser Gln Ser Ala Asn Leu Leu Ala Glu
            100                 105                 110

Ala Lys Lys Leu Asn Asp Ala Gln Ala Pro Lys Val Asp Ala Asn Ser
        115                 120                 125

Ser Met Ser Asn Ser Tyr Asp Ser Ser Ile Lys Val Leu Lys Gly
    130                 135                 140

Leu Asp Ala Val Arg Lys Arg Pro Gly Met Tyr Ile Gly Asp Thr Asp
145                 150                 155                 160

Asp Gly Thr Gly Leu His His Met Val Phe Glu Val Val Asp Asn Ala
                165                 170                 175

Ile Asp Glu Ala Leu Ala Gly His Cys Lys Glu Ile Ile Val Thr Ile
            180                 185                 190

His Ala Asp Asn Ser Val Ser Val Gln Asp Asp Gly Arg Gly Ile Pro
        195                 200                 205

Thr Gly Ile His Pro Glu Glu Gly Val Ser Ala Ala Glu Val Ile Met
    210                 215                 220

Thr Val Leu His Ala Gly Gly Lys Phe Asp Asp Asn Ser Tyr Lys Val
225                 230                 235                 240

Ser Gly Gly Leu His Gly Val Gly Val Ser Val Val Asn Ala Leu Ser
                245                 250                 255

Gln Lys Leu Glu Leu Val Ile Gln Arg Glu Gly Lys Ile His Arg Gln
```

```
            260                 265                 270
Ile Tyr Glu His Gly Val Pro Gln Ala Pro Leu Ala Val Thr Gly Glu
            275                 280                 285

Thr Glu Lys Thr Gly Thr Met Val Arg Phe Trp Pro Ser Leu Glu Thr
        290                 295                 300

Phe Thr Asn Val Thr Glu Phe Glu Tyr Glu Ile Leu Ala Lys Arg Leu
305                 310                 315                 320

Arg Glu Leu Ser Phe Leu Asn Ser Gly Val Ser Ile Arg Leu Arg Asp
                325                 330                 335

Lys Arg Asp Gly Lys Glu Asp His Phe His Tyr Glu Gly His His His
                340                 345                 350

His His His Cys
        355

<210> SEQ ID NO 48
<211> LENGTH: 720
<212> TYPE: DNA
<213> ORGANISM: Artificial Sequence
<220> FEATURE:
<223> OTHER INFORMATION: Synthetic pRG116 nucleotide sequence

<400> SEQUENCE: 48
atgtcgaatt cttatgactc tccagtatc aaagtcctga aagggctgga tgcggtgcgt      60
aagcgcccgg gtatgtatat cggcgacacg gatgacggca ccggtctgca ccacatggta    120
ttcgaggtgg tagataacgc tatcgacgaa gcgctcgcgg gtcactgtaa agaaattatc    180
gtcaccattc acgccgataa ctctgtctct gtacaggatg acgggcgcgg cattccgacc    240
ggtattcacc ggaagagggc gtatcggcg gcggaagtga tcatgaccgt tctgcacgca    300
ggcggtaaat ttgacgataa ctcctataaa gtgtccggcg tctgcacgg cgttggtgtt    360 tcggtagtaa acgccctgtc gcaaaaactg gagctggtta ccagcgcga gggtaaaatt    420 caccgtcaga tctacgaaca cggtgtaccg caggccccgc tggcggttac cggcgagact    480
gaaaaaaccg gcaccatggt gcgtttctgg cccagcctcg aaaccttcac caatgtgacc    540
gagttcgaat atgaaattct ggcgaaacgt ctgcgtgagt tgtcgttcct caactccggc    600
gtttccattc gtctgcgcga caagcgcgac ggcaaagaag accacttcca ctatgaaggc    660
ggccgtggcg atagccctgg tcgtggtgac tctccacatc atcaccatca ccattgctga    720

<210> SEQ ID NO 49
<211> LENGTH: 239
<212> TYPE: PRT
<213> ORGANISM: Artificial Sequence
<220> FEATURE:
<223> OTHER INFORMATION: Synthetic pRG116 protein sequence

<400> SEQUENCE: 49

Met Ser Asn Ser Tyr Asp Ser Ser Ile Lys Val Leu Lys Gly Leu
1               5                   10                  15

Asp Ala Val Arg Lys Arg Pro Gly Met Tyr Ile Gly Asp Thr Asp
                20                  25                  30

Gly Thr Gly Leu His His Met Val Phe Glu Val Val Asp Asn Ala Ile
            35                  40                  45

Asp Glu Ala Leu Ala Gly His Cys Lys Glu Ile Ile Val Thr Ile His
        50                  55                  60

Ala Asp Asn Ser Val Ser Val Gln Asp Asp Gly Arg Gly Ile Pro Thr
65                  70                  75                  80
```

```
Gly Ile His Pro Glu Glu Gly Val Ser Ala Ala Glu Val Ile Met Thr
            85                  90                  95
Val Leu His Ala Gly Lys Phe Asp Asp Asn Ser Tyr Lys Val Ser
        100                 105                 110
Gly Gly Leu His Gly Val Gly Val Ser Val Val Asn Ala Leu Ser Gln
            115                 120                 125
Lys Leu Glu Leu Val Ile Gln Arg Glu Gly Lys Ile His Arg Gln Ile
        130                 135                 140
Tyr Glu His Gly Val Pro Gln Ala Pro Leu Ala Val Thr Gly Glu Thr
145                 150                 155                 160
Glu Lys Thr Gly Thr Met Val Arg Phe Trp Pro Ser Leu Glu Thr Phe
                165                 170                 175
Thr Asn Val Thr Glu Phe Glu Tyr Glu Ile Leu Ala Lys Arg Leu Arg
            180                 185                 190
Glu Leu Ser Phe Leu Asn Ser Gly Val Ser Ile Arg Leu Arg Asp Lys
        195                 200                 205
Arg Asp Gly Lys Glu Asp His Phe His Tyr Glu Gly Gly Arg Gly Asp
    210                 215                 220
Ser Pro Gly Arg Gly Asp Ser Pro His His His His His Cys
225                 230                 235
```

```
<210> SEQ ID NO 50
<211> LENGTH: 106
<212> TYPE: PRT
<213> ORGANISM: Artificial Sequence
<220> FEATURE:
<223> OTHER INFORMATION: Synthetic FFG-7 protein sequence

<400> SEQUENCE: 50
```

```
Met His Lys Trp Ile Leu Thr Trp Ile Leu Pro Thr Leu Leu Tyr Arg
1               5                   10                  15
Ser Cys Phe His Ile Ile Cys Leu Val Gly Thr Ile Ser Leu Ala Cys
            20                  25                  30
Asn Asp Met Thr Pro Glu Gln Met Ala Thr Asn Val Asn Cys Ser Ser
        35                  40                  45
Pro Glu Arg His Thr Arg Ser Tyr Asp Tyr Met Glu Gly Glu Asp Ile
    50                  55                  60
Arg Val Arg Arg Leu Phe Cys Arg Thr Gln Trp Tyr Leu Arg Ile Asp
65                  70                  75                  80
Lys Arg Gly Lys Val Lys Gly Thr Gln Glu Met Lys Asn Asn Tyr Ser
                85                  90                  95
Lys Gly Asn Tyr Asn Gly Pro Lys Val Ala
            100                 105
```

```
<210> SEQ ID NO 51
<211> LENGTH: 1083
<212> TYPE: DNA
<213> ORGANISM: Artificial Sequence
<220> FEATURE:
<223> OTHER INFORMATION: Synthetic FGF-7-Fc-His Nucleotide sequence

<400> SEQUENCE: 51
```
atgcacaaat ggatactgac atggatcctg ccaactttgc tctacagatc atgctttcac      60
attatctgtc tagtgggtac tatatcttta gcttgcaatg acatgactcc agagcaaatg     120
gctacaaatg tgaactgttc cagccctgag cgacacacaa gaagttatga ttacatggaa     180
ggagaggata taagagtgag aagactcttc tgtcgaacac agtggtaccc tgaggatcgat    240

```
aaaagaggca aagtaaaagg gacccaagag atgaagaata attacagtaa gggtaactat    300
aacggtccta aggtagcgag tggtggaggc ggttcaggcg gaggtggctc tggcggtggc    360
ggatcgccca gagggcccac aatcaagccc tgtcctccat gcaaatgccc agcacctaac    420
ctcgagggtg gaccatccgt cttcatcttc cctccaaaga tcaaggatgt actcatgatc    480
tccctgagcc ccatagtcac atgtgtggtg gtggatgtga gcgaggatga cccagatgtc    540
cagatcagct ggtttgtgaa caacgtggaa gtacacacag tcagacaca aacccataga    600 gaggattaca acagtactct ccgggtggtc agtgccctcc ccatccagca ccaggactgg    660
atgagtggca aggcgttcgc atgcgcggtc aacaacaaag acctcccagc gcccatcgag    720
agaaccatct caaaacccaa agggtcagta agagctccac aggtatatgt cttgcctcca    780
ccagaagaag agatgactaa gaaacaggtc actctgacct gcatggtcac agacttcatg    840
cctgaagaca tttacgtgga gtggaccaac aacgggaaaa cagagctaaa ctacaagaac    900
actgaaccag tcctggactc tgatggttct tacttcatgt acagcaagct gagagtggaa    960
aagaagaact gggtggaaag aaatagctac tcctgttcag tggtccacga gggtctgcac   1020
aatcaccaca cgactaagag cttctcccgg actccgggta acaccatca ccatcaccat   1080 tga                                                                  1083
```

<210> SEQ ID NO 52
<211> LENGTH: 360
<212> TYPE: PRT
<213> ORGANISM: Artificial Sequence
<220> FEATURE:
<223> OTHER INFORMATION: Synthetic FGF-7-Fc-His Protein sequence

<400> SEQUENCE: 52

```
Met His Lys Trp Ile Leu Thr Trp Ile Leu Pro Thr Leu Leu Tyr Arg
1               5                   10                  15

Ser Cys Phe His Ile Ile Cys Leu Val Gly Thr Ile Ser Leu Ala Cys
                20                  25                  30

Asn Asp Met Thr Pro Glu Gln Met Ala Thr Asn Val Asn Cys Ser Ser
            35                  40                  45

Pro Glu Arg His Thr Arg Ser Tyr Asp Tyr Met Glu Gly Glu Asp Ile
        50                  55                  60

Arg Val Arg Arg Leu Phe Cys Arg Thr Gln Trp Tyr Leu Arg Ile Asp
65                  70                  75                  80

Lys Arg Gly Lys Val Lys Gly Thr Gln Glu Met Lys Asn Asn Tyr Ser
                85                  90                  95

Lys Gly Asn Tyr Asn Gly Pro Lys Val Ala Ser Gly Gly Gly Gly Ser
            100                 105                 110

Gly Gly Gly Gly Ser Gly Gly Gly Ser Pro Arg Gly Pro Thr Ile
        115                 120                 125

Lys Pro Cys Pro Pro Cys Lys Cys Pro Ala Pro Asn Leu Glu Gly Gly
    130                 135                 140

Pro Ser Val Phe Ile Phe Pro Pro Lys Ile Lys Asp Val Leu Met Ile
145                 150                 155                 160

Ser Leu Ser Pro Ile Val Thr Cys Val Val Val Asp Val Ser Glu Asp
                165                 170                 175

Asp Pro Asp Val Gln Ile Ser Trp Phe Val Asn Asn Val Glu Val His
            180                 185                 190

Thr Ala Gln Thr Gln Thr His Arg Glu Asp Tyr Asn Ser Thr Leu Arg
        195                 200                 205
```

```
Val Val Ser Ala Leu Pro Ile Gln His Gln Asp Trp Met Ser Gly Lys
            210                 215                 220

Ala Phe Ala Cys Ala Val Asn Asn Lys Asp Leu Pro Ala Pro Ile Glu
225                 230                 235                 240

Arg Thr Ile Ser Lys Pro Lys Gly Ser Val Arg Ala Pro Gln Val Tyr
            245                 250                 255

Val Leu Pro Pro Glu Glu Glu Met Thr Lys Lys Gln Val Thr Leu
            260                 265                 270

Thr Cys Met Val Thr Asp Phe Met Pro Glu Asp Ile Tyr Val Glu Trp
            275                 280                 285

Thr Asn Asn Gly Lys Thr Glu Leu Asn Tyr Lys Asn Thr Glu Pro Val
            290                 295                 300

Leu Asp Ser Asp Gly Ser Tyr Phe Met Tyr Ser Lys Leu Arg Val Glu
305                 310                 315                 320

Lys Lys Asn Trp Val Glu Arg Asn Ser Tyr Ser Cys Ser Val Val His
            325                 330                 335

Glu Gly Leu His Asn His His Thr Thr Lys Ser Phe Ser Arg Thr Pro
            340                 345                 350

Gly Lys His His His His His His
            355                 360

<210> SEQ ID NO 53
<211> LENGTH: 232
<212> TYPE: PRT
<213> ORGANISM: Artificial Sequence
<220> FEATURE:
<223> OTHER INFORMATION: Synthetic protein sequence

<400> SEQUENCE: 53

Pro Arg Gly Pro Thr Ile Lys Pro Cys Pro Pro Cys Lys Cys Pro Ala
1               5                   10                  15

Pro Asn Leu Glu Gly Gly Pro Ser Val Phe Ile Phe Pro Pro Lys Ile
            20                  25                  30

Lys Asp Val Leu Met Ile Ser Leu Ser Pro Ile Val Thr Cys Val Val
            35                  40                  45

Val Asp Val Ser Glu Asp Asp Pro Asp Val Gln Ile Ser Trp Phe Val
        50                  55                  60

Asn Asn Val Glu Val His Thr Ala Gln Thr Gln Thr His Arg Glu Asp
65                  70                  75                  80

Tyr Asn Ser Thr Leu Arg Val Val Ser Ala Leu Pro Ile Gln His Gln
                85                  90                  95

Asp Trp Met Ser Gly Lys Ala Phe Ala Cys Ala Val Asn Asn Lys Asp
            100                 105                 110

Leu Pro Ala Pro Ile Glu Arg Thr Ile Ser Lys Pro Lys Gly Ser Val
            115                 120                 125

Arg Ala Pro Gln Val Tyr Val Leu Pro Pro Glu Glu Glu Met Thr
130                 135                 140

Lys Lys Gln Val Thr Leu Thr Cys Met Val Thr Asp Phe Met Pro Glu
145                 150                 155                 160

Asp Ile Tyr Val Glu Trp Thr Asn Asn Gly Lys Thr Glu Leu Asn Tyr
                165                 170                 175

Lys Asn Thr Glu Pro Val Leu Asp Ser Asp Gly Ser Tyr Phe Met Tyr
            180                 185                 190

Ser Lys Leu Arg Val Glu Lys Lys Asn Trp Val Glu Arg Asn Ser Tyr
        195                 200                 205
```

Ser Cys Ser Val His Glu Gly Leu His Asn His His Thr Thr Lys
    210                 215                 220

Ser Phe Ser Arg Thr Pro Gly Lys
225                 230

<210> SEQ ID NO 54
<211> LENGTH: 522
<212> TYPE: DNA
<213> ORGANISM: Artificial Sequence
<220> FEATURE:
<223> OTHER INFORMATION: Synthetic nucleic acid sequence of FluA -
      flourescein

<400> SEQUENCE: 54
gacgtgtacc ac

```
<210> SEQ ID NO 56
<211> LENGTH: 552
<212> TYPE: DNA
<213> ORGANISM: Artificial Sequence
<220> FEATURE:
<223> OTHER INFORMATION: Synthetic nucleic acid sequence of DigA
      (DigA_16)

<400> SEQUENCE: 56
gacgtgtacc acgacggcgc ctgccccgaa gtgaagcccg tggacaactt cgactggtcc      60
cagtaccacg gcaagtggtg gcaggtggcc gcttatcccg accacatcac caagtacggc     120
aagtgcggct gggccgagta caccccgag ggcaagagcg tgaaggtgtc ccggtacagc      180
gtgatccacg gcaaagagta cttcagcgag ggcaccgcct accctgtggg cgacagcaag     240
atcggcaaga tctaccacag ctacaccatc ggcggcgtga cccaggaggg cgtgttcaac     300
gtgctgtcca ccgacaacaa gaactacatc atcggctact tttgcagata cgacgaggac     360
aagaagggcc acatggactt ggtgtgggtg ctgtcccggt ccatggtgct gaccggcgag     420
gccaagaccg ccgtggagaa ctacctgatc ggcagccccg tggtggacag ccagaaactg     480
gtgtacagcg acttctccga ggccgcctgc aaagtgaaca acagcaactg gtcccacccc     540
cagttcgaaa ag                                                        552

<210> SEQ ID NO 57
<211> LENGTH: 185
<212> TYPE: PRT
<213> ORGANISM: Artificial Sequence
<220> FEATURE:
<223> OTHER INFORMATION: Synthetic amino acid sequence of DigA (DigA_16)

<400> SEQUENCE: 57

Met Asp Val Tyr His Asp Gly Ala Cys Pro Glu Val Lys Pro Val Asp
1               5                   10                  15

Asn Phe Asp Trp Ser Gln Tyr His Gly Lys Trp Trp Gln Val Ala Ala
            20                  25                  30

Tyr Pro Asp His Ile Thr Lys Tyr Gly Lys Cys Gly Trp Ala Glu Tyr
        35                  40                  45

Thr Pro Glu Gly Lys Ser Val Lys Val Ser Arg Tyr Ser Val Ile His
    50                  55                  60

Gly Lys Glu Tyr Phe Ser Glu Gly Thr Ala Tyr Pro Val Gly Asp Ser
65                  70                  75                  80

Lys Ile Gly Lys Ile Tyr His Ser Tyr Thr Ile Gly Gly Val Thr Gln
                85                  90                  95

Glu Gly Val Phe Asn Val Leu Ser Thr Asp Asn Lys Asn Tyr Ile Ile
            100                 105                 110

Gly Tyr Phe Cys Ser Tyr Asp Glu Asp Lys Lys Gly His Met Asp Leu
        115                 120                 125

Val Trp Val Leu Ser Arg Ser Met Val Leu Thr Gly Glu Ala Lys Thr
    130                 135                 140

Ala Val Glu Asn Tyr Leu Ile Gly Ser Pro Val Val Asp Ser Gln Lys
145                 150                 155                 160

Leu Val Tyr Ser Asp Phe Ser Glu Ala Ala Cys Lys Val Asn Asn Ser
                165                 170                 175

Asn Trp Ser His Pro Gln Phe Glu Lys
            180                 185

<210> SEQ ID NO 58
```

<211> LENGTH: 1029
<212> TYPE: DNA
<213> ORGANISM: Artificial Sequence
<220> FEATURE:
<223> OTHER INFORMATION: Synthetic nucleic acid sequence of Salicyclic
      Acid Binding Protein 2 (SABP2)

<400> SEQUENCE: 58

```
ggaaaacact ttgttttagt acatggtgca tgccatggag gttggagttg gtacaagcta      60
aagccactgc tagaagctgc aggccataag gttacagccc ttgatttagc agcttctggc     120
actgatttga gaaaaataga ggagcttcgc acactttatg attatacttt gccattgatg     180
gagttgatgg aatctctttc agcagatgag aaggttatat tagtggggca tagtcttggt     240
ggtatgaatt tgggacttgc tatggaaaag tatccacaaa agatctatgc tgctgttttc     300
ttggctgctt tcatgcctga ttctgttcac aactcctcct ttgttttgga acagtataat     360
gagcggacgc cagccgagaa ttggttggat actcagtttt taccatatgg ttcccctgaa     420
gagccactga catccatgtt ttttggccca aagttcttgg ctcacaagct ctaccagcta     480
tgctctcctg aggatcttgc attagcatca tcattggtga gaccaagctc tttgtttatg     540
gaagacctat cgaaggccaa gtatttcaca gatgaacggt ttggatcagt gaagagagtt     600
tacattgtgt gcactgagga taaaggcata ccagaagaat tccagcgatg gcaaattgac     660
aacattggtg tcactgaagc aatagagatt aaaggtgctg atcacatggc aatgctatgc     720
gagccccaaa actttgcgc tctctcttg gaaattgccc ataaatacaa ctgatctcta     780
cattatgtct tcgtctcatg tcaagatttt cagtgcatgc tgtaattttt ttctattttt     840
cgaccggcgc ataactgtct ttgcctattt taaggattgc agtaatttca ctcttctagt     900
gtggaaggct tccacataag gattgttctg tttctccatt caagtgtgtg ttatgttgag     960
atacttaaac cgtatcaatt cttgtaatga aacttcttct ttccttttg aaaaaaaaaa    1020
aaaaaaaaa                                                           1029
```

<210> SEQ ID NO 59
<211> LENGTH: 260
<212> TYPE: PRT
<213> ORGANISM: Artificial Sequence
<220> FEATURE:
<223> OTHER INFORMATION: Synthetic amino acid sequence of Salicyclic
      Acid Binding Protein 2 (SABP2)

<400> SEQUENCE: 59

```
Met Lys Glu Gly Lys His Phe Val Leu Val His Gly Ala Cys His Gly
1               5                   10                  15
Gly Trp Ser Trp Tyr Lys Leu Lys Pro Leu Leu Glu Ala Ala Gly His
            20                  25                  30
Lys Val Thr Ala Leu Asp Leu Ala Ala Ser Gly Thr Asp Leu Arg Lys
        35                  40                  45
Ile Glu Glu Leu Arg Thr Leu Tyr Asp Tyr Thr Leu Pro Leu Met Glu
    50                  55                  60
Leu Met Glu Ser Leu Ser Ala Asp Glu Lys Val Ile Leu Val Gly His
65                  70                  75                  80
Ser Leu Gly Gly Met Asn Leu Gly Leu Ala Met Glu Lys Tyr Pro Gln
                85                  90                  95
Lys Ile Tyr Ala Ala Val Phe Leu Ala Ala Phe Met Pro Asp Ser Val
            100                 105                 110
His Asn Ser Ser Phe Val Leu Glu Gln Tyr Asn Glu Arg Thr Pro Ala
        115                 120                 125
```

| Glu | Asn | Trp | Leu | Asp | Thr | Gln | Phe | Leu | Pro | Tyr | Gly | Ser | Pro | Glu | Glu |
| | | 130 | | | | 135 | | | | 140 | | | | | |

| Pro | Leu | Thr | Ser | Met | Phe | Phe | Gly | Pro | Lys | Phe | Leu | Ala | His | Lys | Leu |
| 145 | | | | | 150 | | | | | 155 | | | | | 160 |

| Tyr | Gln | Leu | Cys | Ser | Pro | Glu | Asp | Leu | Ala | Leu | Ala | Ser | Ser | Leu | Val |
| | | | | 165 | | | | 170 | | | | | 175 | | |

| Arg | Pro | Ser | Ser | Leu | Phe | Met | Glu | Asp | Leu | Ser | Lys | Ala | Lys | Tyr | Phe |
| | | | | 180 | | | | | 185 | | | | 190 | | |

| Thr | Asp | Glu | Arg | Phe | Gly | Ser | Val | Lys | Arg | Val | Tyr | Ile | Val | Cys | Thr |
| | | | 195 | | | | | 200 | | | | | 205 | | |

| Glu | Asp | Lys | Gly | Ile | Pro | Glu | Glu | Phe | Gln | Arg | Trp | Gln | Ile | Asp | Asn |
| | 210 | | | | | 215 | | | | | 220 | | | | |

| Ile | Gly | Val | Thr | Glu | Ala | Ile | Glu | Ile | Lys | Gly | Ala | Asp | His | Met | Ala |
| 225 | | | | | 230 | | | | | 235 | | | | | 240 |

| Met | Leu | Cys | Glu | Pro | Gln | Lys | Leu | Cys | Ala | Ser | Leu | Leu | Glu | Ile | Ala |
| | | | | 245 | | | | | 250 | | | | | 255 | |

| His | Lys | Tyr | Asn |
| | | | 260 |

<210> SEQ ID NO 60
<211> LENGTH: 1079
<212> TYPE: DNA
<213> ORGANISM: Artificial Sequence
<220> FEATURE:
<223> OTHER INFORMATION: Synthetic nucleic acid sequence of Salicyclic
      Acid Binding Protein 2 (SABP2 S81A)

<400> SEQUENCE: 60

```
acgcggggaa agaaaagaaa ctaacaaggc ataaaattca aatgaaggaa ggaaaacact      60
ttgttttagt acatggtgca tgccatggag gttggagttg gtacaagcta aagccactgc     120
tagaagctgc aggccataag gttacagccc ttgatttagc agcttctggc actgatttga     180
gaaaaataga ggagcttcgc acactttatg attatacttt gccattgatg gagttgatgg     240
aagctctttc agcagatgag aaggttatat tagtggggca tagtcttggt ggtatgaatt     300
tgggacttgc tatggaaaag tatccacaaa agatctatgc tgctgttttc ttggctgctt     360
tcatgcctga ttctgttcac aactcctcct tgttttggga acagtataat gagcggacgc     420
cagccgagaa ttggttggat actcagtttt taccatatgg ttcccctgaa gagccactga     480
catccatgtt ttttggccca agttcttgg ctcacaagct ctaccagcta tgctctcctg      540
aggatcttgc attagcatca tcattggtga gaccaagctc tttgtttatg aagacctat     600
cgaaggccaa gtatttcaca gatgaacggt ttggatcagt gaagagagtt tacattgtgt     660
gcactgagga taaggcata ccagaagaat ccagcgatg gcaaattgac aacattggtg       720
tcactgaagc aatagagatt aaaggtgctg atcacatggc aatgctatgc gagccccaaa     780
aactttcgc ctctctcttg gaaattgccc ataaatacaa ctgatctcta cattatgtct      840
tcgtctcatg tcaagatttt cagtgcatgc tgtaattttt ttctattttt cgaccggcgc     900
ataactgtct ttgcctattt taaggattgc agtaatttca ctcttctagt gtggaaggct     960
tccacataag gattgttctg tttctccatt caagtgtgtg ttatgttgag atacttaaac    1020
cgtatcaatt cttgtaatga aacttcttct ttccttttg aaaaaaaaaa aaaaaaaa      1079
```

<210> SEQ ID NO 61
<211> LENGTH: 260
<212> TYPE: PRT

<213> ORGANISM: Artificial Sequence
<220> FEATURE:
<223> OTHER INFORMATION: Synthetic amino acid sequence of Salicyclic
      Acid Binding Protein 2 (SABP2 S81A)

<400> SEQUENCE: 61

```
Met Lys Glu Gly Lys His Phe Val Leu Val His Gly Ala Cys His Gly
1               5                   10                  15

Gly Trp Ser Trp Tyr Lys Leu Lys Pro Leu Leu Glu Ala Ala Gly His
            20                  25                  30

Lys Val Thr Ala Leu Asp Leu Ala Ala Ser Gly Thr Asp Leu Arg Lys
        35                  40                  45

Ile Glu Glu Leu Arg Thr Leu Tyr Asp Tyr Thr Leu Pro Leu Met Glu
    50                  55                  60

Leu Met Glu Ser Leu Ser Ala Asp Glu Lys Val Ile Leu Val Gly His
65                  70                  75                  80

Ala Leu Gly Gly Met Asn Leu Gly Leu Ala Met Glu Lys Tyr Pro Gln
                85                  90                  95

Lys Ile Tyr Ala Ala Val Phe Leu Ala Ala Phe Met Pro Asp Ser Val
            100                 105                 110

His Asn Ser Ser Phe Val Leu Glu Gln Tyr Asn Glu Arg Thr Pro Ala
        115                 120                 125

Glu Asn Trp Leu Asp Thr Gln Phe Leu Pro Tyr Gly Ser Pro Glu Glu
    130                 135                 140

Pro Leu Thr Ser Met Phe Phe Gly Pro Lys Phe Leu Ala His Lys Leu
145                 150                 155                 160

Tyr Gln Leu Cys Ser Pro Glu Asp Leu Ala Leu Ala Ser Ser Leu Val
                165                 170                 175

Arg Pro Ser Ser Leu Phe Met Glu Asp Leu Ser Lys Ala Lys Tyr Phe
            180                 185                 190

Thr Asp Glu Arg Phe Gly Ser Val Lys Arg Val Tyr Ile Val Cys Thr
        195                 200                 205

Glu Asp Lys Gly Ile Pro Glu Glu Phe Gln Arg Trp Gln Ile Asp Asn
    210                 215                 220

Ile Gly Val Thr Glu Ala Ile Glu Ile Lys Gly Ala Asp His Met Ala
225                 230                 235                 240

Met Leu Cys Glu Pro Gln Lys Leu Cys Ala Ser Leu Leu Glu Ile Ala
                245                 250                 255

His Lys Tyr Asn
            260
```

<210> SEQ ID NO 62
<211> LENGTH: 1098
<212> TYPE: DNA
<213> ORGANISM: Artificial Sequence
<220> FEATURE:
<223> OTHER INFORMATION: Synthetic nucleic acid sequence of Arabidopsis
      FK506 binding protein (FKBP42)

<400> SEQUENCE: 62

```
atggatgaat ctctggagca tcaaactcaa acacatgacc aagagagcga aatagttact      60
gaaggaagtg ccgttgtgca tagtgagcca tctcaagagg gtaatgttcc tcctaaagtt     120
gatagtgaag ctgaggtctt ggatgagaaa gtcagtaagc agattataaa ggaaggtcac     180
ggttccaaac catccaagta ctctacatgc tttttgcact acagggcatg gaccaaaaac     240
tcgcagcaca aatttgagga tacatggcat gagcagcaac ctattgaatt ggttcttgga     300
```

```
aaagagaaaa aagaactagc cggtttagcc atcggtgttg ctagcatgaa gtctggtgaa      360
cgtgcgcttg tgcatgttgg ctgggaatta gcttatggga aagaaggaaa cttttcttt      420 ccgaatgttc cacctatggc agacttgtta tatgaggtgg aagttattgg gtttgatgaa      480
acaaaggagg gaaaagctcg cagtgatatg actgtagagg aaaggattgg tgcagcagac      540
agaagaaaaa tggatgggaa ttctcttttt aaggaggaga actggagga agccatgcaa      600 cagtatgaaa tggccatagc atacatgggg gacgattta tgtttcagct gtatgggaag      660
taccaggata tggctttagc agttaaaaac ccatgccatc ttaacatagc agcttgcctc      720
atcaaactaa acgatacga tgaagcaatt ggtcactgca acattgtgtt gacagaagaa      780
gagaaaaacc caaaagcact gttcagaaga gggaaagcaa aggcagagct aggacagatg      840
gactcagcac gtgatgattt ccgaaaggca caaaagtatg ctcctgacga caaggcgatt      900
agaagagagc tacgagcact tgcagagcaa agaaaagcct tgtaccaaaa gcagaaagaa      960
atgtacaaag gaatattcaa agggaaagat gaaggtggtg ctaagtcaaa gagccttttt     1020
tggttgatag tgttatggca atggtttgtt tcccttttct cccgtatctt tcgacgccac     1080
agagttaaag cagattaa                                                   1098
```

<210> SEQ ID NO 63
<211> LENGTH: 493
<212> TYPE: DNA
<213> ORGANISM: Artificial Sequence
<220> FEATURE:
<223> OTHER INFORMATION: Synthetic nucleic acid sequence of Arabidopsis
      FK506 binding protein (FKBP42)

<400> SEQUENCE: 63

```
atggatgaat ctctggagca tcaaactcaa acacatgacc aagagagcga aatagttact       60
gaaggaagtg ccgttgtgca tagtgagcca tctcaagagg gtaatgttcc tcctaaagtt      120
gatagtgaag ctgaggtctt ggatgagaaa gtcagtaagc agattataaa ggaaggtcac      180
ggttccaaac catccaagta ctctacatgc tttttgcact acagggcatg gaccaaaaac      240
tcgcagcaca aatttgagga tacatggcat gagcagcaac ctattgaatt ggttcttgga      300
aaagagaaaa agaactagc cggtttagcc atcggtgttg ctagcatgaa gtctggtgaa      360
cgtgcgcttg tgcatgttgg ctgggaatta gcttatggga aagaaggaaa cttttcttt      420 ccgaatgttc cacctatggc agacttgtta tatgaggtgg aagttattgg gtttgatgaa      480
acaaaggagg taa                                                         493
```

<210> SEQ ID NO 64
<211> LENGTH: 163
<212> TYPE: PRT
<213> ORGANISM: Artificial Sequence
<220> FEATURE:
<223> OTHER INFORMATION: Synthetic amino acid sequence of Arabidopsis
      FK506 binding protein (FKBP42)

<400> SEQUENCE: 64

Met Asp Glu Ser Leu Glu His Gln Thr Gln Thr His Asp Gln Glu Ser
1               5                   10                  15

Glu Ile Val Thr Glu Gly Ser Ala Val Val His Ser Glu Pro Ser Gln
            20                  25                  30

Glu Gly Asn Val Pro Pro Lys Val Asp Ser Glu Ala Glu Val Leu Asp
        35                  40                  45

Glu Lys Val Ser Lys Gln Ile Ile Lys Glu Gly His Gly Ser Lys Pro
    50                  55                  60

Ser Lys Tyr Ser Thr Cys Phe Leu His Tyr Arg Ala Trp Thr Lys Asn
 65                  70                  75                  80

Ser Gln His Lys Phe Glu Asp Thr Trp His Glu Gln Gln Pro Ile Glu
                 85                  90                  95

Leu Val Leu Gly Lys Lys Lys Glu Leu Ala Gly Leu Ala Ile Gly
            100                 105                 110

Val Ala Ser Met Lys Ser Gly Glu Arg Ala Leu Val His Val Gly Trp
        115                 120                 125

Glu Leu Ala Tyr Gly Lys Gly Asn Phe Ser Phe Pro Asn Val Pro
    130                 135                 140

Pro Met Ala Asp Leu Leu Tyr Glu Val Glu Val Ile Gly Phe Asp Glu
145                 150                 155                 160

Thr Lys Glu

<210> SEQ ID NO 65
<211> LENGTH: 891
<212> TYPE: DNA
<213> ORGANISM: Artificial Sequence
<220> FEATURE:
<223> OTHER INFORMATION: Synthetic nucleic acid sequence of Arabidopsis
      multiresistance-like ABC transporter AtPGP1

<400> SEQUENCE: 65
atgctcagat ccggtctggc ttcgttaatc gtcgatgtca atttgcggcg cacgttacgt      60
ccatccccaa cctttctctt tccggcgcat cttagccgtt gcattatcac ttcccgttac     120
tcctcccgta catctctaag gtttccgatt caaatatctc gccaccaaca ccgtctatcc     180
tactttctct catcctcttc gtcggagcaa agcagaccaa cttcctcttc ccgaaacagt     240
ttcagtggtc acgtcagct tgatagtgat gataattctt caccgcctcc gtcgcaatca     300
tcttccaaag ttcttacatt gcctaccgta ttaacacttg gtcgtgtcgc cgccgtcccg     360
cttctcgtcg caaccttta cgttgatagt tggtggggaa caactgctac aacaagcatt     420
ttcattgcag cagccattac agactggctt gacggctatc ttgcccgcaa gatgaggtta     480
ggttctgcgt ttggtgcctt tttggatcca gttgctgata gcttatggt tgcagctaca     540 ttgattttac tgtgtacaaa acctatccaa gttgctgaat taggaccact tccatggtta     600
ttgaccgtac cttctattgc aatcattggt agggagatta ctatgtccgc agtaagagaa     660
tgggctgcat ctcaaaatgg aaagcttta gaggcagttg ctgtaaataa cttgggcaag     720
tggaaaaccg ccacgcagat gacagcacta accatacttc ttgcaagccg agatagcaat     780
gttggatggc tcgtagcttc aggtgctggc ttgctttatg tatcagcagg actatctgtt     840
tggtctttag ccgtttatat gaggaagata tggaaagtac taatgaagta g              891

<210> SEQ ID NO 66
<211> LENGTH: 296
<212> TYPE: PRT
<213> ORGANISM: Artificial Sequence
<220> FEATURE:
<223> OTHER INFORMATION: Synthetic amino acid sequence of Arabidopsis
      multiresistance-like ABC transporter AtPGP1

<400> SEQUENCE: 66

Met Leu Arg Ser Gly Leu Ala Ser Leu Ile Val Asp Val Asn Leu Arg
1               5                   10                  15

Arg Thr Leu Arg Pro Ser Pro Thr Phe Ser Phe Pro Ala His Leu Ser
            20                  25                  30

Arg Cys Ile Ile Thr Ser Arg Tyr Ser Ser Arg Thr Ser Leu Arg Phe
          35                  40                  45

Pro Ile Gln Ile Ser Arg His Gln His Arg Leu Ser Tyr Phe Ser Ser
 50                  55                  60

Ser Ser Ser Ser Glu Gln Ser Arg Pro Thr Ser Ser Ser Arg Asn Ser
 65                  70                  75                  80

Phe Ser Gly His Gly Gln Leu Asp Ser Asp Asn Ser Ser Pro Pro
                 85                  90                  95

Pro Ser Gln Ser Ser Lys Val Leu Thr Leu Pro Thr Val Leu Thr
                100                 105                 110

Leu Gly Arg Val Ala Ala Val Pro Leu Leu Val Ala Thr Phe Tyr Val
         115                 120                 125

Asp Ser Trp Gly Thr Thr Ala Thr Thr Ser Ile Phe Ile Ala Ala
 130                 135                 140

Ala Ile Thr Asp Trp Leu Asp Gly Tyr Leu Ala Arg Lys Met Arg Leu
145                 150                 155                 160

Gly Ser Ala Phe Gly Ala Phe Leu Asp Pro Val Ala Asp Lys Leu Met
                165                 170                 175

Val Ala Ala Thr Leu Ile Leu Leu Cys Thr Lys Pro Ile Gln Val Ala
                180                 185                 190

Glu Leu Gly Pro Leu Pro Trp Leu Leu Thr Val Pro Ser Ile Ala Ile
        195                 200                 205

Ile Gly Arg Glu Ile Thr Met Ser Ala Val Arg Glu Trp Ala Ala Ser
210                 215                 220

Gln Asn Gly Lys Leu Leu Glu Ala Val Ala Val Asn Asn Leu Gly Lys
225                 230                 235                 240

Trp Lys Thr Ala Thr Gln Met Thr Ala Leu Thr Ile Leu Leu Ala Ser
                245                 250                 255

Arg Asp Ser Asn Val Gly Trp Leu Val Ala Ser Gly Ala Gly Leu Leu
                260                 265                 270

Tyr Val Ser Ala Gly Leu Ser Val Trp Ser Leu Ala Val Tyr Met Arg
        275                 280                 285

Lys Ile Trp Lys Val Leu Met Lys
        290                 295

<210> SEQ ID NO 67
<211> LENGTH: 920
<212> TYPE: DNA
<213> ORGANISM: Artificial Sequence
<220> FEATURE:
<223> OTHER INFORMATION: Synthetic nucleic acid sequence of Arabidopsis
      multiresistance-like ABC transporter AtPGP1

<400> SEQUENCE: 67
cactggctcc tgatttcatc aaaggtggtc aagctatgcg gtctgttttc gaacttcttg      60
accggaaaac cgagattgaa cctgatgatc ctgataccac cccggtccca gaccggttac     120
gtggtgaagt cgagctcaaa catatcgatt tctcttaccc ttcaaggcca gacatccaga     180
ttttccgtga ccttagcctt cgtgctagag ctggcaaaac cctagctctt gtgggtccaa     240
gcgggtgcgg aaaaagctca gttatctccc tcatccagag attctacgaa ccttcctcag     300
gccgagtcat gatcgacggg aaagacataa ggaaatacaa cctgaaagcc ataaggaaac     360
acatagccat agtccctcaa gagccgtgct tgttcggaac taccatttac gaaacattg      420 catatggaca tgaatgtgcg accgaagcag agatcataca agccgcgact ctagccagtg     480
cgcacaaatt catatccgcg ctaccagaag gttacaaaac gtatgttggc gagagaggcg     540

```
ttcagctctc gggaggacag aaacagagga tcgcgatcgc acgtgccctc gtgaggaaag    600
cagagatcat gctgcttgac gaggctacaa gcgctcttga tgcagagtcc gagagatcag    660
tccaagaagc attagaccag gcttgctctg gtagaacatc aatagtcgtg gctcataggc    720
tatctacaat caggaacgca cacgtgatcg ctgtcatcga tgatggaaaa gtggctgaac    780
aaggatcgca ttcgcatctt ctcaagaacc atcctgatgg aatctacgcg cgaatgatac    840
agttgcaaag atttacgcat acacaagtga ttggtatgac gtcaggttca agttctaggg    900
ttaaggaaga tgatgcttag                                                920
```

```
<210> SEQ ID NO 68
<211> LENGTH: 306
<212> TYPE: PRT
<213> ORGANISM: Artificial Sequence
<220> FEATURE:
<223> OTHER INFORMATION: Synthetic amino acid sequence of Arabidopsis
      multiresistance-like ABC transporter AtPGP1

<400> SEQUENCE: 68

Thr Leu Ala Pro Asp Phe Ile Lys Gly Gly Gln Ala Met Arg Ser Val
1               5                   10                  15

Phe Glu Leu Leu Asp Arg Lys Thr Glu Ile Glu Pro Asp Asp Pro Asp
                20                  25                  30

Thr Thr Pro Val Pro Asp Arg Leu Arg Gly Glu Val Glu Leu Lys His
            35                  40                  45

Ile Asp Phe Ser Tyr Pro Ser Arg Pro Asp Ile Gln Ile Phe Arg Asp
        50                  55                  60

Leu Ser Leu Arg Ala Arg Ala Gly Lys Thr Leu Ala Leu Val Gly Pro
65                  70                  75                  80

Ser Gly Cys Gly Lys Ser Ser Val Ile Ser Leu Ile Gln Arg Phe Tyr
                85                  90                  95

Glu Pro Ser Ser Gly Arg Val Met Ile Asp Gly Lys Asp Ile Arg Lys
            100                 105                 110

Tyr Asn Leu Lys Ala Ile Arg Lys His Ile Ala Ile Val Pro Gln Glu
        115                 120                 125

Pro Cys Leu Phe Gly Thr Thr Ile Tyr Glu Asn Ile Ala Tyr Gly His
    130                 135                 140

Glu Cys Ala Thr Glu Ala Glu Ile Ile Gln Ala Ala Thr Leu Ala Ser
145                 150                 155                 160

Ala His Lys Phe Ile Ser Ala Leu Pro Glu Gly Tyr Lys Thr Tyr Val
                165                 170                 175

Gly Glu Arg Gly Val Gln Leu Ser Gly Gly Gln Lys Gln Arg Ile Ala
            180                 185                 190

Ile Ala Arg Ala Leu Val Arg Lys Ala Glu Ile Met Leu Leu Asp Glu
        195                 200                 205

Ala Thr Ser Ala Leu Asp Ala Glu Ser Glu Arg Ser Val Gln Glu Ala
    210                 215                 220

Leu Asp Gln Ala Cys Ser Gly Arg Thr Ser Ile Val Val Ala His Arg
225                 230                 235                 240

Leu Ser Thr Ile Arg Asn Ala His Val Ile Ala Val Ile Asp Asp Gly
                245                 250                 255

Lys Val Ala Glu Gln Gly Ser His Ser His Leu Leu Lys Asn His Pro
            260                 265                 270

Asp Gly Ile Tyr Ala Arg Met Ile Gln Leu Gln Arg Phe Thr His Thr
        275                 280                 285
```

```
Gln Val Ile Gly Met Thr Ser Gly Ser Ser Arg Val Lys Glu Asp
    290                 295                 300

Asp Ala
305

<210> SEQ ID NO 69
<211> LENGTH: 264
<212> TYPE: PRT
<213> ORGANISM: Artificial Sequence
<220> FEATURE:
<223> OTHER INFORMATION: Synthetic amino acid sequence of scFv

<400> SEQUENCE: 69

Gln Val Gln Leu Val Glu Ser Gly Gly Asn Leu Val Gln Pro Gly Gly
1               5                   10                  15

Ser Leu Arg Leu Ser Cys Ala Ala Ser Gly Phe Thr Phe Gly Ser Phe
            20                  25                  30

Ala Met Ser Trp Val Arg Gln Ala Pro Gly Gly Gly Leu Glu Trp Val
        35                  40                  45

Ala Gly Leu Ser Ala Arg Ser Ser Leu Thr His Tyr Ala Asp Ser Val
    50                  55                  60

Lys Gly Arg Phe Thr Ile Ser Arg Asp Asn Ala Lys Asn Ser Val Tyr
65                  70                  75                  80

Leu Gln Met Asn Ser Leu Arg Val Glu Asp Thr Ala Val Tyr Tyr Cys
                85                  90                  95

Ala Arg Arg Ser Tyr Asp Ser Ser Gly Tyr Trp Gly His Phe Tyr Ser
            100                 105                 110

Tyr Met Asp Val Trp Gly Gln Gly Thr Leu Val Thr Val Ser Ser Gly
        115                 120                 125

Gly Gly Gly Ser Gly Gly Gly Gly Ser Gly Gly Gly Gly Ser Gln Ser
    130                 135                 140

Val Leu Thr Gln Pro Ser Ser Val Ser Ala Ala Pro Gly Gln Lys Val
145                 150                 155                 160

Thr Ile Ser Cys Ser Gly Ser Thr Ser Asn Ile Gly Asn Ala Tyr Val
                165                 170                 175

Ser Trp Tyr Gln Gln His Pro Gly Lys Ala Pro Lys Leu Met Ile Tyr
            180                 185                 190

Asp Val Ser Lys Arg Pro Ser Gly Val Pro Asp Arg Phe Ser Gly Ser
        195                 200                 205

Lys Ser Gly Asn Ser Ala Ser Leu Asp Ile Ser Gly Leu Gln Ser Glu
    210                 215                 220

Asp Glu Ala Asp Tyr Tyr Cys Ala Ala Trp Asp Asp Ser Leu Ser Glu
225                 230                 235                 240

Phe Leu Phe Gly Thr Gly Thr Lys Leu Thr Val Leu Gly Ala Ser Gly
                245                 250                 255

Ala Asp His His His His His His
            260
```

BIO-FUNCTIONALIZED STIMULUS-RESPONSIVE DISSOLVABLE PEG-HYDROGELS

The present invention is directed to a bio-functionalized stimulus-responsive dissolvable PEG-hydrogel. This inventive stimulus-responsive dissolvable PEG-hydrogel comprises a matrix of PEG-polymers, which are modified to contain at least one multifunctional fusion protein, the multifunctional fusion protein preferably comprising as components a substrate binding peptide (SBP), preferably a repetitive RGD-binding peptide and/or a ZZ-binding domain, preferably a tag for purification, and at least one N- and/or C-terminal linker. The present invention is furthermore directed to the use of such inventive stimulus-responsive dissolvable PEG-hydrogels in the treatment of lesions, in surgical dressings, for wound treating, for soft and hard tissue regeneration, for the treatment of wounds in the oral cavity, in the field of ophthalmology, in the field of periodontal defects, etc. The invention also describes a method for treatment of such diseases. Additionally, the present invention provides a kit comprising the inventive stimulus-responsive dissolvable PEG-hydrogel and optionally further components.

Biological systems, such as the skin, the connective tissues, or the bones within the skeleton system are complex systems, the regeneration and/or repair of which occurs under spatially- and temporally-controlled orchestration. A myriad of signals and cells act in space and time to heal a wound, for example, to replace a destroyed part of the skin during tissue regeneration, or to induce or support the growth of bone, etc. In many of these cases, cavities have to be filled to prevent a loss of soft and/or hard tissue, or to prevent a significant reduction or even a collapse thereof. However, efficacy of many current biomaterials used to construct carriers or matrices suitable for such treatments is limited by a lack of multifunctional structures to complement the inherent dynamics of these biological systems.

In this context, multiple physical, chemical, and biological cues are known to act cooperatively and/or synergistically to affect cellular function during tissue regeneration in vitro and in vivo. To design successful biomaterials for facilitating tissue regeneration, one must therefore thoughtfully consider the interplay between the targeted cells/tissues and these environmental cues. Important factors are usually soluble growth factors, cell-cell and cell-material interactions, and mechanical properties of the microenvironment (see e.g. Lin and Anseth, Expert Review, "PEG hydrogels for the controlled Release of Biomolecules in Regenerative Medicine", Pharmaceutical Research, Vol. 26, No. 3, March 2009).

Bearing in mind these requirements, the delivery of bioactive molecules and the search for suitable carriers has been the subject of intensive research, as the targeted molecules are diverse, including low molecular weight drugs, nucleic acids, peptides, growth factors and hormones, and proteins, for the accelerated regeneration of tissues.

One promising approach in this area is based on the use of so-called hydrogels. Hydrogels represent a class of materials with numerous advantages to simultaneously harbour cells and biomolecules. There are also numerous possibilities which allow one to intimately control the release characteristics through systematic changes in the gel's physical and chemical structure (see e.g. C. C. Lin, and A. T. Metters. Hydrogels in controlled release formulations: Network design and mathematical modeling. Adv. Drug Deliv. Rev. 58:1379-1408 (2006)). Due to their variable properties, hydrogels have been used to allow for preparation of so-called synthetic "stimuli-responsive" polymers, which resemble structures of natural tissues and tissue models. Based on their chemical and physical properties, these synthetic "stimuli-responsive" polymers have been coined with different names, e.g. 'stimuli-responsive' polymers, 'smart' polymers, 'environmental-sensitive' polymers or 'intelligent' polymers (see Brawa et al., Biomed. Mater. 4 (2009) 022001 (15 pp)). The distinguishing characteristic of these stimuli-responsive polymers is their ability to undergo rapid changes in their microstructure from a hydrophilic to a hydrophobic state, which is triggered by small changes in the environment. The macroscopic changes that occur are reversible; therefore, the system is capable of returning to its initial state when the trigger is removed. Common stimuli that drive these changes are further categorized as either external or internal stimuli. Externally controlled systems rely on externally applied stimuli that are produced with the help of different stimuli-generating devices, which ultimately results in pulsed drug delivery. Internally regulated systems are also known as self-regulated devices, where the release rate is controlled by a feedback mechanism that is produced within the body to control the structural changes in the polymer network and to exhibit the desired drug release, without any external intervention. Stimuli of "stimuli-responsive" polymers may be e.g. a change of solvent, pH, temperature, electric current, magnetic fields or mechanical stress. Responses to these stimuli may be manifested as changes in shape, surface characteristics, solubility, and formation of an intricate molecular assembly or a sol-to-gel transition (see Brawa et al., Biomed. Mater. 4 (2009) 022001 (15 pp)).

Hydrogels, which can be used as synthetic "stimuli-responsive" polymers may be based on synthetic polymers, such as poly(ethylene glycol) (PEG), poly(vinyl alcohol) (PVA), poly(N-isopropylacrylamide) (poly(NiPAAm)). Such hydrogels have been used in numerous regenerative applications (see e.g. N. A. Peppas, P. Bures, W. Leobandung, and H. Ichikawa. Hydrogels in pharmaceutical formulations. Eur. J. Pharm. Biopharm. 50:27-46 (2000)).

In this context, Schmaljohann et al. (Schmaljohann, D., Nitschke, M., Schulze, R., Werner, C., Eichhorn, K.-J., "Patterning of stimuli-responsive hydrogels", Polymer Preprints 45, 380-381, December 2004) discloses a thermo-responsive hydrogel based on a poly(NiPAAm-co-PEGMA) precursor. The material has been demonstrated to show a temperature-induced change in cell adhesion and detachment behavior.

Likewise, Voit et al. (Voit, B.; Schmaljohann, D.; Gramm, S., Nitschke, M., Werner, C., "Stimuli-responsive polymer layers for advanced cell culture technologies", International Journal of Materials Research 98, 646-650, August 2007) disclose a series of graft copolymers consisting of poly(N-isopropylacrylamide) as a thermoresponsive component in the polymer backbone and poly(ethyleneglycol) side chains. The surface-immobilized hydrogels exhibit a transition from partially collapsed to completely swollen, which is in the range of 32-35° C. and corresponds to the lower critical solution temperature of the soluble polymers. The hydrogel-coated supports were found to permit adhesion, spreading and proliferation of cells and allow for fast and effective temperature-dependent detachment of intact cell sheets or multiple cell types.

However, temperature-sensitive gels, even though suitable for some cell based in vitro applications, are not suitable for in vivo administration since the temperature stimulus has to be provided within the patient or at the administration site during or subsequent to administration of the stimulus-responsive hydrogel to a patient to be treated. Similar problems will occur when utilizing stimulus-responsive hydrogels, the stimuli of which are selected from a change of solvent, pH, electric current, magnetic fields or mechanical stress. Such temperature-sensitive or pH-sensitive hydrogels gels are, for example, described in WO 2009/144569 and WO 2010/068728.

Hydrogels, suitable as stimulus-responsive hydrogels, can also be formed by cross-linking. Cross-linking provides a suitable method to modify gels to exhibit higher viscosities due to an apparent or real increase of the molecular weight, which often results in the formation of gels. Cross-linking can be achieved chemically by the formation of covalent bonds or physically by the formation of e.g. hydrogen bonds or ionic interactions. Obviously, cross-linking can also be achieved both chemically and physically. Chemical cross-linking of hydrophilic polymers is a general and often applied route to obtain hydrogels. In order to be able to administer or process these gels, prepolymers are dissolved in water and are then polymerized resulting in situ hydrogel formation. Hydrogellation procedures are often based on the use of acrylic or methacrylic macromonomers that are not preferred in (biomedical) applications, because of their inherent toxicity and because they usually require an auxiliary, potentially hazardous, initiator for polymerization. Moreover, chemically cross-linked hydrogels lack reversibility and are limited in their degradation behavior, as poly(acrylate)s and poly(methacrylate)s are not biodissolvable.

For example, U.S. Pat. No. 5,410,016 discloses hydrogels based on copolymers of poly(ethylene glycol) with poly(DL-lactide) containing pendant acrylate functions that are cross-linked in situ. WO 01/44307 discloses hydrogels based on polyvinyl alcohol modified with pendant acrylate and methacrylate groups that are chemically cross-linked in situ. Hence, according to these prior art references, an irreversible cross-linked hydrogel is obtained by starting from water processable prepolymers that contain reactive groups.

One further cross-linking approach was shown in US 2009/0117656, which used reversible disulfide linkages to interconnect synthetic polymer strains, such as water-soluble polymers including polyamino acids, saccharides, polyesters, polyamides, polyethers, vinyl polymers, and the copolymers thereof (see e.g. US 2009/0117656). For this purpose reactive compounds, such as, e.g. cystamine, cystine, 2-hydroxyethyldisulfide, 3,3'-dithiodipropionic acid (DTDP), glutathione disulfide, 3,3'-dithiopropiohydrazide, the derivatives thereof, and the like, may be used as a cross-linking agent. The peptide is then usually formed by self-assembly in an aqueous medium subsequent to modification of the synthetic polymer with the reactive compound.

A further approach of this kind is directed to hydrogels of dextran polymers made from cross-linking acryloylated dextrin with homo-, mono- and bifunctional active molecules, e.g. peptides having one or two cysteines at their ends (see US 2007/0167354). More precisely, US 2007/0167354 discloses a matrix for inducing cell migration, wherein two peptides are covalently linked to the matrix, a first peptide being cleavable by natural proteases, e.g. by tissue matrix metalloproteinases (MMPs), and a second peptide comprising a cell-attracting peptide, e.g. an RGD peptide. These two peptides promote cell-induced adhesion and enzymatic degradation of the hydrogel. By changing the percentage compositions of these two peptides with respect to the total available cross-links, the extent of cell adhesion and migration through the gel can be regulated. However, this approach again utilizes acrylic or methacrylic macromonomers that are not preferred in biomedical applications.

A specific form of cross-linked hydrogels represent the so-called heparin-functionalized hydrogels. Nie et al. (see Ting Nie, Aaron Baldwin, Nori Yamaguchi, Kristi L. Kiick, "Production of heparin-functionalized hydrogels for the development of responsive and controlled growth factor delivery systems", Journal of Controlled Release 122 (2007) 287-296) report about non-covalent assembly of heparinized materials as a route to responsive, reversible, and injectable drug delivery systems, with main interests in protein delivery and the production of ECM-mimetic materials. In this context, poly(ethylene glycol) star polymers functionalized with heparin-binding peptides can be mixed directly with heparin to form viscoelastic solutions with tunable properties, or can be mixed with star poly(ethylene glycol)-heparin conjugates to form non-covalent hydrogels capable of growth factor delivery via hydrogel erosion. Such erosion strategies, although passive, may offer unique opportunities for improving growth factor activity via the co-release of growth factor with the heparinized macro-molecules. Nie et al. have also reported that the PEG-heparin conjugates are competent for the formation of elastic hydrogels via the interaction with dimeric, heparin-binding growth factors, such as vascular endothelial growth factor (VEGF). Importantly, these hydrogels are capable of receptor-mediated VEGF release and hydrogel erosion upon exposure to the VEGF receptor VEGFR-2, and given the primary role of the VEGFR-2 in controlling the proliferation and migration of vascular endothelial cells, these results suggest important strategies for the targeted delivery of drugs in vascular and wound healing therapies.

One further example of heparin-functionalized hydrogels is disclosed in Kim et al. (2007), which utilized heparin-functionalized hydrogels for the binding and delivery of growth factors. More precisely, Kim et al. (2007) have reported the non-covalent assembly of hydrogels via interaction between heparin and heparin-binding peptides or growth factors, as well as the delivery of growth factors from these matrices via passive or receptor-mediated matrix erosion. In this context, four-arm star poly(ethylene glycol) (PEG) modified with heparin has been shown to form hydrogels when mixed with star PEGs, modified with heparin-binding peptides. The peptides used were derived from heparin-interacting protein (HIP), antithrombin III (ATIII), or platelet factor 4 (PF4ZIP). Such modified polymers form hydrogels through non-covalent primarily electrostatic interactions, and the hydrogels can be loaded with therapeutically relevant growth factors.

The mechanical strength of such heparin-functionalized hydrogels can be controlled by choosing different heparin-binding peptides and polymer compositions. In addition, the distribution of the charged heparin throughout the matrix may also facilitate homogeneous incorporation of growth factors into the delivery vehicle. Advantageously, the lack of toxic cross-linking agents in the gels, coupled with the potential for their non-invasive administration (e.g., via injection) may permit their use in multiple clinical and therapeutical applications. In addition, growth factors, such as vascular endothelial growth factor (VEGF), can be employed as cross-links in the assembly of these hydrogel networks, since they provide two cross-linking points per molecule. Upon administration at a target site, the growth factor may be removed from the gel via binding with its receptors, and subsequently through receptor-mediated endocytosis, which would cause erosion due to the loss of physical cross-linking points and would theoretically permit elimination of the polymer matrix if PEG molecules of appropriate molecular weight are used. Such a delivery system could be flexibly applied for numerous targets, depending on the desired growth factor employed in the matrix; in theory, multiple growth factors could also be used in a single matrix to permit delivery and erosion on multiple timescales that depend on the affinity of the growth factor for heparin. Nevertheless, even though this system provides some desirable and advantageous properties, it is exclusively directed to the provision of growth factors in vitro or in vivo. The growth of tissue and incorporation of specific factors or cells into such a hydrogel is not addressed.

Another specific form of cross-linked hydrogels is shown in WO 2009/146929. WO 2009/146929 discloses a specifically cross-linked hydrogel utilizing a polymer, a specific first polypeptide and a specific polypeptide binding partner, which may be identical or different to the first polypeptide. Both polypeptides are bound covalently or non-covalently to the polymer and allow forming the hydrogel upon interaction between the first polypeptide and the polypeptide binding partner. Specific polypeptides used in WO 2009/146929 are e.g. GyrB, FKBP, FRB, $F_M$, ToxT, DHFR, and Cyp. However, even though WO 2009/146929 already allows the incorporation of drugs and effector substances, such compounds typically leach out within a rather short time limit. Additionally, such hydrogels poorly support the inclusion of cells onto or even into the matrix. Gels according to WO 2009/146929 therefore may be less suitable for long-term treatments or at least require repeated administration, e.g. during support or reconstitution of tissue, e.g. after operations, or in general for tissue growth, or supplementation of tissue growth. In this context, only a few systems are known in the art that in fact allow, though not efficiently enough, the growth of tissue and the inclusion of cells onto or even into a matrix and application of such matrices.

Among the different hydrogels the non-ionic, hydrophilic PEG gel systems appear to provide many possibilities for such purposes with respect to tailoring gel properties. Non-ionic, hydrophilic PEG gel systems are additionally regarded as being non-toxic and exhibiting an excellent biocompatibility. Consequently, these poly(ethylene glycol) (PEG) hydrogels have been extensively discussed over the past few decades as matrices for controlling drug delivery, as well as cell delivery vehicles for promoting tissue regeneration. Accordingly, in the context of controlled delivery, properly designed PEG hydrogels may play an important role in directing cellular functions that are important for survival, adhesion, proliferation, matrix synthesis, secretory properties, and even differentiation. The objectives and design principles for this purpose are two-fold: to provide local and extended release of the loaded therapeutics, to augment the therapeutic effect and to decrease the adverse reactions and preserve the bioactivity of the therapeutics. To achieve these goals, one has to carefully consider several critical factors, including the physiological environments of the target cells and tissues, gelation and molecule loading/release mechanisms, molecular characteristics of the therapeutics to be delivered, as well as potential interactions with the polymeric hydrogels.

PEG hydrogels provide a unique niche as cell carrying substrate, as they are highly biocompatible to the cells under proper polymerization conditions. Through co-polymerization with other macro-molecules, multiple functional moieties may be introduced to suppress or promote cell survival and function. For example, the integrin binding peptide Arg-Gly-Asp (or RGD) may be introduced as a pendant functional group within otherwise bio-inert PEG hydrogels to promote the survival of adherence-dependent cells, such as osteoblasts (J. A. Burdick, and K. S. Anseth. Photoencapsulation of osteoblasts in injectable RGD-modified PEG hydrogels for bone tissue engineering. Biomaterials. 23:4315-4323 (2002)).

However, even though PEG hydrogel environments are generally highly permissible and allow for facile diffusion of nutrients, this property often hinders the localized delivery and therapeutic efficacy of soluble factors targeted to the encapsulated cells, as the inert gel networks are equally permeable to the co-encapsulated therapeutics. The means by which bioactive molecules are presented to encapsulated cells within PEG hydrogel networks both temporally and spatially is therefore still a major challenge in the design of hydrogel delivery systems and is currently a subject of intense research.

Summarizing the above, many advantageous and promising approaches have been discussed in the recent years. Nevertheless, none of these approaches appears to provide hydrogels with both a good suitability for in vivo applications and a sufficient flexibility for effectively binding and releasing various factors and/or cells to the hydrogel within an easy and fast approach. Furthermore, none of these hydrogels appear to be additionally suitable as a sort of cell and/or tissue matrix for in vitro and/or in vivo applications for the purposes of cell in-growth and/or regeneration of tissues in a patient to be treated.

Accordingly, it was the object underlying the present invention to provide novel means, preferably a novel stimulus-responsive dissolvable PEG-hydrogel matrix, and methods of producing same, which exhibit both a good suitability for in vivo applications and a sufficient flexibility for effectively binding and releasing various factors and/or cells to the hydrogel within an easy and fast approach.

This object is solved by the subject matter of the attached claims.

According to a first specific embodiment, the object underlying the present invention is solved by a stimulus-responsive dissolvable PEG-hydrogel, comprising a matrix of PEG-polymers, which are modified to contain at least one multifunctional fusion protein, the multifunctional fusion protein preferably comprising as components a substrate binding peptide (SBP), preferably a repetitive RGD-binding peptide, and/or a ZZ-binding domain, preferably a tag for purification, and at least one N- and/or C-terminal linker.

Advantageously, the inventive stimulus-responsive dissolvable PEG-hydrogel can be produced cost efficiently and provides a great variability. It may be prepared on the basis of a pharmaceutically licensed polyethylene glycol polymer covalently grafted with a substrate binding peptide (SBP). Gel formation is easily achieved by interaction of substrate binding peptides (SBP) as defined herein, preferably via a specific substrate or by binding of the substrate binding peptide (SBP) to its specific substrate, e.g. dimerization of two GyrB subunits via coumermycin or binding of GyrB to coumermycin. Addition of an antagonistic compound or the substrate in excess, e.g. novobiocin in the case of GyrB, allows for adjustable dissolution of the hydrogel. The incorporation of cell adhesion motifs, e.g. in form of a repetitive RGD-binding peptide $(RGD_n)$, also written as $RGD_n$ or $(RGD)_n$, into the fusion protein sequence, allows for cell growth on the hydrogel. Embedded growth factors, e.g. FGF-7 (Fibroblast Growth Factor-7, or KGF, keratinocyte growth factor) in the hydrogel, e.g. via a ZZ-binding domain, can be released time controlled, and in a dose-responsive manner by the inducer novobiocin.

According to the first embodiment, the inventive multifunctional fusion protein used to modify the PEG-polymers of the PEG-matrix, preferably comprises as components a substrate binding peptide (SBP), preferably a repetitive RGD-binding peptide, such as $(RGD_n)$, also defined as $RGD_n$ or $(RGD)_n$, and/or a ZZ-binding domain, preferably a tag for purification, and at least one N- and/or C-terminal linker.

Typically, the substrate binding peptide (SBP) of the inventive multifunctional fusion protein may be a protein or a polypeptide selected from proteins or polypeptides, capable to bind to its specific substrate or to the same or a different substrate binding peptide (SBP). In the context of the present invention, such a substrate binding peptide (SBP) may be selected from proteins or polypeptides, which interact with each other, e.g. via a specific substrate, or directly bind a specific substrate. Accordingly, when bound to a PEG-polymer, at least two such substrate binding peptides (SBP), optionally via a specific substrate, thus allow formation of an intricate molecular assembly or a sol-to-gel transition and hydrogel formation due to "cross-linking" the single PEG-polymer strains. Alternatively, hydrogel formation may be possible upon binding of a substrate binding peptide (SBP), which is already bound to a PEG-polymer, to its specific substrate, which is likewise bound to a further PEG-polymer. Accordingly, suitable substrate binding peptides (SBP) may be selected from peptides, which preferably have a tendency to form homo- or heteromultimers, e.g. homo- or heterodimers or even homo- or heterotrimers, etc. Alternatively, suitable substrate binding peptides (SBP) may be selected from proteins or polypeptides, which preferably bind specifically to a specific substrate. More preferably, in both cases the interaction of two or more substrate binding peptides (SBP) via a specific substrate or of a substrate binding peptide (SBP) to its specific substrate may be induced or dissolved again upon addition or removal (or replacement) of specific substrates. Such a specific substrate may be, e.g. a nucleic acid molecule, a peptide, a small organic molecule, etc, and is preferably specifically bound by the substrate binding peptides (SBP) as defined herein. Combinations of two or more substrate binding peptides (SBP), which have a tendency to form homo- or heteromultimers, either without or via binding to a specific substrate, or combinations of a substrate binding peptide (SBP) and their specific substrate, may be termed "binding partners" for the purposes of the present invention.

Accordingly, binding partners within the above meaning, wherein at least two or more substrate binding peptides (SBP) interact with each other, are preferably selected, without being limited thereto, from e.g. substrate binding peptide (SBP)-substrate binding peptide (SBP) combinations or from substrate binding peptide (SBP)-specific substrate combinations. Preferably, in both cases, the substrate binding peptide (SBP) represents a component of the inventive multifunctional fusion protein and confers its binding properties to the entire multifunctional fusion protein. Such substrate binding peptide (SBP)-substrate binding peptide (SBP) combinations or substrate binding peptide (SBP)-specific substrate combinations may be selected, without being limited thereto, from e.g. heparin binding protein (HBP)-heparin binding protein (HBP), heparin binding protein (HBP)-heparin, GyrB-GyrB (gyrase subunit B), FKBP-FRB (FK-binding protein-a domain (FRB) of the lipid kinase protein homologue FRAP (FKBP-rapamycin-associated protein)), $F_M$-$F_M$ (F36M mutation of FK-binding protein), ToxT-ToxT (ToxT Protein of $V.$ $cholerae$), DHFR-DHFR (dihydrofolate reductase), FKBP-FKBP (FK-binding protein), FKBP-Cyp (FK-binding protein-cyclophilin) and Cyp-Cyp (Cyclophilin). Such binding partners may be as well homomultimers or heteromultimers of at least two of the above-listed substrate binding peptides (SBP). The corresponding specific substrates may be selected, without being limited thereto, from e.g. heparin, coumarin antibiotics (for GyrB-GyrB), rapamycin or FK506 and derivatives (e.g. rapalogs, mTOR inhibitors) (for FKBP-FRB and $F_M$), cyclosporins and derivatives (for Cyp), FK506 (for FKBP-FRB and $F_M$), virtstatin (for ToxT), and methotrexate and derivatives thereof (e.g. antifolates) (for DHFR-DHFR) and/or from small organic compounds, for example compounds of a molecular weight between 100 and 5,000 g/mol, in particular between 100 and 2,000 g/mol.

According to a particular aspect, substrate binding peptides (SBP) may be selected from substrate binding peptides (SBP) having a tendency to form dimers. Particular examples of such substrate binding peptides (SBP), are preferably selected, without being limited thereto, from e.g. GyrB, $F_M$, ToxT, FKBP, and DHFR. Specific substrates, which allow inducing dimerization of these substrate binding peptides (SBP), may be selected, without being limited thereto, from coumarin antibiotics, rapamycin and derivatives, virstatin, FK1012, and methotrexate and derivatives thereof. These specific substrates may also be selected from compounds, which allow to induce and/or to dissolve the interaction between these substrate binding peptides (SBP) and thereby to neutralize the interaction between both binding partners as the neutralization may lead to substantial reduction of the interaction of both substrate binding peptides (SBP), e.g. in a competitive way. Such compounds are, for example, specific substrates as mentioned above when used in a substantial excess, or preferably other, different representatives of the same class of dimerizing compounds, e.g. the class of coumarin antibiotics, rapamycin and derivatives, and methotrexate, antifolates and derivatives thereof, and also FK506.

Binding partners of substrate binding peptides (SBP) as defined herein and nucleic acids as their specific substrates are for example, E-ETR (MphR(A) protein and its operator ETR of $E. coli$), PIP-PIR(PIP protein of $Streptomyces pristinaespiralis$ and its operator PIR), TetR-tetO (Tn10-derived tetracycline repressor TetR and its operator tetO), ArgR-argO (arginine-responsive repressor and its operator argO), ArsR-arsO (arsenic-responsive repressor and its operator arsO), and HucR-hucO (uric acid-responsive repressor and its operator hucO). Other such pairs are the ones described by Ramos J. L. et al. (Microbiol MoI Biol Rev 69, 326-56, 2005), Martinez-Bueno M. et al. (Bioinformatics 20, 2787-91, 2004), and the ones that are listed in the database BacT regulators (http://www.bactregulators.org/). These sequences are specifically incorporated herein by reference in their entirety. When utilizing such substrate binding peptides (SBP) as components of the inventive multifunctional fusion protein, the specific substrates are preferably bound to the PEG-polymer as used herein. Specific compounds suitable to dissolve the interaction and thus the inventive stimulus-responsive dissolvable PEG-hydrogel when utilizing such binding partners are, for example, macrolide antibiotics (for E-ETR), streptogramin antibiotics (for PIP-PIR), tetracycline antibiotics (for TetR-tetO), arginine (for ArgR-arsO), heavy metals (for ArsR-arsO), and uric acid (for HucR-hucO).

Binding partners of substrate binding peptides (SBP) as defined herein and small molecules as their specific substrates, are for example, GyrB-coumarin antibiotics, FKBP-mTOR inhibitors, FRB-mTOR inhibitors, $F_M$-mTOR inhibitors, Cyp-cyclosporins, Cyp-ascomycins, DHFR-antifolate, streptavidin-biotin analog, avidin-biotin analog, neutravidin-biotin analog, steroid hormone receptors-steroid hormones and analogs thereof, and ToxT-virstatin (in each case indicated as "substrate binding peptide-specific substrate"). In case that the specific substrate is a small molecule, the small molecule preferably has a molecular weight of preferably <5,000 g/mol, in particular between 100 and 5,000 g/mol. In this context, coumarin and aminocoumarin antibiotics may include, for example, novobiocin, chlorobiocin, coumermycin and dihydronovobiocin. A cyclosporin or an ascomycin can be, for example, Cyclosporin A (NEORAL(R)), ISAtx-247, FK506 (tacrolimus), FK778, ABT-281 or ASM981. An mTOR inhibitor can be, for example, rapamycin or a derivative thereof, e.g. Sirolimus (RAPAMUNE(R)), Deforolimus, Temsirolimus, Zotarolimus, Everolimus (Certican(R)), CCI779, ABT578, biolimus-7, biolimus-9, a rapalog, e.g.AP23573, azathioprine, campath 1 H, a S1 P receptor modulator, e.g. FTY720, or an analogue thereof. Rapalogs may include, among others, variants of rapamycin having one or more of the following modifications relative to rapamycin: demethylation, elimination or replacement of the methoxy group at C7, C42 and/or C29; elimination, derivatization or replacement of the hydroxy group at C13, C43 and/or C28; reduction, elimination or derivatization of the ketone function at C14, C24 and/or C30; replacement of the 6-membered pipecolate ring with a 5-membered prolinyl ring; and alternative substitution on the cyclohexyl ring or replacement of the cyclohexyl ring with a substituted cyclopentyl ring. Further modifications considered are presented in the background sections of U.S. Pat. Nos. 5,525,610; 5,310,903 and 5,362,718, and also in U.S. Pat. No. 5,527,907. Further considered is selective epimerization of the C28 hydroxy group (WO 01/14387). Further considered is the use of rapamycin analogs containing various phosphorus-containing moieties, such as described in WO 03/064383 and WO 05/16252. Other rapalogs considered are described in U.S. Pat. No. 6,984,635, U.S. Pat. No. 6,649,595 and U.S. Pat. No. 7,091,213. Antifolates may include, for example, compounds binding to DHFR like, for example, methotrexate, trimethoprim, diaminopyrimidines like brodimoprim and epiroprim, or iclaprim. Other DHFR inhibitors considered are those described in Hawser S. et al., Biochemical Pharmacology 71, 941-948, 2006. Finally, Biotin analogs may include, for example, compounds binding to streptavidin, neutravidin or avidin like, for example, biotin, HABA, desthiobiotin, iminobiotin or diaminobiotin. Preferably, the above-listed small molecules as specific substrates of substrate binding peptides (SBP) as defined herein may be subjected to derivatization suitable for binding same to the PEG polymer as used herein for the inventive stimulus-responsive dissolvable PEG-hydrogel. Such derivatization may include the introduction of an amine, an amide, a thiol, a hydroxyl, an aldehyde, an azide, an alkine, a ketone, an epoxide or a carboxy function into the specific substrate.

In the context of the present invention, particular preferred substrate binding peptides (SBP) and combinations thereof and their specific substrates are preferably selected from following combinations of substrate binding peptides (SBP) and their specific substrates: GyrB-GyrB and as their specific substrate aminocoumarin antibiotics (e.g. coumermycin, novobiocin, etc.), $F_M$-$F_M$ and FKBP-FRB and as their specific substrate rapamycin, FK506 and its derivatives AP21998 and AP22542, etc., more preferably when using the combinations GyrB-GyrB, $F_M$-$F_M$ and/or FKBP-FRB, most preferably GyrB-GyrB and/or $F_M$-According to a very specific alternative, the substrate binding peptide (SBP) as a component of the inventive multifunctional fusion protein of the present invention may be GyrB. In the context of the present invention, GyrB is preferably a protein derived from DNA gyrase subunit B from *Escherichia coli* and binds specifically to its substrates, preferably selected from aminocoumarin antibiotics including, for example, novobiocin, chlorobiocin, coumermycin and dihydronovobiocin, preferably coumermycin. Coumermycin is a long aminocoumarin molecule with two GyrB binding sites and finds use as an antibiotic. Its systematic IUPAC-name is [(3R,4S,5R)-5-Hydroxy-6-[2-hydroxy-3-[[4-[[2-hydroxy-7-[(3R,4S,5R)-3-hydroxy-5-methoxy-6,6-dimethyl-4-(5-methyl-1H-pyrrole-2-carbonypoxyoxan-2-yl]oxy-8-methyl-4-oxochro-men-3-yl]carbamoyl]-3-methyl-1H-pyrrole-2-carbonyl]amino]-8-methyl-4-oxochromen-7-yl]oxy-3-methoxy-2,2-dimethyloxan-4-yl] 5-methyl-1H-pyrrole-2-carboxylate. As coumermycin comprises two binding sites for GyrB, coumermycin allows dimerization of two GyrB subunits by simultaneously binding two GyrB subunits at the same time. This specific property can be utilized to cross-link two substrates coupled to a GyrB protein or peptide with each other utilizing the coumermycin dimerization of GyrB. The formed "dimer" can be dissolved again into its two monomeric GyrB subunits by adding e.g. the antibiotic novobiocin, a further aminocoumarin antibiotic, having the systematic IUPAC-name 4-hydroxy-3-[4-hydroxy-3-(3-methylbut-2-enyl)benzamido]-8-methylcoumarin-7-yl 3-O-carbamoyl-5,5-di-C-methyl-α-1-lyxofuranoside. Novobiocin comprises only one binding site for GyrB. Accordingly, the GyrB/coumermycin system may be used to effectively cross-link PEG polymers modified with the inventive multifunctional fusion protein containing GyrB subunits upon addition of coumermycin, resulting in gelation of the PEG-polymers and formation of a stimulus-responsive dissolvable PEG-hydrogel only on the basis of protein-substrate-protein interactions. Such a stimulus-responsive dissolvable PEG-hydrogel can also be specifically dissolved again when adding the antibiotic novobiocin, or other aminocoumarin antibiotics, since these aminocoumarin antibiotics specifically displace coumermycin in a competitive manner and thus interrupt the protein-substrate-protein interactions.

In the context of the present invention, GyrB as the substrate binding peptide (SBP) of the present invention, is selected from DNA gyrase subunit B from *Escherichia coli*, more preferably from the N-terminal sequence of DNA gyrase subunit B from *Escherichia coli*, even more preferably from the N-terminal sequence of DNA gyrase subunit B from *Escherichia coli* according to SEQ ID NO: 2 (see also FIG. 5), or an amino acid sequence showing at least 50, 60, 70, or 80%, preferably at least 90%, more preferably at least 95%, and even more preferably at least 97.5% identity to the sequence according to SEQ ID NO: 2, or may be encoded by a nucleic acid sequence according to SEQ ID NO: 1 (see also FIG. 5) or a nucleic acid sequence showing at least 50, 60, 70, or 80%, preferably at least 90%, more preferably at least 95%, and even more preferably at least 97.5% identity to the sequence according to SEQ ID NO: 1.

According to a further very specific alternative, the substrate binding peptide (SBP) of the present invention may be a heparin binding protein (HBP). Such a heparin binding protein may be selected from e.g. (human) heparin-binding growth factor 1 (HBGF-1), (human) heparin-binding growth factor 2 (HBGF-2), (human) heparin-binding growth factor 2 (HBGF-2, Genbank NM_002006), FGF4 (Genbank NM_002007), azurocidin (Genbank NM_001700) or cationic antimicrobial protein of 37 kDa (CAP37), etc. A heparin binding protein (HBP) as defined before is preferably part of the inventive multifunctional fusion protein and typically binds heparin as a substrate. A heparin binding protein (HBP) as defined before thus allows dimerization or even multimerization of two or more heparin binding proteins with one (or more) heparin molecule(s) as (a) substrate(s). Accordingly, such a heparin binding molecule, if contained in the inventive multifunctional fusion protein, may be used to effectively cross-link PEG polymers, modified with a fusion protein containing heparin binding proteins upon addition of heparin, resulting in gelation of the PEG-polymers and formation of a stimulus-responsive dissolvable PEG-hydrogel only on the basis of protein-substrate-protein interactions. Such a stimulus-responsive dissolvable PEG-hydrogel can also be specifically degraded again when adding a competing substrate, e.g. heparin in excess, i.e. in a sufficient amount to saturate each heparin binding site of a heparin binding protein. The stimulus-responsive dissolvable PEG-hydrogel can further be specifically dissolved, when adding a competing heparin binding protein, such as any of the above-mentioned heparin binding proteins or e.g. heparin binding protein receptor 2 (HBPR2), which specifically binds the heparin used for multimerization. When such a competitive substrate and/or a heparin binding protein is added, the protein-substrate-protein interactions are interrupted, and the gel will be degraded.

According to a further very specific alternative, the substrate binding peptide (SBP) of the present invention (and its respective substrate) may be selected from any member of the lipocalin family or from further suitable proteins binding a specific substrate, particularly from any of the proteins of the following protein/substrate combinations: FluA-fluorescein, DigA-Biotin-digoxin-conjugate, Salicylic Acid Binding Protein 2 (SABP2)-Salicylic Acid, or from proteins interacting with each other such as FKBP42 and PGP1, which further interact with Quercetin as a competitor. These protein/substrate combinations may be used to provide the inventive bio-functionalized stimulus-responsive dissolvable PEG-hydrogels, which can be formed and/or dissolved using stimuli that are licensed for human use and not harmful to the human organism.

The lipocalin family comprises more than 200 members (Darren R. Flower, "The lipocalin protein family: structure and function." The Biochemical journal 318 (1996) 1-14, which is incorporated herein by reference specifically with regard to members of the lipocalin protein family cited therein and sequences as defined in Darren R. Flower (1996), supra), prominent members of which are FluA and DigA. Most lipocalins are storage or transporter proteins for small insoluble or chemically sensitive organic compounds. The overall structure of the family members is highly conserved despite low sequence identity. However, a loop region, that forms the binding pocket varies significantly and can be further engineered to obtain substrate specificity for a certain ligand without affecting the overall protein structure (Steffen Schlehuber, "Anticalins: promising tools for clinical diagnostics." cli-online.com (2004)).

In the inventive context, FluA is preferably understood as an artificial lipocalin with a high substrate specificity towards fluorescein. Lipocalins usually serve as storage or transporter proteins of physiologically important compounds. The various members of the protein family all consist of 8 β-barrel-strands which are connected by a loop region. The loop region is very divers and forms the substrate binding pocket. FluA was engineered and improved by a combination of random and rational mutagenesis. Thus, the substrate affinity of the artificial FluA for fluorescein is 1 nM (Beste, G. Schmidt, F. S. Stibora, T.; Skerra, A. Proceedings of the National Academy of Sciences of the United States of America 1999, 96, 1898-903Beste et al. 1999; Vopel et. al. 2005; Vopel, S. Mühlbach, H.; Skerra, A. Biological chemistry 2005, 386, 1097-104). Pharmaceutically licensed polyethylene glycol polymer will be covalently grafted with FluA overexpressed in *E. coli* and labeled with fluorescein (see FIG. 25). The hydrogel formation is achieved by binding of FluA to the fluorescein label of another protein, preferably a fluorescein label which is bound by a further FluA molecule as defined herein. Addition of free fluorescein preferably results in a dose dependent dissolution of the hydrogel by competitive interaction with the binding site of FluA. Preferably, FluA is selected from an amino acid sequence according to SEQ ID NO: 55 (see also FIG. 18) or an amino acid sequence showing at least 50, 60, 70, or 80%, preferably at least 90%, more preferably at least 95%, and even more preferably at least 97.5% identity to the sequence according to SEQ ID NO: 54 or 55, or may be encoded by a nucleic acid sequence according to SEQ ID NO: 54 (see also FIG. 18) or a nucleic acid sequence showing at least 50, 60, 70, or 80%, preferably at least 90%, more preferably at least 95%, and even more preferably at least 97.5% identity to the sequence according to SEQ ID NO: 54.

Figure 26:
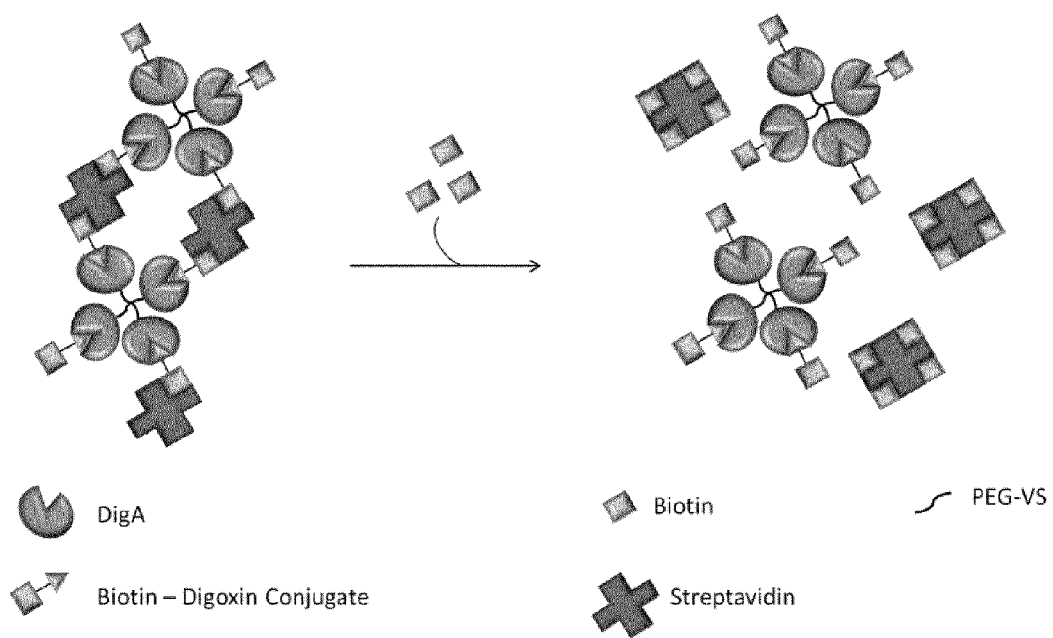

Furthermore, in the context of the present invention, DigA is preferably understood as an artificial lipocalin, which, however, comprises an engineered affinity towards digoxin. It was derived from the bilin-binding protein (BBP), a natural lipocalin from *Pieris brassicae* as was FluA. A substrate affinity of approximately 31 nM for digoxin could be achieved (Steffen Schlehuber, Gerald Beste, Ame Skerra. "A novel type of receptor protein, based on the lipocalin scaffold, with specificity for digoxigenin." Journal of Molecular Biology 297 (2000) 1105-20). FIG. 26 illustrates the formation and dissolution of the hydrogel. The basic mechanism is the same as described for FluA-fluorescein. Briefly, pharmaceutically licensed polyethylene glycol polymer will be covalently grafted with DigA. Hydrogel formation will be driven by addition of a biotin-digoxin-conjugate and streptavidin whereas DigA binds with high affinity to digoxin and streptavidin binds biotin. In the context of the present application, this construct is considered as a substrate binding peptide (SBP) (DigA) binding to its substrate (biotin-digoxin-conjugate and streptavidin). Dissolution can be achieved by addition of free biotin which will compete for the biotin binding sites. Biotin assists in various metabolic reactions and therefore high doses can be administered. Preferably, DigA is selected from a sequence according to SEQ ID NO: 57 (see also FIG. 19), or an amino acid sequence showing at least 50, 60, 70, or 80%, preferably at least 90%, more preferably at least 95%, and even more preferably at least 97.5% identity to the sequence according to SEQ ID NO: 57, or may be encoded by a nucleic acid sequence according to SEQ ID NO: 56 (see also FIG. 19) or a nucleic acid sequence showing at least 50, 60, 70, or 80%, preferably at least 90%, more preferably at least 95%, and even more preferably at least 97.5% identity to the sequence according to SEQ ID NO: 56.

Additionally, SABP2 belongs to the SABP2/SABP2-like family. This family includes several members that are not binding salicylic acid. Some display affinity towards stress-associated hormones like jasmonic acid or abscisic acid. In addition sequence analysis identified several plant hydroxynitrile lyases and lecithin (phosphatidylcholine) cholesterol acyl transferases from animals which are classified as SABP2L proteins.

Figure 27:
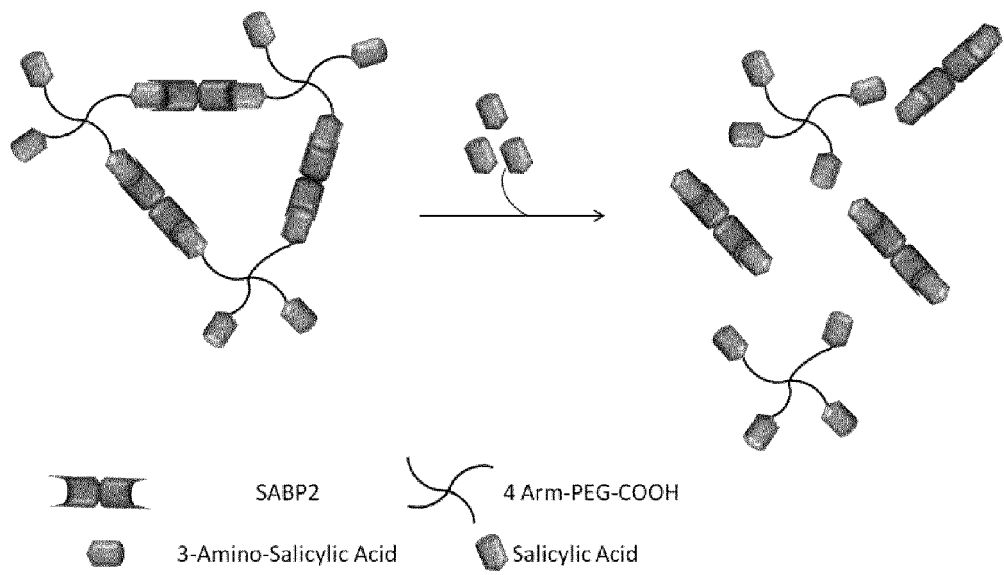

In the context of the present invention, the Salicylic Acid Binding Protein 2 (SABP2) is preferably derived from tobacco and plays an important role in the plants systemic acquired resistance (SAR) which is comparable to the immune response in animals. SAR provides long-lasting, broad spectrum resistance to microbial pathogens. SABP2 is a methyl salicylate (MeSA) esterase that has high affinity for salicylic acid (SA; $K_d$=90 nM), which acts as a feedback inhibitor of its esterase activity (Farhad Forouhar, Yang Yue, Dhirendra Kumar, Yang Chen, Eyal Fridman, Sang Wook Park, Yiwen Chiang, et al. "Structural and biochemical studies identify tobacco SABP2 as a methyl salicylate esterase and implicate it in plant innate immunity." Proceedings of the National Academy of Sciences of the United States of America 102 (2005) 1773-8). FIG. 27 illustrates how SABP2 is used for hydrogel formation. SABP2 is overexpressed in *E. coli* and purifies as a homodimer resulting in 2 SA binding sites per protein molecule (see Farhad Forouhar et al, 2005, supra). Pharmaceutically licensed polyethylene glycol polymer will be grafted with 3-amino-SA. Hydrogel formation is driven by binding of the pegylated 3-amino-SA at the active site. Addition of free SA displaces 3-amino-SA from the binding pocket and therefore results in dissolution of the hydrogel. SA can be administered to the patient in form of acetylsalicylic acid (Aspirin) since SA is the main metabolite of Aspirin. Up to 8 g of Aspirin per day can be taken. Preferably, SABP2 is selected from an amino acid sequence according to SEQ ID NO: 59 (see also FIG. 20), from an amino acid sequence according to SEQ ID NO: 61 (see also FIG. 21) or from an amino acid sequence showing at least 50, 60, 70, or 80%, preferably at least 90%, more preferably at least 95%, and even more preferably at least 97.5% identity to the sequence according to SEQ ID NO: 59 or 61, or may be encoded by a nucleic acid sequence according to SEQ ID NO: 58 (see also FIG. 20), a nucleic acid sequence according to SEQ ID NO: 60 (see also FIG. 21), or a nucleic acid sequence showing at least 50, 60, 70, or 80%, preferably at least 90%, more preferably at least 95%, and even more preferably at least 97.5% identity to the sequence according to SEQ ID NO: 58 or 60. SEQ ID NO: 61 (amino acid sequence) comprises an S81A mutation in the sequence according to SABP2 as defined before. SEQ ID NO: 60 is the encoding nucleic acid sequence.

Additionally, most of FKBP family members bind FK506 and exhibit peptidylprolyl cis/trans isomerase (PPIase) activity (Kang, Cong Bao, Ye Hong, Sirano Dhe-Paganon, Ho Sup Yoon. "FKBP family proteins: immunophilins with versatile biological functions." Neuro-Signals 16 (2008) 318-25). FKBP42 is a FK506 binding protein. PGP1 belongs to the family of multidrug-resistance proteins (MDRs) or P-glycoproteins, a subgroup of the full-size ABC transporters. ABC transporters implicated in detoxification and ion-regulation processes as well as plant growth processes (Enrico Martinoia, Markus Klein, Markus Geisler, Lucien Bovet, Cyrille Forestier, Üner Kolukisaoglu, Bernd Müller-Röber, Burkhard Schulz. "Multifunctionality of plant ABC transporters—more than just detoxifiers." Planta 214, (2002) 345-355).

In the context of the present invention the protein FKBP42 is preferably the *Arabidopsis* FK506 binding protein (FKBP42), which interacts with the C-terminal domain of *Arabidopsis* multidrugresistance-like ABC transporter AtPGP1. Both proteins are important for plant growth. For example, AtPGP1 is involved in auxin transport and auxin mediated development. It has been shown that the interaction is dependent on the primary amino acid sequence and glycosylation is not necessary (Rodolphe Bouchard, Karla Billion, Markus Geisler, Joachim Berger, Beate Saal, Nathalie Frangne, Zsuzsanna Koncz-ka, "TWISTED DWARF1, a Unique Plasma Membrane-anchored Immunophilin-like Protein, Interacts with *Arabidopsis* Multidrug Resistance-like Transporters AtPGP1 and AtPGP19." Molecular Biology of the Cell 14 (2003) 4238-4249). Furthermore, Bailly et. al. (Aurélien Bailly, Valpuri Sovero, Vincent Vincenzetti, Diana Santelia, Dirk Bartnik, Bernd W Koenig, Stefano Mancuso, Enrico Martinoia, and Markus Geisler. "Modulation of P-glycoproteins by auxin transport inhibitors is mediated by interaction with immunophilins." The Journal of biological chemistry 283 (2008) 21817-26) determined that the interaction can be disrupted by the flavonoid quercetin with an IC50 of ~200 nM. Hydrogel formation is achieved by attachment of FKBP42 and AtPGP1 to a pharmaceutically licensed polyethylene glycol polymer (see FIG. 28). Addition of quercetin disrupts the protein-protein interactions and thereby dissolves the hydrogel. Quercetin is an antioxidant and appears to have many beneficial effects on human health. An oral dose of 400-500 mg three times per day is typically used in clinical practice (Gideon Rodan, "Mechanisms of Action of Bisphosphonates." Annual Review of Pharmacology and Toxicology 38 (1998) 375-388). Preferably, FKBP42 is encoded by the nucleic acid sequence according to SEQ ID NO: 62 (see also FIG. 22) or is selected from an amino acid sequence encoded thereby, or from a nucleic acid sequence showing at least 50, 60, 70, or 80%, preferably at least 90%, more preferably at least 95%, and even more preferably at least 97.5% identity to the nucleic acid sequence according to SEQ ID NO: 62, or an amino acid sequence encoded thereby, or may be selected from an amino acid sequence according to SEQ ID NO: 64 (see also FIG. 22), or from an amino acid sequence showing at least 50, 60, 70, or 80%, preferably at least 90%, more preferably at least 95%, and even more preferably at least 97.5% identity to the amino acid sequence according to SEQ ID NO: 64, or may be encoded by a nucleic acid sequence according to SEQ ID NO: 63 (see also FIG. 22), or a nucleic acid sequence showing at least 50, 60, 70, or 80%, preferably at least 90%, more preferably at least 95%, and even more preferably at least 97.5% identity to the sequence according to SEQ ID NO: 63. SEQ ID NO: 64 (amino acid sequence) comprises aa 1-163 of the encoded aa sequence according to SEQ ID NO: 62 as defined before. SEQ ID NO: 63 is corresponding the encoding nucleic acid sequence.

Likewise preferably, AtPGP1 is selected from an amino acid sequence according to SEQ ID NO: 66 (see also FIG. 23), from an amino acid sequence according to SEQ ID NO: 68 (see also FIG. 24) or from an amino acid sequence showing at least 50, 60, 70, or 80%, preferably at least 90%, more preferably at least 95%, and even more preferably at least 97.5% identity to the sequence according to SEQ ID NO: 66 or 68, or may be encoded by a nucleic acid sequence according to SEQ ID NO: 65 (see also FIG. 23), a nucleic acid sequence according to SEQ ID NO: 67 (see also FIG. 24), or a nucleic acid sequence showing at least 50, 60, 70, or 80%, preferably at least 90%, more preferably at least 95%, and even more preferably at least 97.5% identity to the sequence according to SEQ ID NO: 65 or 67. SEQ ID NO: 68 (amino acid sequence) comprises aa 980-1286 of the amino acid sequence according to SEQ ID NO: 66 as defined before. SEQ ID NO: 67 is corresponding the encoding nucleic acid sequence.

Both AtPGP1 and FKBP42 may be used as a substrate binding protein (SBP) or as a substrate in the context of the present invention. Precisely, FKBP42 may be used as a substrate binding protein (SBP) in the context of the present invention and AtPGP1 may be used as substrate with this substrate binding protein (SBP). Alternatively, AtPGP1 may be used as a substrate binding protein (SBP) in the context of the present invention and FKBP42 may be used as substrate with this substrate binding protein (SBP). Addition of quercetin disrupts the protein-protein interactions and thereby dissolves the hydrogel. In either case, the protein used as a substrate is preferably provided as a dimer, wherein such a dimer may be provided by linking two such proteins with a linker, preferably with a linker as provided herein, more preferably a peptidic linker, or by suitably cross-linking these proteins using chemical cross-linkers. For the purpose of preparation of such proteins, these dimers may be prepared either after preparation of the monomeric proteins, e.g. subsequent to expression of the monomeric (single chain) proteins e.g. via bacterial expression, or via expression of the dimeric proteins with an encoded peptidic linker (located between two encoded substrate proteins within one reading frame) e.g. via bacterial expression, or by dimerizing or cross-linking the monomeric proteins, e.g. using chemical cross-linking methods or peptidic linkers. Peptidic linkers are preferably selected from a short linker peptide of four, five, five to ten or ten to about 25 amino acids. The linker is usually rich in glycine for flexibility, as well as serine or threonine for solubility, and may be positioned at any suitable position, preferably either the N-terminus or the C-terminus of a monomeric protein to be used in this context. Alternatively, such a linker may be a PEG as defined herein, either a multi-arm PEG as defined herein or a non-branched PEG, preferably selected from a PEG as defined herein.

These proteins, particularly lipocalins, FluA, DigA, SABP2, AtPGP1 and FKBP42, are preferably merely representatives of their corresponding protein families, preferably of the family of lipocalins, the SABP2/SABP2-like family, the FKBP family, etc. Hence, suitable substrate binding proteins (or, if applicable, suitable substrates) in the context of the present invention may furthermore comprise further members of said protein families. Such further members of these protein families preferably comprise homologs of these proteins, such as (other) plant homologs, and preferably homologs exhibiting a sequence identity to any of these more specifically identified proteins lipocalins, FluA, DigA, SABP2, AtPGP1 and FKBP42, in a range as defined above. Hence, in the respective hydrogel setups the proteins can be substituted by such other members of the family and their individual binding partners.

According to a further preferred aspect, the substrate binding peptide (SBP) of the inventive multifunctional fusion protein may be an antibody fragment, preferably a single chain variable fragment (scFv) of an antibody, preferably capable of binding a substrate, which may be furthermore bound by a further single chain variable fragment (scFv) of an antibody of the same type. In this context, a single chain variable fragment (scFv) of an antibody is preferably a fusion protein of the variable regions of the heavy ($V_H$) and light chains ($V_L$) of immunoglobulins, connected with a short linker peptide of four, five, five to ten or ten to about 25 amino acids. The linker is usually rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. Particularly preferred single chain variable fragments (scFv's) in the context of the present invention may comprise a specificity against a contrast agent, typically used in medicine, more preferably used in diagnostic medicine, etc. A particularly preferred contrast agent in this context is, inter alia, fluorescein, a fluorescein derivative, FITC (fluoresceinisothiocyanate), or a derivative thereof, etc. which may then be used as a substrate of a corresponding substrate binding peptide a(SBP) as defined herein, particularly of single chain variable fragments (scFv's) having such a specifity. An exemplary single chain variable fragment (scFv) may be e.g. an scFv against fluorescein named FITC-E2 as published in Vaughan et al. 1996 (see Vaughan et al., (1996), *Nat. Biotechnol* 14 (3), S. 309-314). Such an scFv may be recombinantly produced as a C-terminal hexahistidine tagged version in established expression systems as described for example by Pedrazzi et al., (1997), *FEBS Lett* 415 (3), S. 289-293), which shows an expression in the periplasm of *E. coli*, or by Rippmann et al., (1998), *Appl. Environ. Microbiol.* 64 (12), S. 4862-4869), which shows an expression in L-form cells of *Proteus mirabilis*. Expression in either *E. coli* or *Proteus mirabilis* is particularly preferred. A preferable protein sequence may be the amino acid sequence of the produced scFv as shown in FIG. 33 (SEQ ID NO: 69) (sequence depicted after removal of the periplasmic signal sequence), or an amino acid sequence showing at least 50, 60, 70, or 80%, preferably at least 90%, more preferably at least 95%, and even more preferably at least 97.5% identity to the sequence according to SEQ ID NO: 69.

Furthermore, the substrate bound by such a substrate binding protein and correspondingly by such a multifunctional fusion protein comprising the specific scFv fragment (acting as an SBP as defined before) may be e.g. fluorescein, FITC, or derivatives thereof. This substrate may furthermore be bound to bovine serum albumine (BSA) or amine-modified multi-arm-PEG derivatives. Any such substrate or substrate construct may then be used in the formation of an inventive bio-functionalized stimulus-responsive dissolvable PEG-hydrogel. The substrate or substrate constructs may be indicated as BSA-fluorescein, BSA-FITC, PEG-fluorescein, PEG-FITC, etc., which then act as a crosslinking agent within the inventive concept brought into contact with the PEG coupled inventive multifunctional fusion protein. As a polymer, preferably a multi-arm-PEG-VS is used, which can be functionalized with a scFv or a corresponding multifunctional fusion protein as defined herein, e.g. harboring a cysteine (e.g. at the C-terminus, as shown for the GyrB hydrogel).

The scFv of the inventive multifunctional fusion protein can furthermore be directly modified with fluorescein, FITC, or a derivative thereof, so that it can cross-link itself. Alternatively or additionally, growth factors as defined herein may be utilized to form a fusion protein with the scFv within the multifunctional fusion protein. Such growth factors may be incorporated into the fusion protein as defined herein.

Other examples of suitable proteins similar to scFvs for the inventive multifunctional fusion protein may include camel/shark antibodies, AdNectins, protein Z domains (see herein), darpins, anticalins, etc.

The multifunctional fusion protein used to modify the PEG-polymers of the inventive stimulus-responsive dissolvable PEG-hydrogel may furthermore comprise a repetitive RGD-binding peptide, preferably having the formula ($RGD_n$), also defined as $RGD_n$ or $(RGD)_n$. Typically, such a repetitive RGD-binding peptide of formula ($RGD_n$), also defined as $RGD_n$ or $(RGD)_n$, of the multifunctional fusion protein may be a peptide containing at least one RGD-peptide sequence, preferably at least two RGD-peptide sequences, or even three, four five or more RGD-peptide sequences, i.e. n may be 1, 2, 3, 4, 5 or even more, preferably, n is 1 to 5, 1 to 4, 1 to 3, 2 to 5, 2 to 4, 2 or 3 or 3 to 5, 3 to 4 or 4 to 5. In this context, a RGD peptide sequence is typically a sequence containing the three (consecutive) amino acids RGD, which is the one-letter amino acid code abbreviation for "Arginine-Glycine-Aspartate", in preferably the indicated order. The number of repetitions is preferably determined by the integer n as defined above. Such a RGD sequence typically represents a part of the recognition sequence for integrins to extracellular matrix proteins. In this context, integrins are known as receptors that mediate attachment between a cell and the tissues surrounding it, e.g. other cells or the extracellular matrix (ECM). Integrins also play a role in cell signaling and thereby define cellular shape, mobility, and regulate the cell cycle. RGD-sequences, which may be utilized for the inventive purpose to allow binding of a cell to the multivalent fusion protein via integrins, are typically derived from an ECM protein or peptide comprising an RGD peptide sequence, or a synthetic sequence, in each case comprising the amino acid sequence Arginine-Glycine-Aspartate ("RGD" in the one-letter amino acid code). Such cell-specific adhesion sequences which might be incorporated into the inventive multifunctional fusion protein are e.g. as reviewed and listed by Hersel et al. (2003) (see Hersel et al., Biomaterials 24 (2003), 4385-4415). The respective disclosure in Hersel et al. (2003, supra) directed to such specific RGD peptide sequences and the specific RGD sequences as disclosed therein are preferably incorporated herein in their entirety by reference. Even more preferably, such RGD sequences may be selected, without being limited thereto, from at least one of the following amino acid sequences:

RGD (or RGD$_n$ or (RGD)$_n$) (SEQ ID NO: 3), RGDS (SEQ ID NO: 4), (RGDS)$_n$ (SEQ ID NO: 5), wherein n is preferably 1, 2, 3, 4, 5, 6, 7, 8, 9, 10 or even more, GRGD (SEQ ID NO: 6), RGDV (SEQ ID NO: 7), RGDT (SEQ ID NO: 8), GRGDG (SEQ ID NO: 9), GRGDS (SEQ ID NO: 10), GRGDY (SEQ ID NO: 11), GRGDF (SEQ ID NO: 12), YRGDS (SEQ ID NO: 13), YRGDG (SEQ ID NO: 14), YGRGD (SEQ ID NO: 15), GRGDSP (SEQ ID NO: 16), GRGDSG (SEQ ID NO: 17), GRGDSP (SEQ ID NO: 18), GRGDSY (SEQ ID NO: 19), GRGDVY (SEQ ID NO: 20), GRGDSPK (SEQ ID NO: 21), CGRGDSPK (SEQ ID NO: 22), CGRGDSY (SEQ ID NO: 23), YAVTGRGDS (SEQ ID NO: 24) (RGD mimetic tyrosine scaffold), AcCG-GNGEPRGD (SEQ ID NO: 25), YRAY-NH$_2$ (SEQ ID NO: 26), AcGCGYGRGDSPG (SEQ ID NO: 27), RGDSPASSKP (SEQ ID NO: 28), AcGRGDSPASSKG (SEQ ID NO: 29), or may be selected from cyclic RGD-sequences, such as e.g. βAXEPRGDNYRC (SEQ ID NO: 30), wherein X represents the modified amino acid Dap (2,3-diamino propionic acid), βA represents b-alanine and this cyclic RGD-sequence has the following structure:

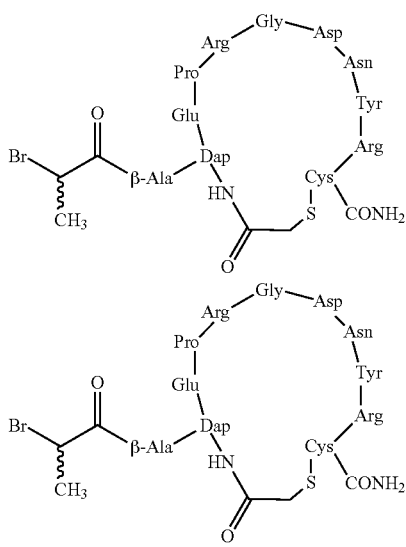

KRGDf (SEQ ID NO: 31), wherein f represents the D-amino acid variant of phenylalanine, and wherein this cyclic RGD-sequence has the following structure:

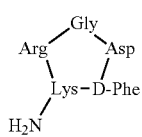

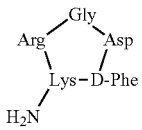

GPenGRGDSPCA (SEQ ID NO: 32), wherein Pen represents Penicillin, and wherein this cyclic RGD-sequence has the following structure:

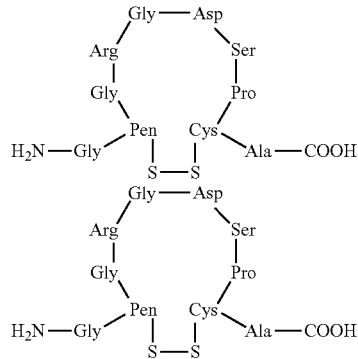

vRGDE (SEQ ID NO: 33), wherein v represents the D-amino acid variant of valine, and wherein this cyclic RGD-sequence has the following structure:

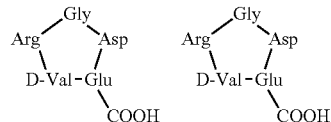

or may be selected from an amino acid sequence showing at least 80%, preferably at least 90%, more preferably at least 95%, and even more preferably at least 97.5% identity to the sequence of any of SEQ ID NO's 3 to 33.

The inventive multifunctional fusion proteins used to modify the PEG-polymers of the inventive stimulus-responsive dissolvable PEG-hydrogel may furthermore comprise at least one N- and/or C-terminal linker. Accordingly, the linker may be located at the N-terminal end, at the C-terminal end or at the N- and the C-terminal end of the inventive multifunctional fusion protein. Such an N- and/or C-terminal linker may be used to bind the inventive multifunctional fusion protein to a PEG-polymer as defined herein (or (additionally) to a further component as defined herein) by a covalent or a (strong, specific and) non-covalent bond. A (strong and specific) non-covalent bond in the sense of the present invention is a bond with a dissociation constant of below $10^5$ M under physiological conditions. Suitable linkers in the context of the present invention preferably include or contain, for example, chelate-forming entities like NTA and polyhistidine binding to a multivalent metal ion, amino acids, a thiol-containing moiety, such as e.g. a thiol-modified or a thiol-containing amino acid, a cysteine, a homocysteine, any further thiol-containing moiety, a thiol coupled to maleimide, a vinylsulfone-moiety, peptide sequences, peptide bonds, a halotag (Los G. V. et al., Methods Mol Biol. 356, 195-208, 2007), a SNAP-tag or a CLIP-tag (Gautier A. et al., Chem. Biol. 15, 128-36, 2008) or a transglutaminase reaction bond (see Ehrbar M. et al., Biomaterials 29, 1720-9, 2008). For this purpose, the PEG polymer as employed according to the present invention has preferably been correspondingly modified prior to introducing the inventive multifunctional fusion protein, to allow covalent or non-covalent binding of such a linker to the inventive multifunctional fusion protein.

In the case, that the inventive multifunctional fusion protein comprises only one linker, e.g. at the N- or the C-terminal end of the inventive multifunctional fusion protein, the linker is preferably used to covalently bind the multifunctional fusion protein according to the present invention to the PEG polymer, preferably via a covalent bond. In the case, that the inventive multifunctional fusion protein used to modify the PEG-polymers of the inventive stimulus-responsive dissolvable PEG-hydrogel comprises two linkers, e.g. at the N- and the C-terminal end of the inventive multifunctional fusion protein, the first linker is preferably used to covalently bind the multifunctional fusion protein according to the present invention to the PEG polymer, preferably via a covalent bond, and the second linker is preferably used to covalently bind a further component to the inventive multifunctional fusion protein, preferably via a covalent bond.

According to a very specific aspect the linker of the inventive multifunctional fusion protein is selected from or contains a thiol-containing moiety, such as e.g. a thiol-modified or a thiol-containing amino acid, a cysteine, a homocysteine, any further thiol-containing moiety, a thiol coupled to maleimide, a vinylsulfone-moiety, etc. When using a thiol-containing moiety, binding preferably to the PEG-polymer or a further component occurs covalently and preferably via a thioether bond. For this purpose, e.g. the PEG polymer as employed according to the present invention (or a further component) has preferably been correspondingly modified prior to introducing the inventive multifunctional fusion protein, to allow covalent binding of the thiol-containing moiety to a corresponding reactive group of the inventive multifunctional fusion protein, e.g. via a thioether bond. The at least one N- and/or C-terminal thiol-containing moiety may also be used to covalently bind a further component to the inventive multifunctional fusion protein, e.g. via a thioether bond. In the case, that the inventive multifunctional fusion protein comprises only one thiol-containing moiety, e.g. a Cysteine moiety, the thiol-containing moiety is preferably used to covalently bind the multifunctional fusion protein according to the present invention to the PEG polymer via a thioether bond. In the case, that the inventive multifunctional fusion protein used to modify the PEG-polymers of the inventive stimulus-responsive dissolvable PEG-hydrogel comprises two thiol-containing moieties, i.e. at the N- and the C-terminal end of the inventive multifunctional fusion protein, the first thiol-containing moiety is preferably used to covalently bind the multifunctional fusion protein, according to the present invention to the PEG polymer via a thioether bond, and the second thiol-containing moiety is preferably used to covalently bind a further component to the inventive multifunctional fusion protein via a thioether bond. In this context, such a further component may be either a cell as defined herein, a protein as defined herein, a fusion protein as defined herein, a further PEG-polymer as defined herein, or any other component as defined herein, wherein the further component has preferably been correspondingly modified prior to preparing such a linkage to allow covalent binding to the thiol-containing-moiety of the inventive multifunctional fusion protein, e.g. via a thioether bond.

According to a further specific aspect the linker of the inventive multifunctional fusion protein may be selected from or contains a covalent linker as defined in the following table. Preferably, linkers may be selected from one or more of an e.g. amine, thiol containing moiety (e.g. thiols, cysteines), lysine, glutamine, N-terminal cysteine, amine, amine, or a carboxyl group, etc. For such a purpose, the PEG polymer is preferably accordingly modified, e.g. in the case of amines e.g. by N-hydroxylsuccinimide (NHS), in the case of thiol containing moieties (e.g. thiols, cysteines) e.g. with maleimide or vinylsulfone, as described before, in the case of lysine e.g. with glutamine, glutamine, in the case of glutamine e.g. with lysine, in the case of N-terminal cysteine e.g. with a thioester, in the case of amine e.g. with an aldehyde, in the case of a carboxyl group e.g. with an amine, etc. In this context, the covalent attachment may be carried out using any chemistry known by a scientist skilled in the art such as overviewed e.g. in Lottspeich and Engels 2006, chapter 6.1 and 6.3.1 (see Lottspeich, Friedrich; Engels, Joachim W. (2006): Bioanalytik. 2. Aufl. München, Heidelberg: Elsevier, Spektrum, Akad. Verl.).

Without being limited thereto, particular examples of linkers and the preferred functionalization of the PEG-polymers as defined herein are listed in the following table:

| Linker/Fusion Protein functionalization | PEG-polymer functionalization | Type of reaction |
|---|---|---|
| amines | N-hydroxylsuccinimide (NHS) | Reacts with amine groups of proteins resulting in stable amide bonds |
| Thiol (e.g. cysteines) | maleimideMaleimide | |
| Thiol (e.g. cysteines) | Vinylsulfone (VS) | Michael-type addition, formation of a stable thioether bond |
| Lysine | Glutamine | Transglutaminase reaction |
| Glutamine | Lysine | Transglutaminase reaction |
| N-terminal cysteine | Thioester | Native chemical ligation |
| Amine | Aldehyde | Schiff base reaction |
| Amine | Carboxyl group | Reaction mediated by EDC (1-ethyl-3-(3-dimethylaminopropyl) carbodiimide), amide bond formed |
| Carboxyl group | Amine | Reaction mediated by EDC (1-ethyl-3-(3-dimethylaminopropyl) carbodiimide), amide bond formed |

The inventive multifunctional fusion protein may also contain a tag for purification (purification tag or tag), i.e. a stretch of amino acids added to the inventive multifunctional fusion protein, which enables the recovery of the fusion protein by its unique affinity. Preferably, the purification tag is added either at the N- or the C-terminus of the fusion protein or peptide (or close thereto, e.g. as a second component of the fusion peptide when determined from either the N- or C-terminal end) to ensure its accessibility and not to disturb the protein folding of the different components of the fusion protein or peptide. Purification tags within the context of the present invention comprise e.g. a $His_6$-tag, a FLAG-tag, a HA-tag, a MYC tag, etc. In this context, a His tag is preferably a tag consisting of 6 histidine (His) residues ($His_6$-tag), which allows the inventive multifunctional fusion protein to be recovered by affinity to nickel or cobalt column. A FLAG tag preferably comprises e.g. the sequence DYKDDDDK (SEQ ID NO: 34) or a further sequence and allows recovery of the inventive multifunctional fusion protein with a specific antibody. An HA tag within the context of the present invention is typically a fusion with an epitope derived from the Influenza protein haemagglutinin (HA): e.g. YPYDVP (SEQ ID NO: 35) and allows recovery with an HA antibody. Finally a MYC tag is usually a fusion with an epitope derived from the human proto-oncoprotein MYC: e.g. ILKKATAYIL (SEQ ID NO: 36), EQKLISEEDL (SEQ ID NO: 37) and allows recovery with an MYC antibody. Further purification tags are known to a skilled person and may be adapted and used as suitable in the context of the inventive multifunctional fusion protein.

The multifunctional fusion protein used to modify the PEG-polymers of the inventive stimulus-responsive dissolvable PEG-hydrogel may also comprise a further binding domain, e.g. a ZZ domain, which allows binding of a $F_c$-domain and thus conjugating a further (peptide or protein) component to the ZZ domain via an $F_c$-domain. Such a ZZ-domain, suitable for the present inventive purpose, may be selected from a ZZ domain as e.g. defined in vector pEZZ-18, GE healthcare, or as defined in Ishikawa-Sakurai et al. (2004) (see Ishikawa-Sakurai et al., Human Molecular Genetics, 2004, Vol. 13, No. 7 693-702), preferably a sequence according to AKHQAKCNICKECPIIGFRYRSLKHFNYDICQSCFFSGR (SEQ ID NO: 38), or a sequence according to AKHQAKCNICKECPIVGFRYRSLKHFNYDVCQSCFFSGR (SEQ ID NO: 39), displaying the ZZ-domains of dystrophin (SEQ ID NO: 38) and utrophin (SEQ ID NO: 39), or a sequence according to (M)AQHDEAVDNKFNKEQQNAFYEILHLPNLNEEQRNAFIQSLKDDPSQSANLL AEAKKLNDAQAPKVDNKFNKEQQNAFYEILHLPNLNEEQRNAFIQSLKDDPSQSANLLAE AKKLNDAQAPKVDANSS (SEQ ID NO: 40 (see also amino acids 1 or 2 to 129 of FIG. 7)), or an amino acid sequence showing at least 80%, preferably at least 90%, more preferably at least 95%, and even more preferably at least 97.5% identity to the sequence of any of SEQ ID NO's 38 to 40.

Binding the inventive multifunctional fusion protein as defined according to the present invention (and optionally a specific substrate or any further compound) to a PEG-polymer as defined herein, e.g. via a linker as defined above, may occur by mixing the components and preferably varying the concentration of the components to be bound in the ranges as defined herein. This preferably allows the components to interact with each other and thereby forming a bond.

Additional to such linkers as defined above, which are suitable to bind the inventive multifunctional fusion protein, optionally a specific substrate or any further compound to a PEG-polymer and thereby cross-link the polymers to form a PEG-hydrogel, further (cross-)linkers can be introduced into the inventive stimulus-responsive PEG-hydrogel, into the PEG polymers used therefore or into the multifunctional fusion protein as defined according to the present invention.

This may allow for further (chemical) cross-linking the inventive stimulus-responsive PEG-hydrogel. Suitable cross-linkers are e.g. any homo- or heterofunctional compounds showing at least two sites for binding to another molecule like the ones described in Bioconjugate Techniques ($2^{nd}$ Edition by Greg T. Hermanson, Academic Press, 2008).

The components of the inventive multifunctional fusion protein used to modify the PEG-polymers may be located at every position of the fusion protein, when determined with respect to the N- and/or C-terminal end of the inventive multifunctional fusion protein. However, it is preferred that the inventive multifunctional fusion protein is composed to allow for both, effective multimerization of substrate binding peptides (SBP) due to interaction with their specific substrate, or binding of the substrate binding peptide (SBP) to its specific substrate, and in parallel the effective binding of cells. Furthermore, it shall allow optionally binding of further molecules, e.g. via further binding sequences.

Accordingly, the inventive multifunctional fusion protein may contain, without being limited thereto, the substrate binding peptide (SBP), a repetitive RGD-binding peptide as defined above and at least one N- and/or C-terminal linker, e.g. in at least one of the following orders (from N- to C-terminus (defined as N- or -C)):

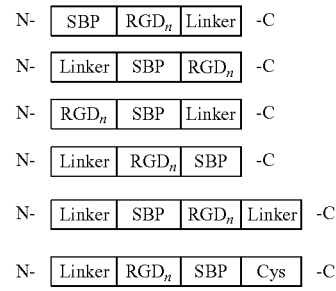

etc.

Furthermore, the inventive multifunctional fusion protein may contain, without being limited thereto, the substrate binding peptide (SBP), a repetitive RGD-binding peptide and at least one N- and/or C-terminal linker and a tag for purification, e.g. in at least one of the following orders (from N- to C-terminus (defined as N- or -C)):

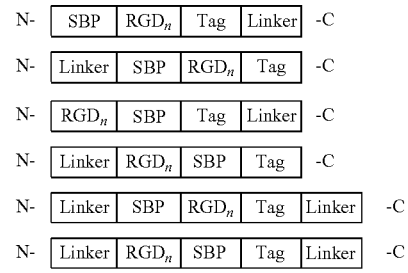

etc.

The inventive multifunctional fusion protein may also contain, without being limited thereto, the substrate binding peptide (SBP), a repetitive RGD-binding peptide and at least one N- and/or C-terminal linker, a ZZ binding domain as defined herein and optionally a tag for purification, e.g. in at least one of the following orders (from N- to C-terminus (defined as N- or -C)):

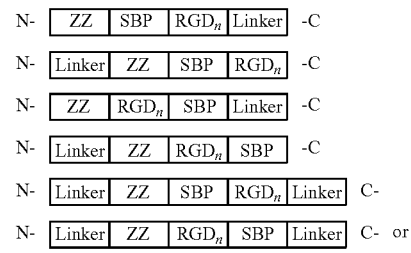

-continued

N- | ZZ | SBP | RGD$_n$ | Tag | Linker | C-

N- | Linker | ZZ | SBP | RGD$_n$ | Tag | C-

N- | ZZ | RGD$_n$ | SBP | Tag | Linker | C-

N- | Linker | ZZ | RGD$_n$ | SBP | Tag | C-

N- | Linker | ZZ | SBP | RGD$_n$ | Tag | Linker | -C

N- | Linker | ZZ | RGD$_n$ | SBP | Tag | Linker | -C or

N- | ZZ | Tag | SBP | RGD$_n$ | Linker | C-

N- | Linker | ZZ | Tag | SBP | RGD$_n$ | C-

N- | ZZ | Tag | RGD$_n$ | SBP | Linker | C-

N- | Linker | ZZ | Tag | RGD$_n$ | SBP | C-

N- | Linker | ZZ | Tag | SBP | RGD$_n$ | Linker | -C

N- | Linker | ZZ | Tag | RGD$_n$ | SBP | Linker | -C etc.

Additionally or alternatively, the at least one multifunctional fusion protein used to modify the PEG-polymers may comprise as components a substrate binding peptide (SBP) as defined above, preferably a ZZ domain as defined above, preferably a tag for purification as defined above and at least one N- and/or C-terminal linker. Accordingly, the inventive multifunctional fusion protein may contain, without being limited thereto, as components a substrate binding peptide (SBP) as defined above, preferably a ZZ domain as defined above, preferably a tag for purification as defined above and at least one N- and/or C-terminal linker, e.g. in at least one of the following orders (from N- to C-terminus (defined as N- or -C)):

N- | ZZ | SBP | Linker | -C

N- | Linker | ZZ | SBP | -C

N- | SBP | ZZ | Linker | -C

N- | Linker | SBP | ZZ | -C

N- | Linker | ZZ | SBP | Linker | -C

N- | Linker | SBP | ZZ | Linker | -C

N- | ZZ | SBP | Tag | Linker | -C

N- | Linker | ZZ | SBP | Tag | -C

N- | SBP | ZZ | Tag | Linker | -C

N- | Linker | SBP | ZZ | Tag | -C

N- | Linker | ZZ | SBP | Tag | Linker | C-

N- | Linker | SBP | ZZ | Tag | Linker | C- etc.

Likewise additionally, the PEG polymer as defined herein may be modified using at least one multifunctional fusion protein comprising as components preferably a ZZ domain as defined above, preferably a tag for purification as defined above and at least one N- and/or C-terminal linker. Accordingly, the inventive multifunctional fusion protein may contain, without being limited thereto, as components a ZZ domain as defined above, preferably a tag for purification as defined above and at least one N- and/or C-terminal linker, e.g. in at least one of the following orders (from N- to C-terminus (defined as N- or -C)):

N- | ZZ | Linker | -C

N- | Linker | ZZ | -C

N- | Linker | ZZ | Linker | -C

N- | ZZ | Tag | Linker | -C

N- | Linker | ZZ | Tag | -C

N- | Linker | ZZ | Tag | Linker | -C etc.

The different components of the at least one multifunctional fusion protein as defined according to the present invention are preferably directly linked with each other or via a spacer. If the different components of the multifunctional fusion protein are linked via a spacer, the spacer is preferably a peptidic spacer. A peptidic spacer typically has a length of 1 to 20, preferably 1 to 10 amino acids, more preferably 1 to 5, even more preferably 1 to 3 amino acids. In some cases the peptidic spacer sequence may be even longer, comprising 21 to 50 amino acids. A peptidic spacer may be composed of various amino acid sequences. Accordingly, such a peptidic spacer is preferably inserted via peptide bonds between at least two components of the multifunctional fusion protein as defined according to the present invention, more preferably between three, four or even five or all components of the multifunctional fusion protein, as defined according to the present invention. Preferably, a peptidic spacer will introduce some structural flexibility between the single components of the multifunctional fusion protein to be linked. Introducing such a spacer, structural flexibility is achieved, e.g. by having a peptidic spacer containing various glycine or proline residues and optionally serine residues, preferably at least 30%, more preferably at least 40% and even more preferably at least 60, 70, 75, 80, 85, 90 or even 95 or 100% proline and/or glycine residues within the peptidic spacer sequence and optionally 1 to 10, 1 to 20, 1 to 30 or 1 to 40% serine residues within the peptidic spacer sequence, e.g. a spacer showing a sequence e.g. according to (SGGG)$_n$ (SEQ ID NO: 41), (SGGGG)$_n$ (SEQ ID NO: 42), or (SGGGGG)$_n$ (SEQ ID NO: 43), wherein n is preferably 1, 2, 3, 4, 5, etc. Furthermore, such a spacer may provide a sufficient distance to the other components of the multifunctional fusion protein, if required. Irrespective from its structure (peptidic spacer), the spacer preferably may be immunologically inactive. Appropriate spacers can be easily selected and prepared by a person skilled in the art.

Particularly preferred inventive multifunctional fusion proteins as defined herein may be selected from multifunctional fusion proteins according to pRG 107 (coding nucleic acid sequence: SEQ ID NO: 44, protein sequence: SEQ ID NO: 45), pRG111 (coding nucleic acid sequence: SEQ ID NO: 46, protein sequence: SEQ ID NO: 47) or pRG116 (coding nucleic acid sequence: SEQ ID NO: 48, protein sequence: SEQ ID NO: 49) or an amino acid sequence showing at least 80%, preferably at least 90%, more preferably at least 95%, and even more preferably at least 97.5% identity to the sequence of any of SEQ ID NO's 45, 47 or 49, or as encoded by a nucleic acid sequence showing at least 80%, preferably at least 90%, more preferably at least 95%, and even more preferably at least 97.5% identity to the sequence of any of SEQ ID NO's 44, 46 or 48 (see also FIGS. 6, 7 and 8).

In order to determine the percentage to which two peptide or protein sequences as defined herein, are identical, the sequences can be aligned in order to be subsequently compared to one another. Therefore, e.g. gaps can be inserted into the sequence of the first sequence and the component at the corresponding position of the second sequence can be compared. If a position in the first sequence is occupied by the same component as is the case at a position in the second sequence, the two sequences are identical at this position. The percentage to which two sequences are identical is a function of the number of identical positions divided by the total number of positions. The percentage to which two sequences are identical can be determined using a mathematical algorithm. A preferred, but not limiting, example of a mathematical algorithm which can be used is the algorithm of Karlin et al. (1993), PNAS USA, 90:5873-5877 or Altschul et al. (1997), Nucleic Acids Res., 25:3389-3402. Such an algorithm is integrated in the BLAST program. Sequences which are identical to the sequences as described in the present invention to a certain extent can be identified by this program. The same applies analogously to nucleic acid sequences.

The present invention also provides nucleic acid sequences encoding a multifunctional fusion protein, as defined above, vector sequences, in particular expression vectors, and cells, transfected with such nucleic acid sequences. The nucleic acid sequences may be DNA, RNA, single-stranded, double-stranded, circular and/or linear.

The inventive multifunctional fusion proteins may be prepared using e.g. synthetic methods, bacterial expression methods, typically using expression vectors or expression plasmids, commonly known in the art and encoding the multifunctional fusion protein or sequences thereof, or using any further method known to a skilled person. Specifically preferred multifunctional fusion proteins in the context of the present invention which may be used for hydrogel formation will be typically expressed in bacterial expression systems such as *E. coli*, in *Proteus mirabilis*, etc.

Any of the above defined alternatives of the inventive multifunctional fusion protein may be used to modify the PEG-polymers and to form the inventive stimulus-responsive dissolvable PEG-hydrogel, e.g. a multifunctional fusion protein, comprising as components a substrate binding peptide (SBP), preferably a repetitive RGD-binding peptide, such as $(RGD_n)$ or $RGD_n$ or $(RGD)_n$, and/or a ZZ-binding domain, preferably a tag for purification, and at least one N- and/or C-terminal Cysteine moiety, or a multifunctional fusion protein, comprising as components a substrate binding peptide (SBP) as defined above, preferably a ZZ domain as defined above, preferably a tag for purification as defined above and at least one N- and/or C-terminal Cysteine moiety as defined above, etc.

Depending on the type and/or the amount of different multifunctional fusion proteins, as defined according to the present invention, more precisely on the number of the specific linkers contained in each of the different multifunctional fusion proteins, the degree of cross-linking of the inventive stimulus-responsive dissolvable PEG-hydrogel may be influenced. Additionally, the content of further components in the inventive stimulus-responsive dissolvable PEG-hydrogel, the content of e.g. components, such as cells binding to an RGD-sequence as defined herein within the inventive multifunctional fusion protein, or binding of further components, such as a further component (peptide or protein) to the ZZ domain via its $F_c$-domain, may be modified accordingly.

Particularly preferred as an inventive multifunctional fusion protein to modify the degree of cross-linking of the inventive stimulus-responsive dissolvable PEG-hydrogel are multifunctional fusion proteins as defined above and even more preferably as selected from the following:

a) multifunctional fusion proteins as defined herein, having only one linker as defined above;

b) multifunctional fusion proteins as defined herein, having two linkers as defined above;

c) a combination of multifunctional fusion proteins as defined herein, having only one linker as defined above, and of multifunctional fusion proteins as defined herein, having two linkers as defined above.

Particularly preferred are further inventive stimulus-responsive dissolvable PEG-hydrogel comprising inventive multifunctional fusion protein as defined before.

Highly preferred in this context is a combination of multifunctional fusion proteins as defined herein, having only one linker as defined above, and multifunctional fusion proteins as defined herein, having two linkers as defined above, even though multifunctional fusion proteins as defined herein, having only one linker as defined above, and multifunctional fusion proteins as defined herein, having two linkers may be used alone.

Preferably, multifunctional fusion proteins as defined in option c) may be selected from any of the above-mentioned multifunctional fusion proteins, more preferably from a mixture or combination of multifunctional fusion proteins as defined herein, having only one linker as defined above, and containing a substrate binding protein (SBP), an RGD-sequence, such as $(RGD_n)$ or $RGD_n$ or $(RGD)_n$, optionally a tag for purification and an N- or C-terminal linker, and such multifunctional fusion proteins as defined herein, having two linkers as defined above, and containing a substrate binding protein (SBP), an RGD-sequence, such as $(RGD_n)$ or $RGD_n$ or $(RGD)_n$, optionally a tag for purification and an N-terminal and a C-terminal linker.

In this context, exemplary multifunctional fusion proteins as defined herein having only one linker as defined above may be selected, without being limited thereto, from at least one of the following:

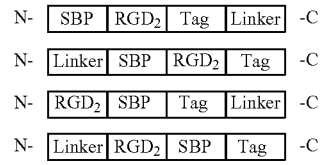

more preferably selected from

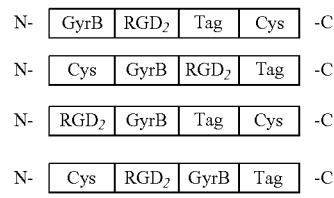

or from

N- | Cys | Tag | RGD$_2$ | FKBP42 | -C

N- | Cys | Tag | FKBP42 | RGD$_2$ | -C

N- | Cys | Tag | RGD$_2$ | pgp1 | -C

N- | Cys | Tag | pgp1 | RGD$_2$ | -C

N- | SABP2 | RGD$_2$ | Tag | -C

N- | RGD$_2$ | SABP2 | Tag | -C

N- | FluA | RGD$_2$ | Tag | Cys | -C

N- | RGD$_2$ | FluA | Tag | Cys | -C

N- | DigA | RGD$_2$ | Tag | Cys | -C

N- | RGD$_2$ | DigA | Tag | Cys | -C

Furthermore, exemplary multifunctional fusion proteins as defined herein having two linkers as defined above may be selected, without being limited thereto, from one of the following:

| | | | | | | |
|---|---|---|---|---|---|---|
| N- | Linker | SBP | $RGD_2$ | Tag | Linker | -C |
| N- | Linker | $RGD_2$ | SBP | Tag | Linker | -C | more preferably from

| | | | | | | |
|---|---|---|---|---|---|---|
| N- | Cys | GyrB | $RGD_2$ | Tag | Cys | -C |
| N- | Cys | $RGD_2$ | GyrB | Tag | Cys | -C | or from

| | | | | | | |
|---|---|---|---|---|---|---|
| N- | Cys | Tag | $RGD_2$ | FKBP42 | Cys | -C |
| N- | Cys | Tag | FKBP42 | $RGD_2$ | Cys | -C |
| N- | Cys | Tag | $RGD_2$ | pgp1 | Cys | -C |
| N- | Cys | Tag | pgp1 | $RGD_2$ | Cys | -C |
| N- | Cys | FluA | $RGD_2$ | Tag | Cys | -C |
| N- | Cys | $RGD_2$ | FluA | Tag | Cys | -C |
| N- | Cys | DigA | $RGD_2$ | Tag | Cys | -C |
| N- | Cys | $RGD_2$ | DigA | Tag | Cys | -C |

In any of the herein defined exemplary multifunctional fusion proteins the position of the N-terminus and position of the C-terminus may be exchanged for each other, i.e. wherein order of the components of an exemplary multifunctional fusion protein has been reversed. Additionally, in any of these exemplary multifunctional fusion proteins the RGD domain could also be replaced by a ZZ-domain.

The inventive stimulus-responsive dissolvable PEG-hydrogel according to the present invention preferably comprises a matrix of PEG-polymers, which are modified to contain at least one multifunctional fusion protein as defined above. As defined herein, PEG is defined as polyethylene glycol (PEG), a polyether compound with many applications from industrial manufacturing to medicine. PEG is also known as polyethylene oxide (PEO) or polyoxyethylene (POE), preferably depending on its molecular weight. PEG, PEO, or POE are sometimes used synonymously and refer to an oligomer or polymer of ethylene oxide. The three names are chemically synonymous, even though historically PEG has tended to refer to oligomers and polymers with a molecular mass below 20,000 g/mol, PEO to polymers with a molecular mass above 20,000 g/mol, and POE to a polymer of any molecular mass. PEG and PEO are typically liquids or low-melting solids, depending on their molecular weights. PEGs are prepared by polymerization of ethylene oxide and are commercially available over a wide range of molecular weights from 300 g/mol to 10,000,000 g/mol. While PEG and PEO with different molecular weights find use in different applications and have different physical properties, e.g., viscosity, due to chain length effects, their chemical properties are nearly identical. Different forms of PEG are also available, dependent on the initiator used for the polymerization process, the most common of which is a monofunctional methyl ether PEG (methoxypoly(ethylene glycol)), abbreviated mPEG. Lower-molecular-weight PEGs are also available as pure oligomers, referred to as monodisperse, uniform or discrete. PEGs are also available with different geometries. Branched or Star PEGs have about 3-100 PEG chains (arms) emanating from a central core group. Comb PEGs have multiple PEG chains, normally grafted to a polymer backbone. Any such PEG-polymers may be utilized in the inventive stimulus-responsive dissolvable PEG-hydrogel as defined above. In the context of the present invention, the term "PEG" or "PEG-polymers" preferably comprises any of the above defined polymers, more preferably PEG, PEO and POE polymers as defined before.

Hence, in the context of the present invention, PEG-polymers for use in the inventive stimulus-responsive dissolvable PEG-hydrogel as defined above may be preferably selected from PEG polymers, PEO polymers and/or POE polymers as defined above, preferably within a molecular weight of about 300 g/mol to 10,000,000 g/mol, more preferably within a molecular weight of about 300-50,000 Da, even more preferably within a molecular weight of about 300-38,000 Da, etc., most preferably within a molecular weight of about 10 to about 50 kDa, e.g. within a molecular weight of about 20 to about 40 kDa, within a molecular weight of about 30 to about 40 kDa, e.g. within a molecular weight of about 35 to about 40 kDa, e.g. 37.5 kDa. More preferably, PEG-polymers for use in the inventive stimulus-responsive dissolvable PEG-hydrogel as defined above may be selected from any PEG-polymer as defined above, and preferably having different geometries, such as branched PEGs, e.g. having about 3 to 10 PEG chains emanating from a central core group, or e.g. having Star-PEGs have about 10-100 PEG chains emanating from a central core group as defined herein. Even more preferably, PEG-polymers for use in the inventive stimulus-responsive dissolvable PEG-hydrogel as defined above may be selected from any such PEG-polymer as defined herein, more preferably from PEG-polymers, having a molecular weight as defined above, and preferably, having different geometries as defined herein, such as Star-PEGs, e.g. having about 3 to about 100 PEG chains (arms) emanating from a central core group, preferably having about 3 to about 50, 3 to about 30, or 3 to about 20 PEG chains (arms), emanating from a central core group. Star-PEGs, being particularly preferred for use in the inventive stimulus-responsive dissolvable PEG-hydrogel as defined above may be a PEG polymer as defined above, having 3, 4, 5, 6, 7, 8, 9, 10, 11, 12, 13, 14, or 15 or more chains (arms) emanating from a central core group, i.e. being a 3, 4, 5, 6, 7, 8, 9, 10, 11, 12, 13, 14, or 15-armed Star-PEG-polymer. Such PEG-polymers are also referred to as multiarm Star-PEGs, e.g. 3 to 15 multiarm Star-PEGs.

In the context of the present invention, PEG-polymers for use in the inventive stimulus-responsive dissolvable PEG-hydrogel as defined above may be modified to allow a covalent or non-covalent bond to the inventive multifunctional fusion protein as defined herein. Such a covalent or non-covalent bond is preferably as defined above. In a preferred case, such a bond is a covalent bond. More preferably, such a bond is a thioether bond. Such a thioether bond may be formed by reaction of a SH- or Thiol-containing moiety of the inventive multifunctional fusion protein as defined above, e.g. of a Cysteine, with a vinylsulfone moiety, or any further moiety, which allows formation of a thioether bond. For this purpose, the SH- or Thiol-containing moiety of the inventive multifunctional fusion protein as defined above has been reduced prior to reaction with the vinylsulfone moiety or the further moiety using a reducing agent, preferably TCEP. This step prevents the thiol moiety to react to a disulfide bond and allows formation of a thioether bond. In this context, the PEG-polymers for use in the inventive stimulus-responsive dissolvable PEG-hydrogel preferably provide at least one free vinylsulfone moiety for the thioether bond or any further moiety, which allows formation of a thioether bond. Accordingly, the inventive stimulus-responsive dissolvable PEG-hydrogel may be modified prior to cross-linking to introduce such a modification. Modification may e.g. start from a PEG-OH polymer of a PEG polymer as defined above, preferably from a multiarm Star-PEGs as defined above. An exemplary modification reaction is shown in the following:

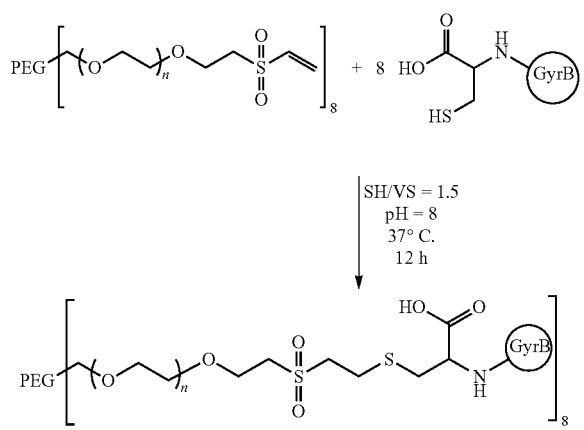

According to one specific aspect, such a modification may occur by sulfonating PEG-OH polymer of a PEG polymer as defined above, preferably a multiarm Star-PEG as defined above, typically leading to a Star-PEG-vinylsulfone (PEG-VS). According to a very specific protocol, a multiarm Star-PEG-vinylsulfone (PEG-VS) may be synthesized according to Lutolf et al. (2003) (see Lutolf M P, Hubbell J A., 2003, Synthesis and physicochemical characterization of end-linked poly(ethylene glycol)-co-peptide hydrogels formed by Michael-type addition. Bio-macromolecules 4(3):713-22) starting from 8-arm PEG-OH (Shearwater polymers, Huntsville, Ala.): Multiarm PEG-VSs may be synthesized e.g. by coupling PEG-OHs with an excess of divinyl sulfone (Aldrich, Buchs, Switzerland). As an example, PEG-OH may be dissolved in a solvent, e.g. dichloromethane or, in some cases PEG may be dried by azeotropic distillation, e.g. in toluene, e.g. using a Dean Stark trap before starting the reaction. To the PEG dissolved in dichloromethane, NaOH may be added, preferably under argon, preferably with a molar excess over OH groups, e.g. 4 to 6-fold, e.g. 5-fold. After hydrogen evolution, divinylsulfone may be added then at molar excess over OH groups, preferably at 50- to 100-fold. The reaction is typically carried out at room temperature, preferably for 1 to 3 days, e.g. 2 to 3 or even 3 days, preferably under argon atmosphere with constant stirring. Afterwards the reaction solution is typically neutralized, preferably with concentrated acid, e.g. acetic acid, filtered and reduced to a small volume. PEG may then be precipitated by adding the remaining solution into ice-cold diethyl ether. The polymer may then be recovered by filtration, washed with e.g. diethyl ether, and dried, preferably under vacuum. The dry polymer may then be dissolved in deionized water, containing sodium chloride and extracted dichloromethane. This solution may be dried with sodium carbonate and the volume may be reduced by evaporation. Finally, the product may be reprecipitated and washed, e.g. with diethyl ether, to remove all remaining divinyl sulfone. The final product may be dried under vacuum and stored under inert gas, e.g. argon, preferably at 20° C. Derivatization may be confirmed with $^1$H NMR (CDCl$_3$). The degree of end group conversion, as shown by NMR, is preferably in a range from 90 to 99%, more preferably in a range from 95 to 98%. Gel permeation chromatography may furthermore be used to confirm that the starting material (PEG-OH) and the end-functionalized PEG-VS have identical molecular weight distributions.

Further chemical compounds may also be attached to PEG polymers as defined herein by any bond as indicated above or any other possible chemical attachment, e.g. by amide formation (e.g. carboxylic acids, sulphonic acids, amines, etc.), by Michael addition (e.g maleinimide moieties, unsaturated carbonyls, etc.), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow Sn-type substitution reactions (e.g halogenalkans, thiols, alcohols, amines, hydrazines, hydrazides, sulphonic acid esters, oxyphosphonium salts), or other chemical moieties which can be utilized in the attachment of further components. Such other possible chemical attachments may also be used to covalently bind further components as defined herein, such as the inventive multifunctional fusion protein, further components, cells, etc. to PEG polymers as defined herein.

In the context of the present invention, the PEG-polymers for use in the inventive stimulus-responsive dissolvable PEG-hydrogel as defined above may also be modified to allow a covalent bond to the inventive multifunctional fusion protein as defined herein via any of the modifications, selected from, without being limited thereto, modifications described above in the context of a linker of the inventive multifunctional fusion proteins and their indicated PEG modifications/functionalizations. Such PEG modifications/functionalizations may include, e.g. a functionalization with N-hydroxylsuccinimide (NHS), preferably with a linker comprising an amine, wherein the N-hydroxylsuccinimide (NHS) typically reacts with amine groups of the proteins and results in stable amide bonds; a functionalization with maleimide, preferably with a linker comprising thiol (e.g. cysteines) as described before; a functionalization with vinylsulfone (VS), preferably with a linker comprising thiol (e.g. cysteines), wherein the vinylsulfone typically reacts in a Michael-type addition with the thiol under formation of a stable thioether bond; a functionalization with glutamine, preferably with a linker comprising lysine, wherein the reaction is typically a transglutaminase reaction; a functionalization with lysine, preferably with a linker comprising glutamine, wherein the reaction is typically a transglutaminase reaction; a functionalization with thioester, preferably with a linker comprising N-terminal cysteine, wherein the reaction is typically a native chemical ligation; a functionalization with aldehyde, preferably with a linker comprising amine, wherein the reaction is typically a Schiff base reaction; a functionalization with carboxyl group, preferably with a linker comprising amine, wherein the reaction is typically mediated by EDC (1-ethyl-3-(3-dimethylaminopropyl) carbodiimide) and an amide bond is formed; a functionalization with amine, preferably with a linker comprising arboxyl group, wherein the reaction is typically a reaction mediated by EDC (1-ethyl-3-(3-dimethylaminopropyl)carbodiimide) and an amide bond is formed; etc.

In the case the inventive multifunctional fusion protein or the resulting inventive bio-functionalized stimulus-responsive dissolvable PEG-hydrogel comprises an scFv fragment as a substrate binding protein, the resulting inventive bio-functionalized stimulus-responsive dissolvable PEG-hydrogel may be further modified, e.g. via incorporation of growth factors as defined herein or other (therapeutic) molecules/proteins as defined herein, preferably by one of the following ways: physical entrapment, functionalization of the molecules with FITC and mixing into the hydrogel, Fc-tagged molecules mediated by a ZZ domain as defined herein, coupling of growth factors to the hydrogel via the same chemistry or linkers as the scFv, and/or formation of a fusion protein with the scFv. Such a hydrogel may be furthermore modified by addition of any small-molecule-, peptide- or protein target of choice by selecting for an scFv binding to the respective molecule and immobilizing the target molecule on a polymer similar as carried out for fluorescein or FITC, e.g. crosslinking may be mediated by a biotin-binding scFv and a biotin-modified polymer (e.g. biotin-multiarm-PEG).

The object underlying the present invention is furthermore solved by a method for preparing the inventive stimulus-responsive dissolvable PEG-hydrogel, preferably a stimulus-responsive dissolvable PEG-hydrogel as defined above. Typically, the inventive stimulus-responsive dissolvable PEG-hydrogel, comprising a matrix of PEG-polymers as defined above, may be prepared according to the following steps:
a) providing at least one multifunctional fusion protein as defined herein
b) mixing the at least one multifunctional fusion protein according to step a) with a substrate for the substrate binding protein (SBP) as defined above;
c) adding the mixture obtained according to step b) to a PEG-polymer as defined herein; and thereby preferably forming the PEG-hydrogel.

In step a) of the method for preparation of the inventive stimulus-responsive dissolvable PEG-hydrogel at least one multifunctional fusion protein is provided. As already discussed above, the degree of cross-linking of the inventive stimulus-responsive dissolvable PEG-hydrogel may be influenced by selectively using a specific type and/or amount of different multifunctional fusion proteins as defined according to the present invention, more precisely by using multifunctional fusion proteins as defined herein, having only one or two linkers as defined herein, e.g. one or two thiol-containing moieties, cysteines or homocysteines. As can be easily understood, multifunctional fusion proteins as defined herein, having only one linker usually will lead to a different type of cross-linking than multifunctional fusion proteins as defined herein, having two linkers.

Accordingly, in step a) of the method for preparation of the inventive stimulus-responsive dissolvable PEG-hydrogel different inventive multifunctional fusion proteins as defined herein may be provided, not only to introduce different functionalities but also preferably to modify the type and degree of cross-linking of the inventive stimulus-responsive dissolvable PEG-hydrogel. Accordingly, in step a) of the method for preparation of the inventive stimulus-responsive dissolvable PEG-hydrogel, preferably
a) multifunctional fusion proteins as defined herein, having only one linker as defined above;
b) multifunctional fusion proteins as defined herein, having two linkers as defined above; and/or
c) multifunctional fusion proteins as defined herein, having only one linker as defined above, and multifunctional fusion proteins as defined herein, having two linkers as defined above, may be used. Highly preferred is option c), i.e. a mixture or combination of multifunctional fusion proteins as defined herein having only one linker as defined above and multifunctional fusion proteins as defined herein, having two linkers as defined above.

In this context, without being limited thereto, exemplary multifunctional fusion proteins as defined herein for step a) of the method for preparation of the inventive stimulus-responsive dissolvable PEG-hydrogel, having only one linker as defined above may be most preferably selected e.g. from the following:

N- | SBP | RGD$_2$ | Tag | Cys | -C
N- | Cys | SBP | RGD$_2$ | Tag | -C
N- | RGD$_2$ | SBP | Tag | Cys | -C
N- | Cys | RGD$_2$ | SBP | Tag | -C
N- | GyrB | RGD$_2$ | Tag | Cys | -C
N- | Cys | GyrB | RGD$_2$ | Tag | -C
N- | RGD$_2$ | GyrB | Tag | Cys | -C
N- | Cys | RGD$_2$ | GyrB | Tag | -C

Furthermore, without being limited thereto, exemplary multifunctional fusion proteins as defined herein for step a) of the method for preparation of the inventive stimulus-responsive dissolvable PEG-hydrogel, having two linkers as defined above may be most preferably selected from the following:

N- | Cys | SBP | RGD$_2$ | Tag | Cys | -C
N- | Cys | RGD$_2$ | SBP | Tag | Cys | -C
N- | Cys | GyrB | RGD$_2$ | Tag | Cys | -C
N- | Cys | RGD$_2$ | GyrB | Tag | Cys | -C

Preferably, the molar ratio of multifunctional fusion proteins, having only one linker to multifunctional fusion proteins, having two linkers, as may be used in step a) of the inventive method, is preferably about 20 to about 1, about 10 to about 1, about 5 to about 1, about 4 to about 1, about 3 to about 1, about 2 to about 1, about 1 to about 1, about 1 to about 2, about 1 to about 3, about 1 to about 4, about 1 to about 5, about 1 to about 10 or even about 1 to about 20. More preferably, the molar ratio of multifunctional fusion proteins, having only one linker to multifunctional fusion proteins, having two linkers is about 10 to about 1, about 5 to about 1, about 4 to about 1, about 3 to about 1, about 2 to about 1 or about 1 to about 1, most preferably about 5 to about 1.

Furthermore, protein end concentrations (preferably in solution prior to hydrogel formation) of these multifunctional fusion protein(s) to be provided in step a) of the method for preparation of the inventive stimulus-responsive dissolvable PEG-hydrogel may be, without being limited thereto, in a range of about 1 to about 500 µg/µl, in a range of about 10 to about 300 µg/µl, in a range of about 20 to about 250 µg/µl, in a range of about 30 to about 200 µg/µl, in a range of about 40 to about 175 µg/µl, in a range of about 50 to about 150 µg/µl, more preferably in a range of about 60 to about 140 µg/µl, in a range of about 70 to about 130 µg/µl, in a range of about 80 to about 120 µg/µl, or in a range of about 90 to about 110 µg/µl.

Additional to the degree of cross-linking the content of further components in the inventive stimulus-responsive dissolvable PEG-hydrogel, such as cells binding to an RGD-sequence as defined herein within the inventive multifunctional fusion protein or of further peptide or protein components, e.g. binding to the ZZ domain via an $F_c$-domain, may be modified accordingly. Thus, it may be also preferred to additionally introduce such inventive multifunctional fusion proteins comprising a ZZ domain as defined above into the inventive PEG hydrogel.

Accordingly, in step a) of the method for preparation of the inventive stimulus-responsive dissolvable PEG-hydrogel such inventive multifunctional fusion proteins may be provided in addition, which contain a ZZ domain as defined herein. Generally, any multifunctional fusion proteins containing a ZZ domain as defined herein may be used for this purpose. In this context, without being limited thereto, exemplary multifunctional fusion proteins as defined herein for step a) of the method for preparation of the inventive stimulus-responsive dissolvable PEG-hydrogel containing a ZZ domain may be most preferably selected from one of the following:

N- | ZZ | GyrB | Cys | -C
N- | Cys | ZZ | GyrB | -C
N- | GyrB | ZZ | Cys | -C
N- | Cys | GyrB | ZZ | -C
N- | Cys | ZZ | GyrB | Cys | -C
N- | Cys | GyrB | ZZ | Cys | -C
N- | ZZ | GyrB | Tag | Cys | -C
N- | Cys | ZZ | GyrB | Tag | -C
N- | GyrB | ZZ | Tag | Cys | -C
N- | Cys | GyrB | ZZ | Tag | -C
N- | Cys | ZZ | GyrB | Tag | Cys | -C
N- | Cys | GyrB | ZZ | Tag | Cys | -C

If inventive multifunctional fusion proteins comprising a ZZ domain as defined above are incorporated into the inventive PEG-hydrogel, protein end concentrations of (all) multifunctional fusion protein(s) to be provided in step a) of the inventive method for preparation of the inventive stimulus-responsive dissolvable PEG-hydrogel may be in about the same range as already defined above. However, it may be preferable to determine protein end concentrations of inventive multifunctional fusion proteins comprising a ZZ domain separately, e.g., without being limited thereto, in a range of about 0.001 to about 100 µg/µl, in a range of about 0.001 to about 50 µg/µl, in a range of about 0.001 to about 25 µg/µl, in a range of about 0.001 to about 20 µg/µl, in a range of about 0.001 to about 10 µg/µl, in a range of about 0.001 to about 5 µg/µl, more preferably in a range of about 0.01 to about 2.5 µg/µl, or in a range of about 0.1 to about 2 µg/µl.

Depending on the type and/or the amount of different multifunctional fusion proteins as defined according to the present invention, more precisely on the number of the specific linkers contained in different multifunctional fusion proteins, the degree of cross-linking of the inventive stimulus-responsive dissolvable PEG-hydrogel may be influenced. Additionally, the content of further components in the inventive stimulus-responsive dissolvable PEG-hydrogel, the content of e.g. components, such as cells binding to an RGD-sequence as defined herein within the inventive multifunctional fusion protein, or binding of further components, such as a further peptide or protein component to the ZZ domain via its $F_c$-domain, may be modified accordingly.

In step b) of the inventive method for preparation of the inventive stimulus-responsive dissolvable PEG-hydrogel the at least one multifunctional fusion protein, as provided according to step a) and a substrate, as defined above for the substrate binding protein (SBP) are mixed with each other.

The specific substrate for the substrate binding protein (SBP) as defined above may be any suitable substrate as defined herein, which can be bound by at least one, preferably by at least two substrate binding proteins (SBP) as defined above, to allow dimerization or multimerization of the covalently bound PEG polymers or just specific binding of the substrate by the substrate binding protein (SBP). For example, a specific substrate for the substrate binding protein GyrB as defined above is the antibiotic coumermycin, which can be bound by (one or) two GyrB subunits. Furthermore, a heparin binding protein (HBP), as defined above may bind heparin as its substrate, wherein preferably at least one, preferably at least two heparin binding proteins (HBP) may bind to the same substrate. Likewise, any further substrate binding protein (SBP) as defined above may be used. Accordingly, it may be necessary in step b) of the inventive method for preparation of the inventive stimulus-responsive dissolvable PEG-hydrogel, to use the substrate binding protein (SBP) in equal or even double molar excess or even a higher molar excess with respect to its substrate. In other words, the molar ratio between heparin binding protein (HBP) and its substrate is preferably about 1:1 or 2:1 or even more. As a particular example, the molar ratio between a GyrB containing multifunctional fusion protein to be used and its substrate coumermycin is preferably about 2:1. Likewise, the molar ratio between a heparin binding protein (HBP) containing multifunctional fusion protein to be used and its substrate is preferably about 2:1 or even 1:1.

The mixture obtained in step b) is preferably incubated after mixing, to allow thorough mixing and preferably interaction of the components of the mixture. In particular, incubation may allow binding of the substrate binding protein (SBP) to its specific substrate, e.g. to allow binding of one or two or more multifunctional fusion proteins, each containing a GyrB subunit to its specific substrate, the antibiotic coumermycin, or e.g. to allow binding of one or two multifunctional fusion proteins, each containing a heparin binding protein to its specific substrate heparin.

In step c) of the method for preparation of the inventive stimulus-responsive dissolvable PEG-hydrogel the mixture as provided in step b), i.e. of at least one multifunctional fusion protein as defined herein and of a substrate as defined above for the substrate binding protein (SBP), is preferably added to a PEG-polymer as defined herein, either simultaneously or in a staggered manner at different points of time, e.g. first the at least one multifunctional fusion protein as defined herein and then a substrate as defined above for the substrate binding protein (SBP), or vice versa. Adding of the mixture as provided in step b) to a PEG-polymer as defined herein, is typically carried out in a temperature range of about 15° C. to about 50° C., more preferably in a temperature range of about 15° C. to about 40° C., e.g. at about room temperature (RT, e.g. about 20 to 25° C., e.g. 20° C. or 25° C.), or at about 37° C. As already defined above, the PEG-polymer may be modified to comprise a thiol-containing moiety or any further moiety, which allows formation of a thioether bond, e.g. vinylsulfone moieties, or may be modified to comprise any further functionalization to bind a linker as defined herein.

The molar ratio of the multifunctional fusion protein as defined herein (containing the substrate binding protein (SBP)) to the reactive (thioether-forming or further functionalizations for linker) moieties of the PEG polymer as provided in step c) of the inventive method is preferably about 1:1, e.g. between about 0.75:1 and about 1:0.75, between about 0.8:1 and about 1:0.8, between about 0.85:1 and about 1:0.85, between about 0.9:1 and about 1:0.9, between about 0.95:1 and about 1:0.95, or about 1:1. Preferably, the concentration of the PEG polymer might be between 0.5-15%, e.g. between about 0.5 to about 5%, between about 2.5 to about 7.5%, between about 5 to about 10%, between about 7.5 to about 12.5%, or between about 10 to about 15%, either w/v or v/v or w/w. or may be in a range formed by any two of these values.

Hydrogel formation according to step c) of the inventive method for preparing the inventive stimulus-responsive dissolvable PEG-hydrogels is preferably carried out in a humidified atmosphere, to prevent drying and thus shrinking of the newly formed PEG-hydrogel.

According to a very preferred alternative of the inventive method, the inventive stimulus-responsive dissolvable PEG-hydrogels may be prepared by providing at least one inventive multifunctional fusion protein, e.g. in a first step a) of the inventive method. The at least one inventive multifunctional fusion protein preferably comprises one inventive multifunctional fusion protein as defined above with one linker and preferably a further inventive multifunctional fusion protein, comprising two linkers as defined above, typically in a molar amount of about 10 to about 1, about 5 to about 1, about 4 to about 1, about 3 to about 1, about 2 to about 1, about 1 to about 1, e.g. about 5 to about 1, preferably at a protein end concentration in a range of about 60 to about 140 µg/µl, in a range of about 70 to about 130 µg/µl, in a range of about 80 to about 120 µg/µl, or in a range of about 90 to about 110 µg/µl, e.g. about 100 µg/µl. For further modification, a multifunctional fusion protein containing a ZZ domain as defined herein may be added during step a) in an end concentration in a range of about 0.001 to about 10 µg/µl, in a range of about 0.001 to about 5 µg/µl, more preferably in a range of about 0.01 to about 2.5 µg/µl, or in a range of about 0.1 to about 2 µg/µl, e.g. 1 µg/µl. In a second step b) of the very preferred alternative, the protein solution is then preferably mixed with the substrate of the substrate binding protein (SBP), e.g. with coumermycin (Sigma Aldrich, St. Louis, Mo., cat. no. C9270, 50 mg/ml in DMSO), if GyrB is used as a substrate binding protein in the multifunctional fusion protein, preferably at a molar ratio of SBB:substrate of about 2:1. After incubation, preferably in a temperature range of about 15° C. to about 40° C., e.g. at RT or at 37° C., preferably for about 1 h, a PEG polymer as defined herein may be added in third step c) of the very preferred alternative. The multifunctional fusion protein as defined herein, containing the substrate binding protein (SBP) and the reactive (thioether-forming or further functionalizations for linker) moieties of the PEG polymer are preferably in a molar ratio of about 1:1. Hydrogel formation is then preferably achieved by incubation of the mixture obtained according to step c), preferably in a temperature range of about 15° C. to about 40° C., e.g. at RT (room temperature) or at 37° C., preferably for about 5 to 15 h, e.g. 10 h, preferably in a humidified atmosphere.

Alternatively, the inventive stimulus-responsive dissolvable PEG-hydrogel, may also be prepared by alternating the steps as identified above, e.g. by a) providing at least one multifunctional fusion protein as defined herein and a PEG-polymer as defined herein, wherein the at least one multifunctional fusion protein as defined herein is preferably (covalently) bound to the PEG-polymer as defined herein;

b) mixing the at least one multifunctional fusion protein as defined herein and the PEG-polymer obtained according to step a) with a substrate for the substrate binding protein (SBP) as defined herein, and thereby preferably forming the PEG hydrogel.

The conditions of reaction are likewise preferably as described above for steps a), b) and c). The at least one multifunctional fusion protein as defined herein and a PEG-polymer as defined herein are furthermore preferably covalently attached to each other as defined herein using molar ratios and reaction conditions as defined before for the first method, step c).

According to a further alternative, the inventive stimulus-responsive dissolvable PEG-hydrogel may also be prepared by alternating the steps as identified above, e.g.

a) providing at least one multifunctional fusion protein as defined herein and a PEG-polymer as defined herein, wherein a substrate for the substrate binding protein (SBP) as defined herein has been bound to the PEG-polymer;

b) mixing the at least one multifunctional fusion protein as defined herein and a PEG-polymer obtained according to step a) with a substrate for the substrate binding protein (SBP) as defined herein and thereby preferably forming the PEG hydrogel.

The conditions of reaction are likewise preferably as described above for steps a), b) and c).

The inventive stimulus-responsive dissolvable PEG-hydrogel, preferably as defined above and preferably as prepared above according to the inventive method, may be further modified by incorporating further components, selected from e.g. cells, proteins, polypeptides, antibiotics, antibodies, antimicrobial polymers, and non-steroidal clinically permitted antiphlogistics, such as derivates of (i) acetylsalicylacid, (ii) arylpropionacid, (iii) arylacticacid, (iv) indolaceticacid, (v) anthranilacid, and Oxicams, as well as selective COX-2-inhibitors.

Proteins, which may be incorporated into the inventive stimulus-responsive dissolvable PEG-hydrogel may be selected, without being limited thereto, e.g. from growth factors. In this context, without being limited thereto, growth factors may be selected from e.g. adrenomedullin (AM), autocrine motility factor, bone morphogenetic proteins (BMPs), epidermal growth factor (EGF), erythropoietin (EPO), fibroblast growth factors (FGFs), e.g. FGF-7, granulocyte-colony stimulating factor (G-CSF), granulocyte-macrophage colony stimulating factor (GM-CSF), growth differentiation factor-9 (GDF9), hepatocyte growth factor (HGF), hepatoma derived growth factor (HDGF), heparin binding growth factor (HBGF), insulin-like growth factor (IGF), migration-stimulating factor, myostatin (GDF-8), nerve growth factor (NGF) and other neutrophins, platelet-derived growth factor (PDGF), thrombopoietin (TPO), thrombospondin (TPS), transforming growth factor alpha(TGF-α), transforming growth factor beta (TGF-β), vascular endothelial growth factor (VEGF), placental growth factor (PlGF), [(Foetal Bovine Somatotrophin)] (FBS), IL-1-Cofactor for IL-3 and IL-6 (activates T cells), IL-2-T-cell growth factor (stimulates IL-1 synthesis, activates B-cells and NK cells), IL-3 (stimulates production of all non-lymphoid cells), IL-4 (growth factor for activated B cells, resting T cells and mast cells), IL-5 (induces differentiation of activated B cells and eosinophils), IL-6 (stimulates Ig synthesis, Growth factor for plasma cells), IL-7 (growth factor for pre-B cells), Tumor necrosis factor (TNF-a), angiostatin (inhibits neovascularization), etc. A particularly preferred growth factor is e.g. FFG-7, more preferably as defined according to SEQ ID NO: 50 (see also FIG. 9, aa 1 to 106). Even more preferred, a protein as defined above, which may be incorporated into the inventive stimulus-responsive dissolvable PEG-hydrogel, is selected from a fusion protein comprising a growth factor as defined above, optionally a linker as defined above, preferably an $F_c$-domain as defined herein, and optionally a tag for purification as defined above. Most preferably, such a fusion protein is selected from a sequence according to SEQ ID NO: 52 (herein termed FGF-7-Fc-His) or an amino acid sequence showing at least 50, 60, 70, or 80%, preferably at least 90%, more preferably at least 95%, and even more preferably at least 97.5% identity to the sequence according to SEQ ID NO: 52 (see also FIG. 9). Alternatively, such a fusion protein is encoded by a nucleic acid sequence according to SEQ ID NO: 51 or a nucleic acid sequence showing at least 50, 60, 70, or 80%, preferably at least 90%, more preferably at least 95%, and even more preferably at least 97.5% identity to the sequence according to SEQ ID NO: 51 (see also FIG. 9).

Proteins as defined above, which may be incorporated into the inventive stimulus-responsive dissolvable PEG-hydrogel may be bound to the PEG-hydrogel e.g. via the ZZ-domain of the incorporated inventive multifunctional fusion protein as defined above. For this purpose, the proteins to be incorporated are typically fused to a binding partner of the ZZ-domain, e.g. an $F_c$-domain, e.g. according to SEQ ID NO: 53 or an amino acid sequence showing at least 50, 60, 70, or 80%, preferably at least 90%, more preferably at least 95%, and even more preferably at least 97.5% identity to the sequence according to SEQ ID NO: 53 (see also FIG. 9, aa 123 to 354).

The proteins to be incorporated into the inventive stimulus-responsive dissolvable PEG-hydrogel may additionally be fused to a specific protease recognition sequence, which is preferably located between the protein as defined above and the binding partner of the ZZ-domain, as defined above. This approach allows for incorporation of the proteins into the inventive stimulus-responsive dissolvable PEG-hydrogel, and specific release of specific proteins, e.g. a specific growth factor, from the inventive hydrogel upon a specific trigger. Such a trigger may be a protease, having as a specific protease recognition sequence an amino acid sequence used to link the protein as defined above and the binding partner of the ZZ-domain, as defined above. Such protease recognition sequences might be either specific for endogenously produced proteases like matrix metalloproteases (MMPs as, for example, described in Ehrbar et al. (2007) Biomaterials 28, 3856-3866) or to proteases that might be added externally either together from the hydrogel administration or at another point of time. Accordingly, proteases as used in this aspect may include such endogenously produced proteases or matrix metalloproteases, or preferably proteases selected from, for example, factor Xa, caspases or the tobacco etch virus (TEV) protease.

Likewise, proteins in the inventive context to be incorporated into the inventive stimulus-responsive dissolvable PEG-hydrogel may be proteases as mentioned above.

The proteins may be incorporated into the inventive stimulus-responsive dissolvable PEG-hydrogel prior or parallel to forming the inventive hydrogel or by incubating the proteins with the (readily formed) PEG-hydrogel as defined herein. Incubation may occur preferably in a temperature range of about 15° C. to about 40° C., e.g. at RT or at 37° C. Incubation may furthermore occur preferably at a protein end concentration in a range of about 60 to about 140 ng/μl, in a range of about 70 to about 130 ng/μl, in a range of about 80 to about 120 ng/μl, or in a range of about 90 to about 110 ng/μl, e.g. about 100 ng/μl.

Cells, which may be used to be incorporated into the inventive stimulus-responsive dissolvable PEG-hydrogel may be selected, without being limited thereto, e.g. from stem cells, such as human stem cells, adult stem cells, embryonic stem cells, engineered or non-engineered stem cells, primary or immortalized (cell-lines) stem cells, preferably mesenchymal stem cells, osteoblasts, cementoblasts, fibroblast cells of all connective tissues, e.g. gingival and/or skin and corneal fibroblasts, either alone or together with periodontal ligament fibroblasts, keratinozytes, e.g. gingival keratinozytes and keratinocytes from the oral cavity and upper aerodigestive tract, as well as from the skin and the ocular surface, cells of the central nervous system, neuronal cells, endothelial cells of vascular and corneal tissue, pericytes, myocytes, adipocytes, astrocytes, melanocytes etc. Cells as defined above are preferably autologous cells, i.e. cells derived from the patient to be treated.

Advantageously, the inventive stimulus-responsive dissolvable PEG-hydrogel may be dissolved/degraded upon a specific stimulus. Such a specific stimulus may be e.g. the addition of a specific substrate or an antagonist of a substrate binding protein (SBP) as defined above. As an example, if GyrB is contained in the multifunctional fusion protein used to cross-link the PEG-hydrogel, the PEG-hydrogel may be degraded upon addition of the specific antibiotic novobiocin. Dissolvation/degradation may occur, if envisaged, also in a time staggered manner, e.g. via slow administration of a substrate or an antagonist of a substrate binding protein (SBP) as defined above to the inventive stimulus-responsive dissolvable PEG-hydrogel. Dissolvation/degradation is usually carried out at the application site of the inventive stimulus-responsive dissolvable PEG-hydrogel.

According to a further specific embodiment, the object underlying the present invention is furthermore solved by the use of the inventive stimulus-responsive dissolvable PEG-hydrogel as a medicament, medical device or medical product. Especially their chemical composition, their possibility to adjust their bioactive and biomimetic parameters with integrin recognition sequences as well as the incorporation of target specific growth factors render the inventive stimulus-responsive dissolvable PEG-hydrogels to an important and valuable tool in multiple clinical applications. Advantageously, the inventive stimulus-responsive dissolvable PEG-hydrogels may be used in multiple clinical applications.

Without being limited thereto, such clinical applications of the inventive stimulus-responsive dissolvable PEG-hydrogel, preferably in form of a medicament, medical device or medical product, include e.g. treatments in the field of implantology, dermatology and of carcinomas in the upper aerodigestive tract (e.g. during otorhinolaryngology or ear nose throat medicine) as well as wounds of the oral cavity (e.g. during oral and maxillofacial surgery).) and alveolar bone augmentation treatments. More precisely, such clinical applications of the inventive stimulus-responsive dissolvable PEG-hydrogel include e.g. wound dressings, tissue-supporting or tissue regenerating applications in the field of regenerative medicine, dental medicine and dentistry.

Among such applications, for example chronically ulcerating wounds may be treated within the field of dermatology as well as wounds in the field of regenerative medicine, in particular wounds, which may occur during surgical excision of carcinomas of the upper aerodigestive tract (e.g. during otorhinolaryngology or ear nose throat medicine) as well as wounds of the oral cavity (e.g. during oral and maxillofacial surgery) and alveolar bone augmentation as barrier function. In case of ulcerating wounds, which arise frequently in the lower part of the leg extremities with diabetes patients, autologous keratinozytes may be cultivated in vitro on the inventive stimulus-responsive dissolvable PEG-hydrogels in the presence of irradiated cell division inactivated dermal fibroblasts, until a preformed epithelium is obtained. Such autologous keratinozytes typically originate for example from the external hair root sheath, and are thus readily available. Subsequently, the inventive stimulus-responsive dissolvable PEG-hydrogels, which have been cultivated accordingly with such autologous cells, are preferably administered onto a preferably pretreated wound of the same patient the cells were derived from. Administration of the inventive stimulus-responsive dissolvable PEG-hydrogels onto the preferably pretreated wound of the patient typically occurs in a density and size, which preferably initiates healing of the wound and preferably allows support of the cells with nutrients from the surrounding tissue and fluids. Administration of the inventive stimulus-responsive dissolvable PEG-hydrogels also support occlusion of the wound due to a directed and systematic degradation of the PEG-hydrogel and the resulting release of specific proteins, such as keratinocyte promoting growth factors, such as EGF or FGF-7 (KGF). With respect to carcinomas of the upper aerodigestive tract (e.g. during otorhinolaryngology or ear nose throat medicine) as mentioned above, the keratinozytes applied with the inventive stimulus-responsive dissolvable PEG-hydrogels are typically derived from a so-called "forearm flap". In this case a piece of the entire skin of a part of the inner side of the forearm is removed and the fibroblasts of the connective tissue and the epithelial keratinozytes are grown in vitro. Since patients with such tumors typically suffer from impaired wound healing and accordingly show a correspondingly problematic granulation tissue, treatment of such patients and surgical dressing advantageously occurs under administration of "staggered" inventive stimulus-responsive dissolvable PEG-hydrogels containing epithelial cells and fibroblasts.

Such "staggered" inventive stimulus-responsive dissolvable PEG-hydrogels may contain epithelial cells and fibroblast either in one or in two different stimulus-responsive dissolvable PEG-hydrogels as defined herein as a "sandwich". Such a "sandwich" may be prepared e.g. by pre-culturing cells as defined herein, e.g. fibroblasts, initially on the surface, which may then be termed "undersurface", while further cells, e.g. keratinocytes, seeded with a time delay of one day, grow on the "upper surface" of the hydrogel. Interactions of both cell types via diffusible growth factors yields stratified epithelial formation or tissue formation in general over time, while both cell types lack direct cell-to-cell contacts. Advantageously, such "staggered" inventive stimulus-responsive dissolvable PEG-hydrogels, also termed "sandwich" stimulus-responsive dissolvable PEG-hydrogels, preferably provide for nutrition of the preformed (epithelial) tissue, in case of epithelial tissue particularly due to interaction with the fibroblasts via diffusible growth factors. Utilizing this approach, wound healing under occlusion of the epithelium shows a better outcome with respect to the pure preformed epithelium. In this case angiogenic growth factors such as VEGF may be incorporated into the inventive stimulus-responsive dissolvable PEG-hydrogel, which positively influence neovascularization of the wound tissue or the granulation tissue upon degradation of the gel.

Further advantageous clinical applications of the inventive stimulus-responsive dissolvable PEG-hydrogels, preferably in form of a medicament, medical device or medical product, include alveolar crest prevention after tooth extraction in a patient to be treated. Such applications may decisively contribute to the aesthetically and functionally successful application of dental implants in the dental medicine and dentistry. In Germany over 14 million teeth are extracted each year. Subsequent to dental extraction or dental loss the supporting bone of the lost tooth more or less collapses to some extent (atrophy). Accordingly, different degrees of bone loss or atrophy can be observed in this context. With an atrophy of the alveolar bone the aesthetic appearance may be impaired. Even worse, the prerequisites for implantology and further prosthetic rehabilitation are impaired. Augmentative measures to improve the function and the aesthetic appearance are therefore usually necessary and thus usually increase financial expenses and the surgical workload with respect to invasive operation procedures. Accordingly, the specific application of the inventive stimulus-responsive dissolvable PEG-hydrogels directly subsequent to tooth extraction or loss represents an adequate and cost efficient tool to avoid such expenses and subsequent treatments.

Additional advantageous of clinical applications of the inventive stimulus-responsive dissolvable PEG-hydrogels, preferably in form of a medicament, medical device or medical product, include the treatment of diseases of the human cornea in a patient to be treated. Such applications may be carried out in the treatment of diseases of the cornea, i.e. epithelium, connective tissue/fibroblasts, and endothelium. In diseases of the limbus ("limbus stem cell insufficiency") the vessel carrying cloudy epithelium of the connective tissue (conjunctiva) grows into the clear cornea typically resulting in blindness of the affected patient. Conventional treatment of such diseases typically requires a replacement of the limbus stem cells, which represent precursor cells of the clear cornea epithelium. In cases of one-sided diseases of the limbus the treatment may be carried out by transferring vital limbus tissue from the unaffected eye to the affected eye. In cases of an ambilateral such a treatment is not possible and much more problematic. In these cases, provided there is a remaining limbal function at least in one eye, a confluent cell layer may be grown on a suitable carrier matrix such as the inventive stimulus-responsive dissolvable PEG-hydrogels based on a small cell sample. The confluent cell layer may then be transferred to the affected eye. Until today a human amnion membrane or a fibrin gel was used as a carrier matrix, wherein the number of proliferating cells (stem cells) grown from the extracted cell sample represented the most critical aspect of such an ex vivo culture. Unfortunately, long term observations revealed poor number of stem cells on both of the carrier matrices presently used, i.e. the human amnion membrane or the fibrin gel. The reason for this failure is most likely the fact that none of these carrier matrices provide the optimal extracellular environment for such stem cells. Accordingly, these stem cells can not form a niche required for an optimal cell growth. In this context, the inventive stimulus-responsive dissolvable PEG-hydrogels provide an optimal environment due to their individually adaptable properties, which can be designed with respect to the requirement of these stem cells.

Further clinical applications of the inventive stimulus-responsive dissolvable PEG-hydrogels, preferably in form of a medical device, include the treatment of diseases of the endothelium of the cornea. A specific application in this context is e.g. treatment of Fuchs' endothelial dystrophy of the cornea. In this disease but also in the context of other diseases, a drastic reduction of the cells of the corneal endothelium occurs due to apoptosis leading to a cloudy cornea. The present therapy includes transplantation of the cornea including transplantation or replacement of all layers of the cornea. An alternative treatment includes replacement of diseased cells by a specific transplantation of the endothelial layer from a donor. Since the transplantation material is no HLA identical material the tissue graft may be rejected resulting in a significant damage of the endothelial layer. In this context, the inventive stimulus-responsive dissolvable PEG-hydrogels provide the possibility to extract endothelial cells from the patient to be treated and to enrich these endothelial cells similar to the above by growing a confluent cell layer on a suitable carrier matrix such as the inventive stimulus-responsive dissolvable PEG-hydrogels based on a small cell sample. Again, the inventive stimulus-responsive dissolvable PEG-hydrogels provide an optimal environment for these cells due to their individually adaptable properties, which can be designed with respect to the requirement of these stem cells. The cells may then be transferred together with the inventive stimulus-responsive dissolvable PEG-hydrogel as a carrier to the backside of the cornea and thus to avoid rejection of the graft.

The inventive stimulus-responsive dissolvable PEG-hydrogel, preferably in form of a medicament, medical device or medical product, may furthermore be used, e.g. in burn dressings, hemostatic patches, in the treatment of lesions, in the surgical dressing, for wound treating, for soft and hard tissue regeneration, e.g. in the field of implantology, for the treatment of wounds in the oral cavity, e.g. due to tumor diseases, in the field of ophthalmology, in the field of periodontal defects, including periodontal ligament etc., for preparing a cell implant for, integrally or partially, regenerating or reconstructing damaged or ill or removed tissues, in particular muscle, myocardium, connective, bone, tendon or ligamentous, hepatic, renal, corneal, dermis or epidermis, articular cartilagenous tissue, for preparing an implant of central nervous system cells as neuronal cells for, integrally or partially, regenerating or reconstructing neuronal tissue, in particular central nervous system tissue, nervous tissue, such as neuronal tissue, damaged as a result of Parkinson's disease or spinal marrow damages or oncologic pathologies or Alzheimer's disease, nervous tissue, such as neuronal tissue, removed or ablated, following an surgical operation. The inventive stimulus-responsive dissolvable PEG-hydrogels may furthermore be used as drug delivery devices, cell matrices for in vitro, in vivo and/or ex vivo applications, for preparation of tissue models and as cell transplantation matrices.

According to another specific embodiment, the object underlying the present invention is furthermore solved by the use of the inventive stimulus-responsive dissolvable PEG-hydrogel in the treatment of diseases, disease states or treatments in general as defined herein. More preferably, the inventive stimulus-responsive dissolvable PEG-hydrogel as defined herein may be used in the preparation of a medicament, a medical device or a medical product for the treatment of diseases as defined above.

According to final specific embodiment, the object underlying the present invention is furthermore solved by kits, preferably kits of parts, comprising the inventive stimulus-responsive dissolvable PEG-hydrogel, optionally further components for incorporation into the PEG-hydrogel as defined above, and optionally instructions for use. Such kits may be used in the treatment of diseases, disease states or treatments in general as defined herein and as mentioned above. The kit preferably comprises the different components in different parts of the kit, e.g. one part comprising the inventive stimulus-responsive dissolvable PEG-hydrogel, and at least one or more parts comprising one or more of the further components.

In the present invention, if not otherwise indicated, different features of alternatives and embodiments may be combined with each other. Furthermore, the term "comprising" shall not be construed as meaning "consisting of", if not specifically mentioned. However, in the context of the present invention, term "comprising" may be substituted with the term "consisting of", where applicable.

FIGURES

The following Figures shall illustrate the afore described invention in further detail and are not intended to limit the scope of the claims thereto.

FIG. 1: shows the inventive stimulus-responsive dissolvable PEG-hydrogel with RGD sequences and the spreading of human gingival fibroblasts on the hydrogel subsequent to phase contrast microscopy and the specific morphology of the seeded cells. As can be seen, the gingival fibroblasts continuously spread over the inventive stimulus-responsive dissolvable PEG-hydrogel with RGD sequences, leading to a continuously grown cell lawn within an incubation time of 24 hours. In particular, a significant increase of cell growth can be observed for gingival fibroblasts, which maintain their natural spindle-shaped morphology. In contrast, cells seeded on stimulus-responsive dissolvable PEG-hydrogel without RGD sequences show no continuous growth of cells within the incubation time of 24 hours. These cells are repelled from the gel and subsequently undergo apoptosis.

Figure 2:
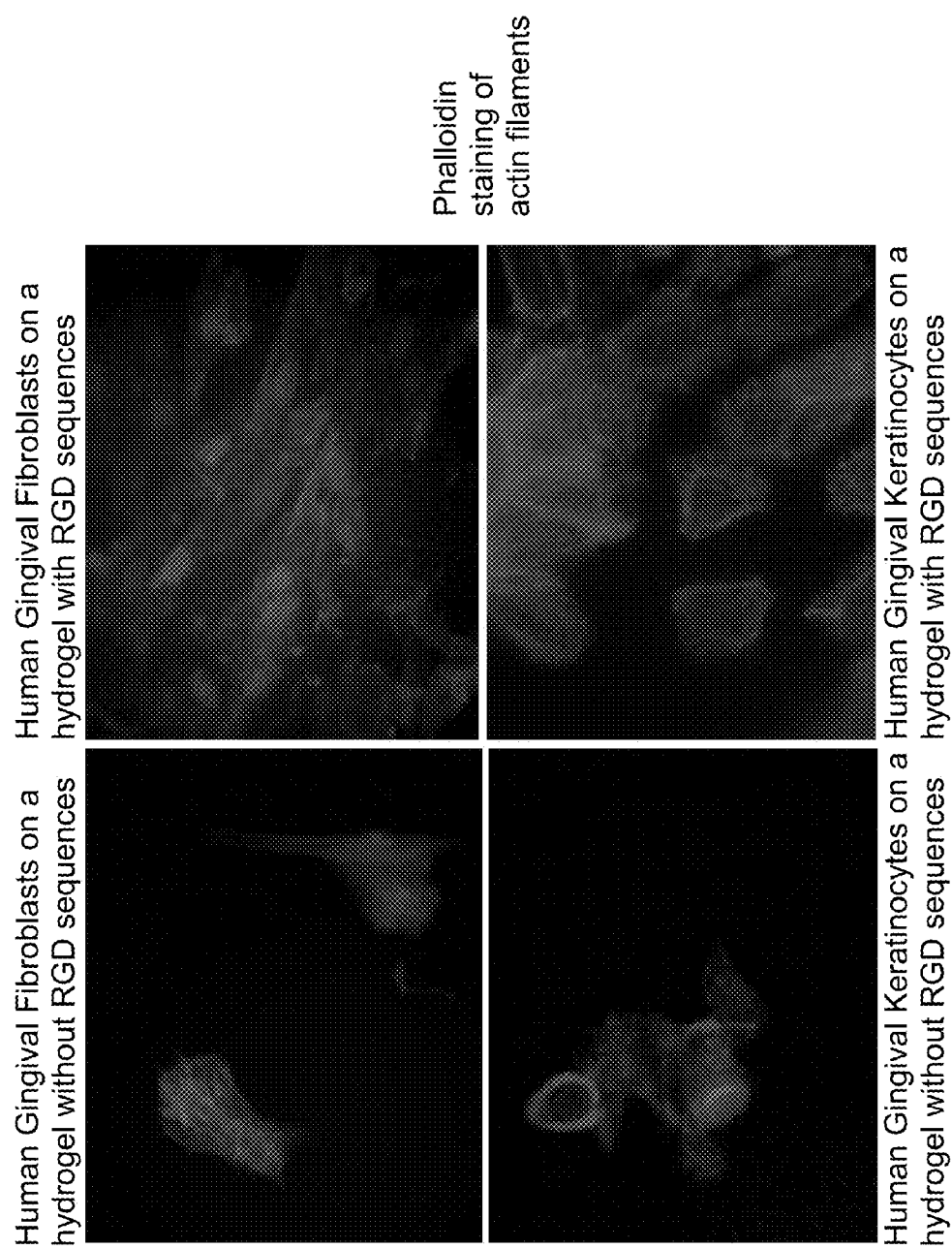

FIG. 2: shows the inventive stimulus-responsive dissolvable PEG-hydrogel with RGD sequences and the of human gingival fibroblasts and keratinocytes on the hydrogel subsequent to phalloidin staining and the actin filaments formed thereby. As can be seen, the gingival fibroblasts and keratinocytes continuously spread over the inventive stimulus-responsive dissolvable PEG-hydrogel with RGD sequences, leading to a continuously grown cell lawn within an incubation time of 24 hours. In particular, a significant increase of cell growth can be observed for gingival fibroblasts, which maintain their natural spindle-shaped morphology. In contrast, gingival cells seeded on stimulus-responsive dissolvable PEG-hydrogel without RGD sequences show no continuous growth and proper formation of actin filaments of cells within the incubation time of 24 hours. These cells are repelled from the gel and subsequently undergo apoptosis.

Figure 3:
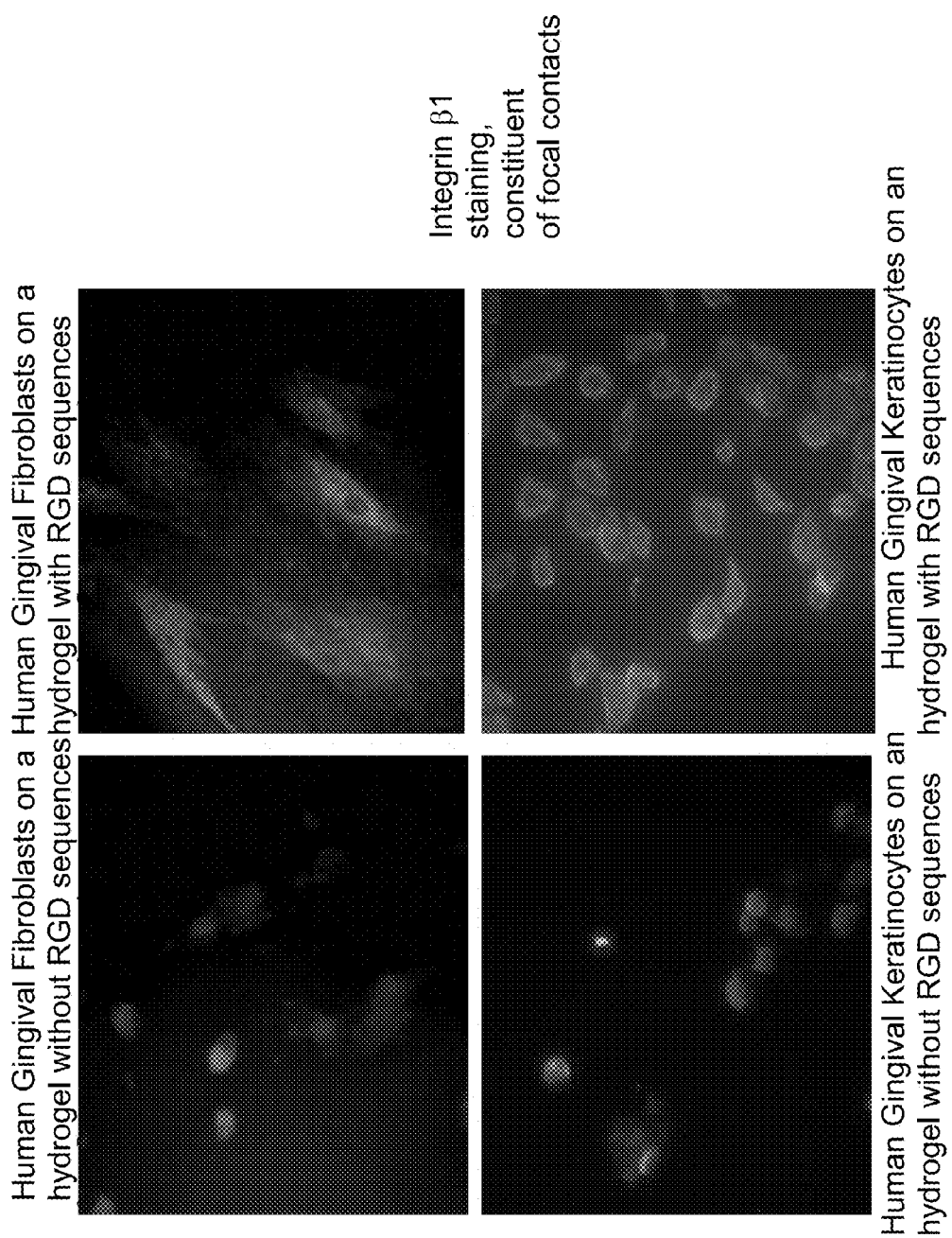
Figure 4:
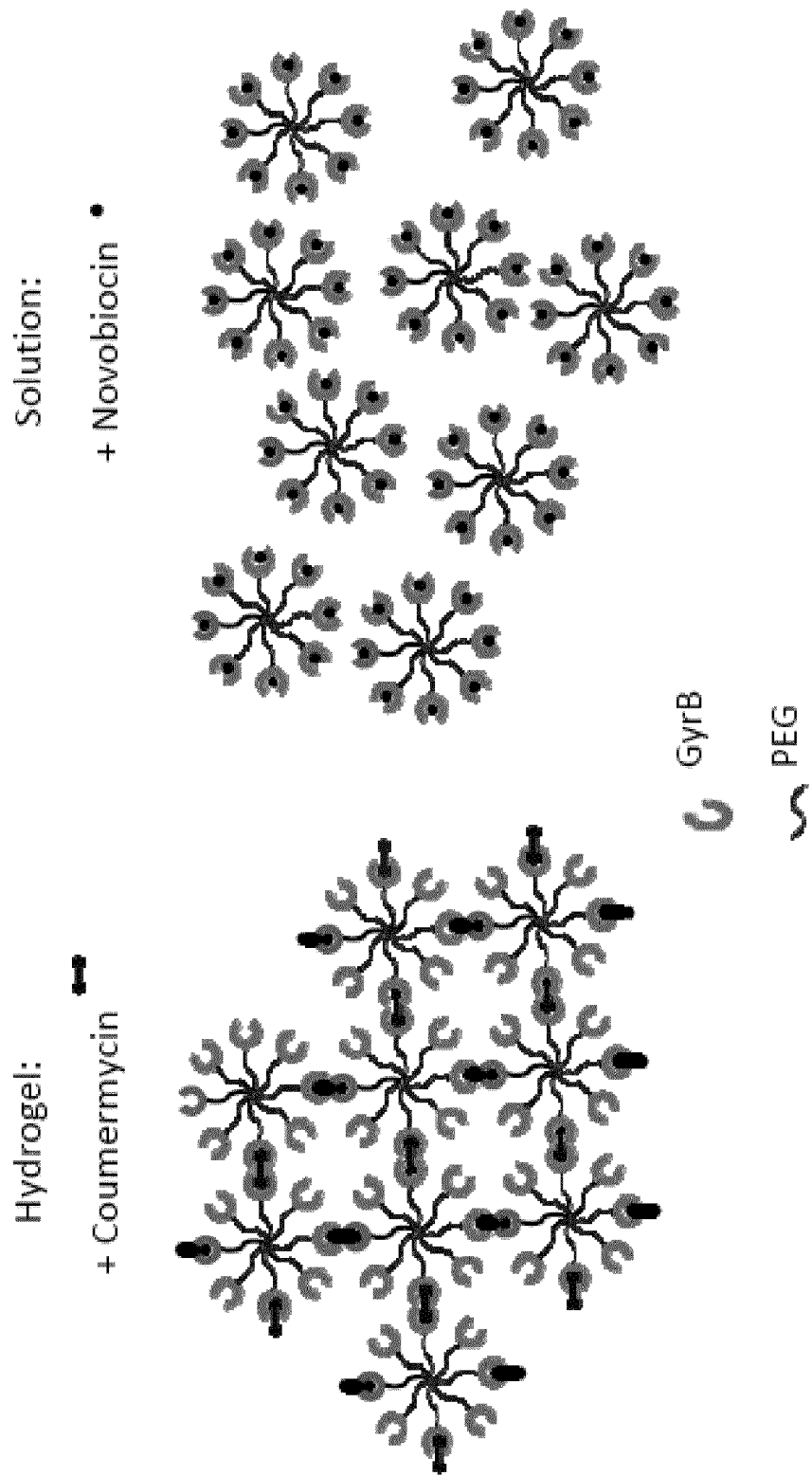

FIG. 3: shows the inventive stimulus-responsive dissolvable PEG-hydrogel with RGD sequences and the adhesion of human gingival fibroblasts and keratinocytes on the hydrogel subsequent to integrin-βb1-staining and the binding of the cells to the RGD-sequences (formation of focal contacts). As can be seen, the gingival fibroblasts continuously spread over the inventive stimulus-responsive dissolvable PEG-hydrogel with RGD sequences, leading to a continuously grown cell lawn mainly caused by proper cell adhesion via the integrin receptor subunit β1 to the incorporated RGD sequences in the hydrogel within an incubation time of 24 hours. In particular, a significant increase of cell growth can be observed for gingival fibroblasts, which maintain their natural spindle-shaped morphology. In contrast, cells seeded on stimulus-responsive dissolvable PEG-hydrogel without RGD sequences show no continuous cell growth of cells and were devoid of focal contacts within the incubation time of 24 hours. These cells are repelled from the gel and subsequently undergo apoptosis FIG. 4: shows an exemplary formation of the inventive stimulus-responsive dissolvable PEG-hydrogel, when using GyrB in the inventive multifunctional fusion protein to modify the underlying PEG-gel. Formation of the PEG-hydrogel is induced by adding the substrate coumermycin, whereas the PEG-hydrogel can be degraded again in a controlled manner using the antibiotic compound novobiocin.

FIG. 5: shows nucleic acid sequence (SEQ ID NO: 1)and the corresponding amino Acid sequence (SEQ ID NO: 2) of GyrB (aa 1-220).

FIG. 6: shows the nucleic acid sequence (SEQ ID NO: 44)and the corresponding amino acid sequence (SEQ ID NO: 45)of the inventive multimeric fusion protein pRG107. The subunits are as indicated in the following:
AA1: Methionine start
AA2: cysteine 1 for coupling to the PEG-VS
AA3-221: GyrB(1-220)
AA222-233: double-GRGDSP-motif
AA234-239: hexahistidine tag
AA240: cysteine 2 for coupling to PEG-VS FIG. 7: shows the nucleic acid sequence (SEQ ID NO: 46)and the corresponding amino acid sequence (SEQ ID NO: 47) of the inventive multimeric fusion protein pRG111. The subunits are as indicated in the following:
AA1-129: ZZ-binding domain, derived from pEZZ-18 (commercial vector, GE healthcare)
AA130-349: GyrB(1-220)
AA350-355: hexahistidine tag
AA356: cysteine for coupling to PEG-VS FIG. 8: shows the nucleic acid sequence (SEQ ID NO: 48) and the corresponding amino acid sequence (SEQ ID NO: 49) of the inventive multimeric fusion protein pRG116. The subunits are as indicated in the following:
Subunits:
AA1-220: GyrB(1-220)
AA221-232: double-GRGDSP-motif
AA233-238: hexahistidine tag
AA239: cysteine 2 for coupling to PEG-VS FIG. 9: shows the nucleic acid sequence (SEQ ID NO: 51) and the corresponding amino acid sequence (SEQ ID NO: 52) of fusion protein FGF-7-Fc-His. The subunits are as indicated in the following:
Subunits:
AA1-106: FGF-7 (=KGF)
AA107-122: serine-glycine linker
AA123-354: Fc domain
AA355-360: hexahistidine tag FIG. 10: depicts in a diagram the well configuration of experimental settings, the diagram showing the positioning of hydrogels with and without RGD and cell type seeded out.

Figure 11:
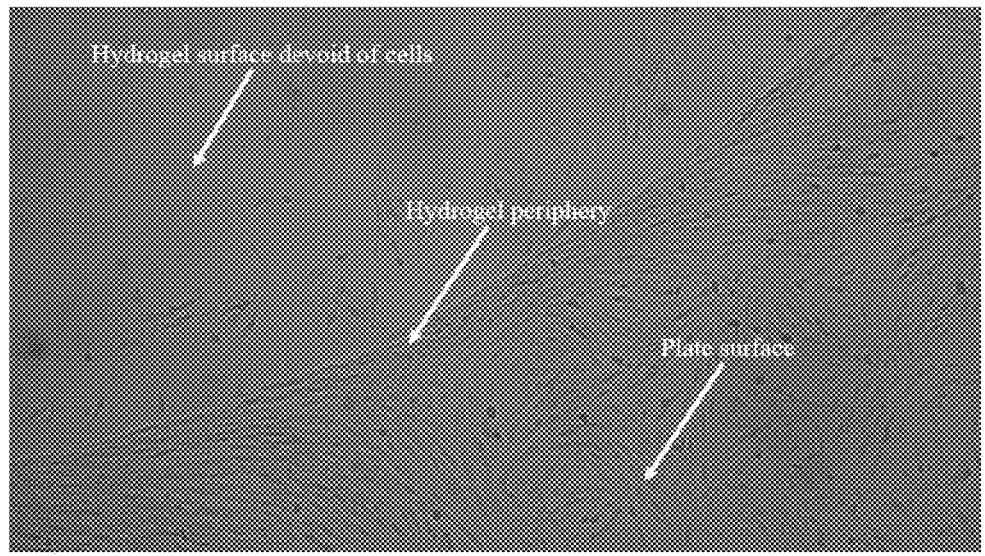

FIG. 11: shows an inverted microscope phase contrast image of gingival fibroblasts cultivated on a (without)–RGD hydrogel after 48 hours. The cell growth borderline results through the much more favorable plastic surface of the hydrogel surrounding cell culture substrate. On the –RGD hydrogel surface is almost no cell growth possible.

Figure 12:

FIG. 12: depicts in an inverted microscope phase contrast image of gingival fibroblasts cultivated on a +RGD hydrogel after 48 hours, the edge of the hydrogel was not discernable. The favorable +RGD hydrogel surface mediates a complete cell coverage after 48 hours cultivation time.

Figure 13:
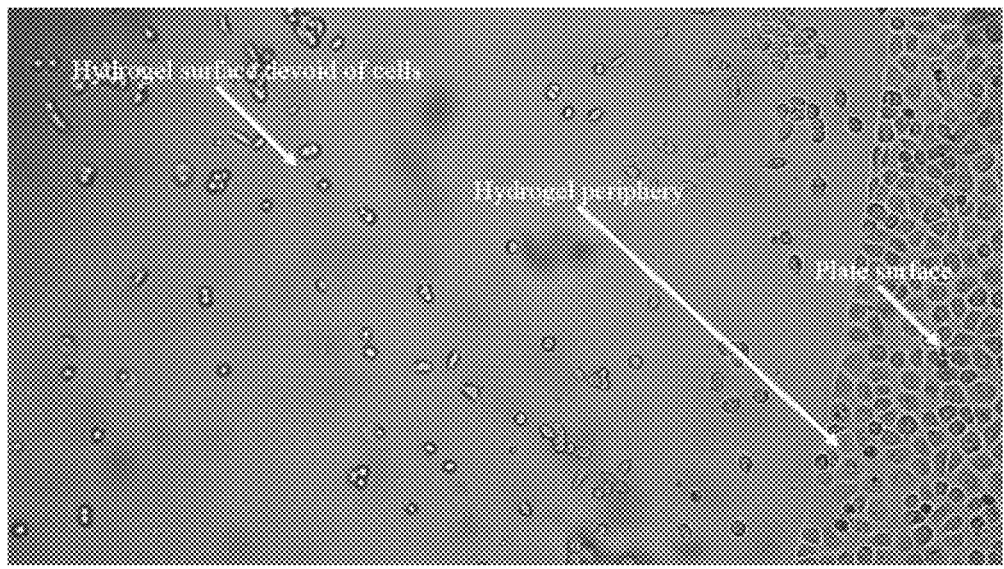

FIG. 13: provides an inverted microscope phase contrasts image of gingival keratinocytes on a (without)–RGD hydrogel after 48 hours. The cell growth borderline illustrates clearly that even the cell culture plastic substrate is the better growth surface for gingival keratinocytes than the –RGD hydrogel surface. Only single cells are able to adhere to the cell repellent surface.

Figure 14:
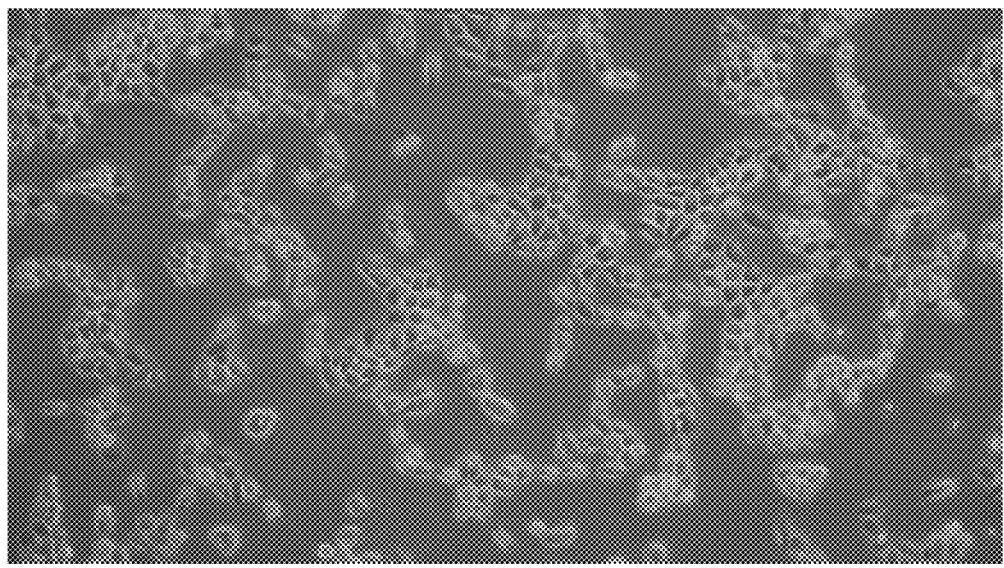

FIG. 14: shows an inverted microscope phase contrast image of gingival keratinocytes on a +RGD hydrogel after 48 hours. The cell growth and proliferation proceeds in islands and native cell morphology depicts the favorable environment (+RGD hydrogel) for gingival keratinocytes.

Figure 15:
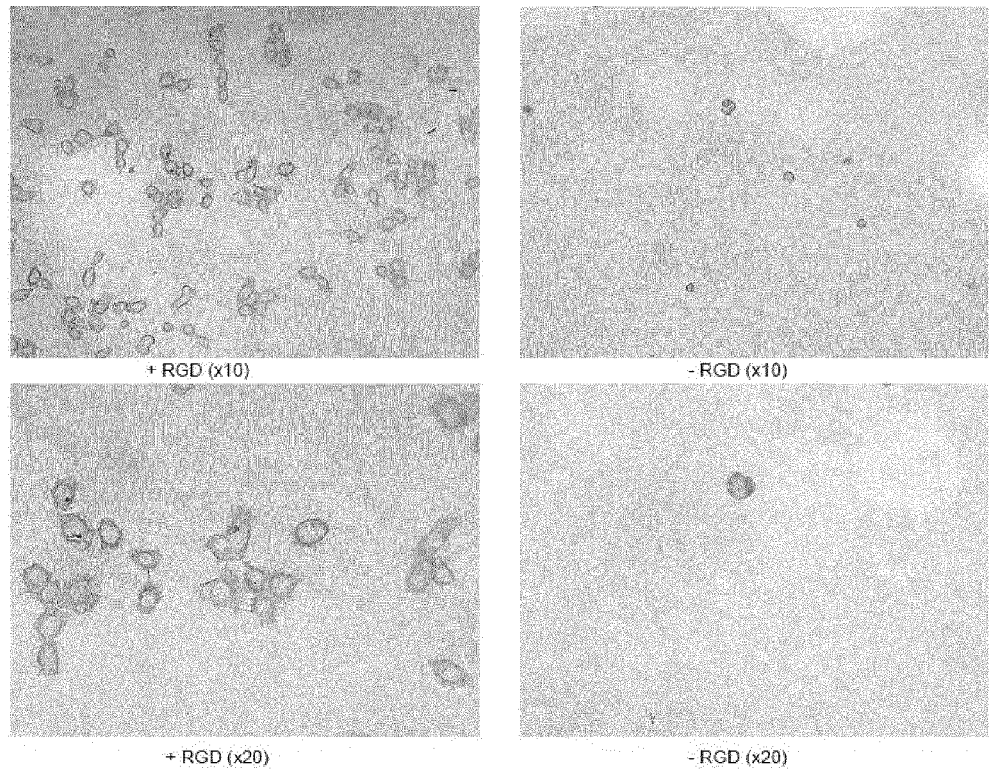

FIG. 15: shows gingival keratinocytes immunohistochemically stained for cytokeratin 19 with the DAB horse radish peroxidase precipitation method. The staining pattern of the cells illustrates on the +RGD hydrogel surface complete cell spreading and therefore proper cell adhesion to the hydrogel surface. In contrast, sparsely distributed cells cultivated on the –RGD hydrogel surface showed almost no cell spreading and depict unnatural spherical cell morphology.

Figure 16:
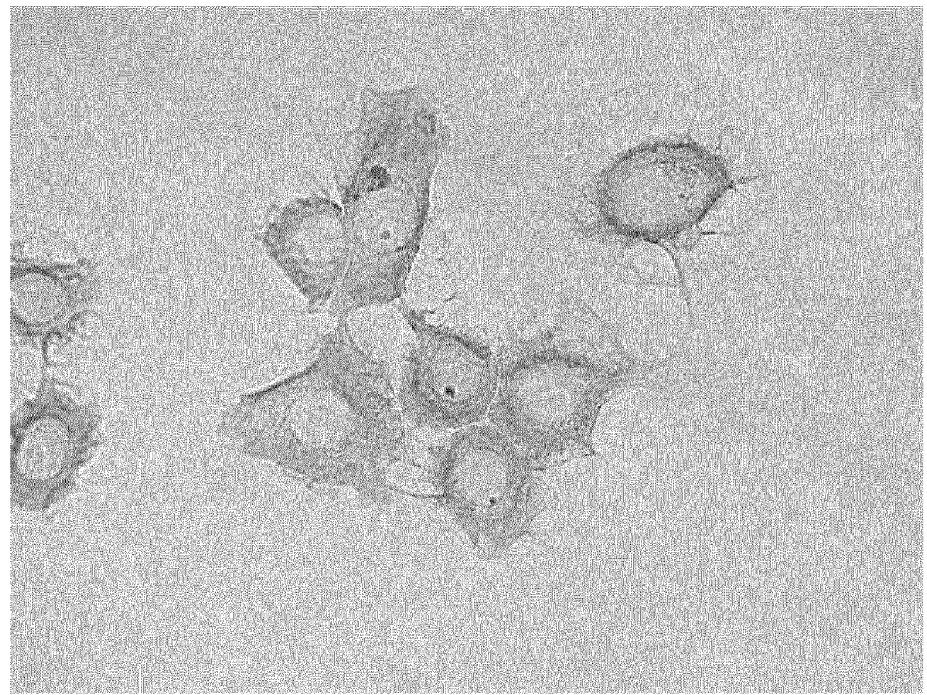

FIG. 16: exemplifies a higher magnification image the results with gingival keratinocytes seeded on a hydrogel containing the RGD sequence immunohistochemically stained for cytokeratin 19 with the DAB horse radish peroxidase precipitation method. The higher magnification image emphasizes the complete cell spreading and the cell specific keratin 19 distribution in the cell's cytoplasm.

Figure 17:
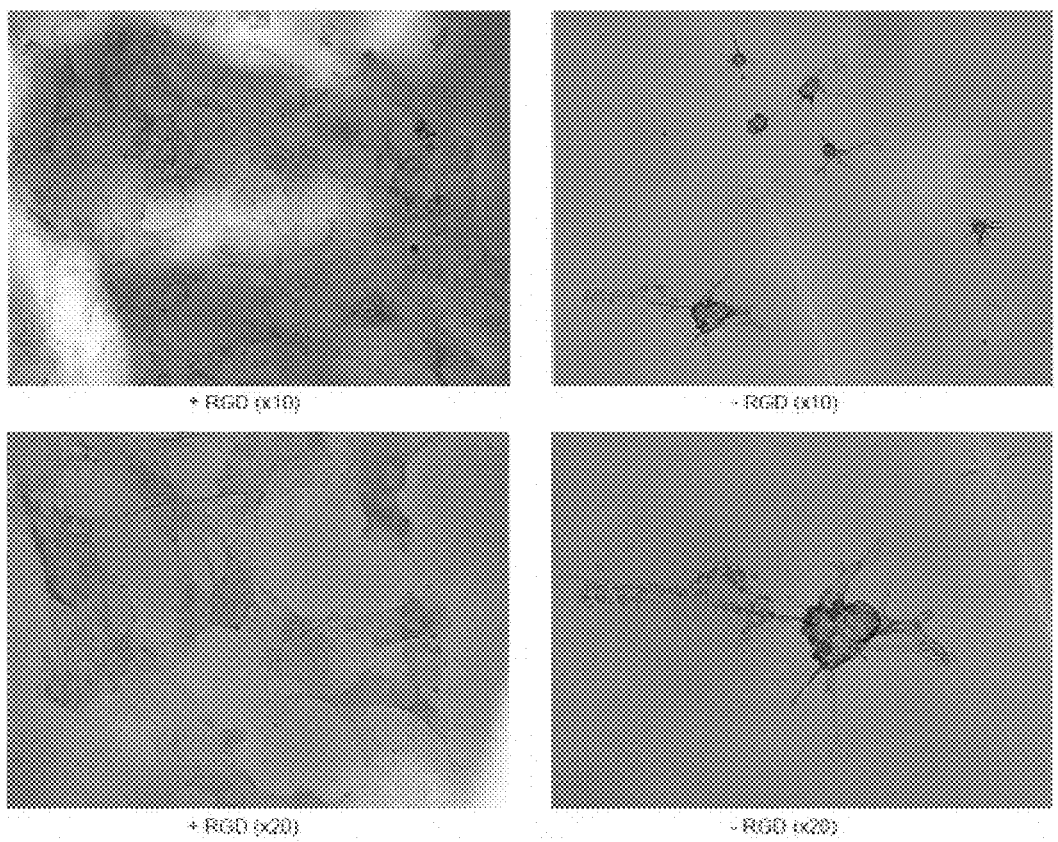

FIG. 17: shows gingival fibroblasts immunohistochemically stained for integrin 133 with the DAB horse radish peroxidase precipitation method (brightly lit areas were due to lighting effects caused by the overlying translucent hydrogel). Cells cultivated on +RGD hydrogel surfaces show complete cell spreading and proper cell adhesion to the gel surface. In contrast, cells seeded on –RGD hydrogel surfaces are sparsely distributed, showed unnatural morphology and the cell branches illustrates nicely that no cell adhesion points are available.

FIG. 18: depicts the nucleic acid sequence (upper sequence) (SEQ ID NO: 54) and the amino acid sequence (lower sequence) (SEQ ID NO: 55) of FluA-flourescein (FluA_A45I_R95K_S114R).

FIG. 19: depicts the nucleic acid sequence (upper sequence) (SEQ ID NO: 56) and the amino acid sequence (lower sequence) (SEQ ID NO: 57) of DigA (DigA__16).

FIG. 20: depicts the nucleic acid sequence (upper sequence) (SEQ ID NO: 58) and the amino acid sequence (lower sequence) (SEQ ID NO: 59) of Salicyclic Acid Binding Protein 2 (SABP2).

FIG. 21: depicts the nucleic acid sequence (upper sequence) (SEQ ID NO: 60) and the amino acid sequence (lower sequence) (SEQ ID NO: 61) of Salicyclic Acid Binding Protein 2 (SABP2 S81A).

FIG. 22: depicts the nucleic acid sequence (upper sequence) (SEQ ID NO: 62) of *Arabidopsis* FK506 binding protein (FKBP42), the nucleic acid sequence (middle sequence) (SEQ ID NO: 63) of *Arabidopsis* FK506 binding protein (FKBP42 (aa 1-163)) and the amino acid sequence (lower sequence) (SEQ ID NO: 64) of *Arabidopsis* FK506 binding protein (FKBP42 (aa 1-163)).

FIG. 23: depicts the nucleic acid sequence (upper sequence) (SEQ ID NO: 65) and the amino acid sequence (lower sequence) (SEQ ID NO: 66) of *Arabidopsis* multiresistance-like ABC transporter AtPGP1.

FIG. 24: depicts the nucleic acid sequence (upper sequence) (SEQ ID NO: 67) and the amino acid sequence (lower sequence) (SEQ ID NO: 68) of *Arabidopsis* multiresistance-like ABC transporter AtPGP1 (aa 980-1286).

Figure 25:
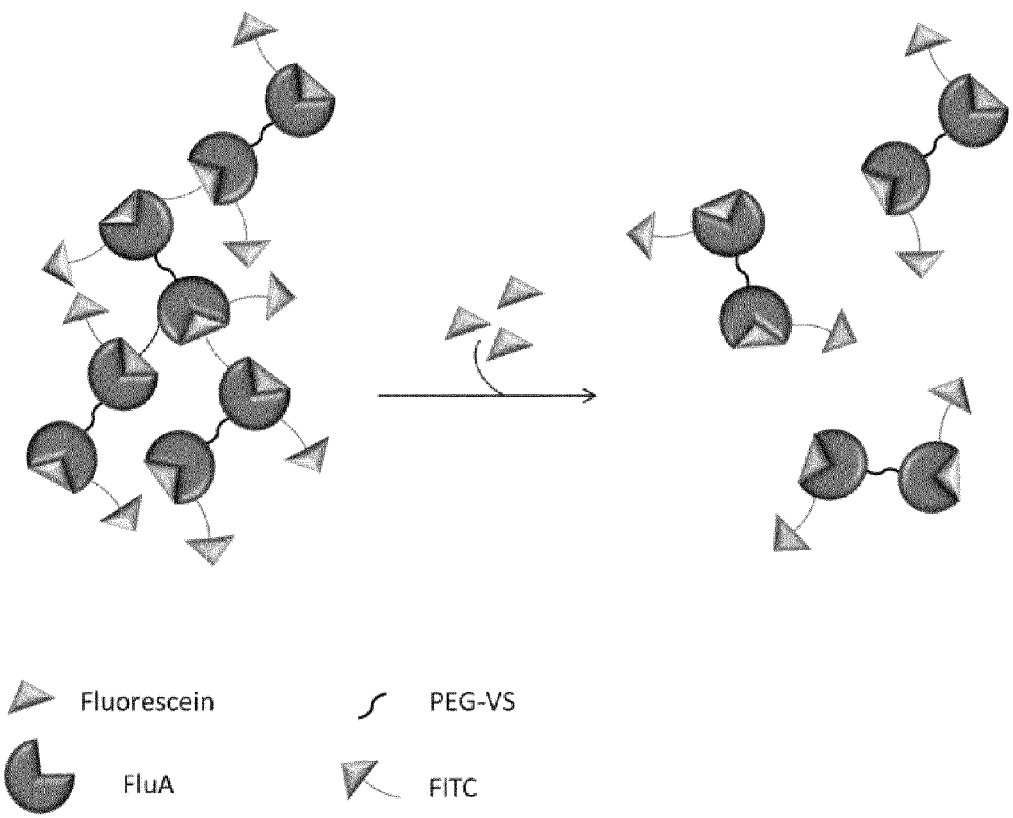

FIG. 25: shows stimulus-sensing hydrogel based on the affinity of FluA towards fluorescein.

FIG. 26: shows stimulus-sensing hydrogel based on the affinity of DigA towards digoxin.

FIG. 27: shows stimulus-sensing hydrogel based on the affinity of SABP2 towards salicylic acid.

Figure 28:
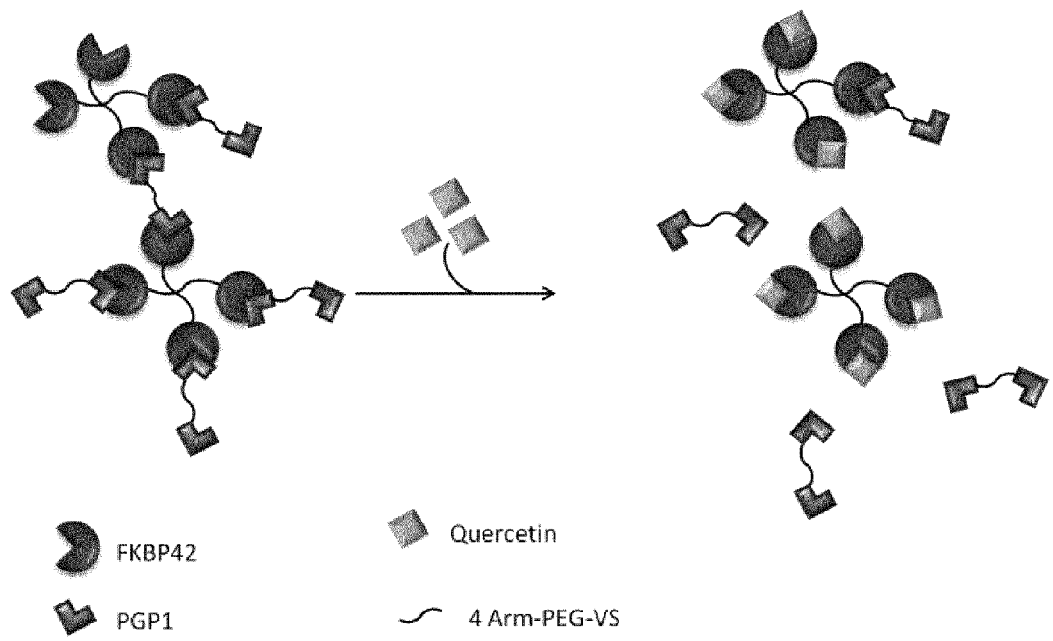

FIG. 28: shows stimulus-sensing hydrogel based disruption of the protein-protein interaction of FKBP42 and AtPGP1 by quercetin.

FIG. 29: shows the results of Example 7 of the test of frequency dependent viscoelastic properties of hydrogels with RGD sequence (upper graph) and hydrogels without RGD (lower graph), wherein the results have been depicted in Hertz (Hz).

FIG. 30: shows the results of the test of Example 7 of frequency dependent viscoelastic properties of hydrogels with RGD sequence (upper graph) and hydrogels without RGD (lower graph), wherein the results have been depicted in angular frequency w (rad/sec).

Figure 31:
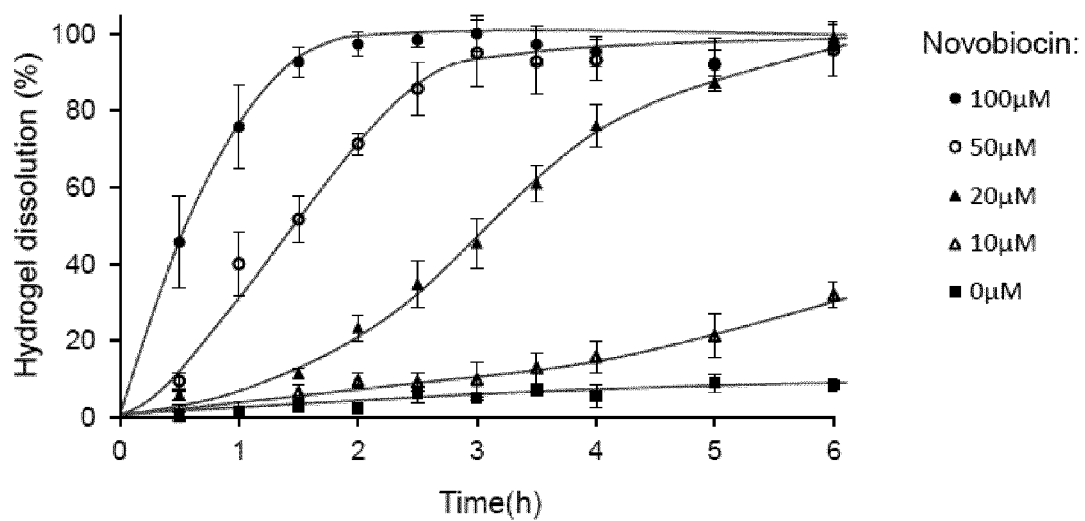

FIG. 31: shows the results from the dissolution kinetics of GyrB-PEG hydrogels in synthetic body fluid.

Figure 32:
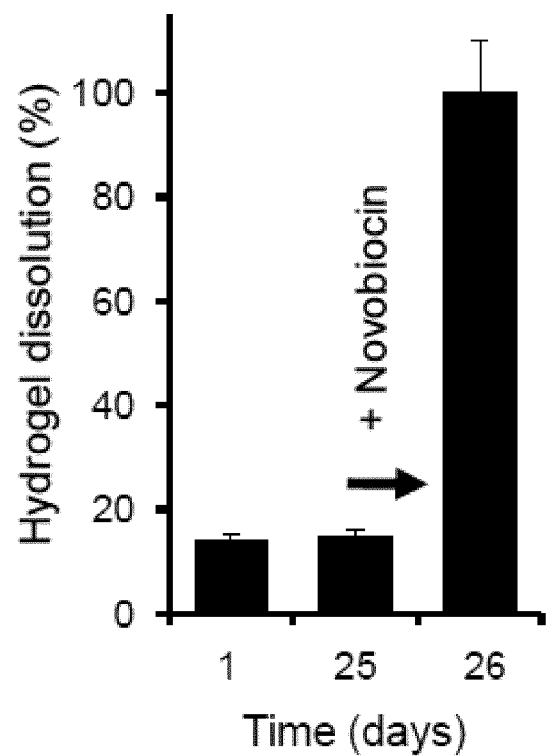

FIG. 32: shows the results from long term stability tests (storage at 4° C.) of inventive hydrogels as described in Example 1 with GyrB and multiarm-PEG.

FIG. 33: depicts the amino acid sequence of the scFv exemplarily used in the experimental section (SEQ ID NO: 69). This scFv fragment is directed against fluorescein and derivatives of it (see Vaughan et al., (1996), *Nat. Biotechnol* 14 (3), S. 309-314). The scFv was recombinantly produced as a C-terminal hexahistidine tagged version in established expression systems as described for example by (see Pedrazzi et al., (1997), *FEBS Lett* 415 (3), S. 289-293), expression in the periplasm of *E. coli* (see Rippmann et al., (1998), *Appl. Environ. Microbiol.* 64 (12), S. 4862-4869), expression in L-form cells of *Proteus mirabilis*. The amino acid sequence of the produced scFv is the depicted after removal of the periplasmic signal sequence.

Figure 34:
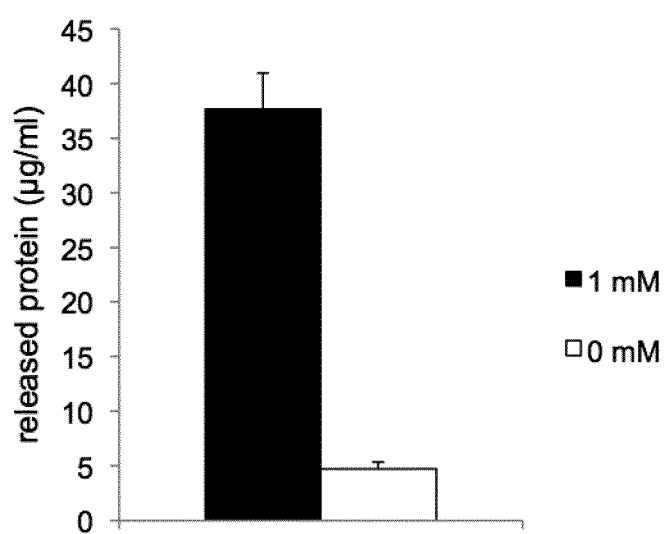

FIG. 34: shows the validation of the scFv hydrogels according to Example 10. As a result, it could be seen that the incubation of the hydrogels with 1 mM fluorescein led to dissolution of the hydrogel and release of the incorporated proteins into the supernatant (quantified after 1 day using the Bradford method) whereas the incubation without fluorescein (0 mM) led to no significant hydrogel dissolution and protein release (quantified after 1 day using the Bradford method).

EXAMPLES

The following Examples shall illustrate the afore described invention in further detail and are not intended to limit the scope of the claims thereto.

Example 1

Polymer Synthesis and Modification 8-arm-Polyethylene-glycol-vinylsulfone (PEG-VS, molecular weight 37.5 kDa) was synthesized according to Lutolf M P, Hubbell J A. 2003. Synthesis and physicochemical characterization of end-linked poly(ethylene glycol)-co-peptide hydrogels formed by Michael-type addition. Biomacromolecules 4(3):713-22) starting from 8-arm PEG-OH (Shearwater polymers, Huntsville, Ala.):

Multiarm PEG-VSs were synthesized by coupling PEG-OHs with an excess of divinyl sulfone (Aldrich, Buchs, Switzerland). PEG-OH (ca. 5 g) was either used as received and dissolved directly in 300 mL of dry dichloromethane (previously dried over molecular sieves) or, in some cases, PEG was dried by azeotropic distillation in toluene using a Dean Stark trap before starting the reaction. To the PEG dissolved in dichloromethane, NaH was added under argon, at 5-fold molar excess over OH groups. After hydrogen evolution, divinyl sulfone was added very quickly at 50- to 100-fold molar excess over OH groups. The reaction was carried out at room temperature for 3 days under argon atmosphere with constant stirring. Afterward the reaction solution was neutralized with concentrated acetic acid, filtered through paper until clear, and reduced to a small volume (ca. 10 mL) by rotary evaporation. PEG was precipitated by adding the remaining solution dropwise into ice-cold diethyl ether. The polymer was recovered by filtration, washed with diethyl ether, and dried under vacuum. The dry polymer was then dissolved in 200 mL of deionized water containing ca. 5 g of sodium chloride and extracted three times with 200 mL of dichloromethane. This solution was dried with sodium carbonate, and the volume was again reduced by rotary evaporation. Finally, the product was reprecipitated and thoroughly washed with diethyl ether to remove all remaining divinyl sulfone. The final product was dried under vacuum and stored under argon at −20° C. Derivatization was confirmed with NMR (CDCl$_3$): 3.6 ppm (PEG backbone), 6.1 ppm (d, 1H, =CH$_2$), 6.4 ppm (d, 1H, =CH$_2$), and 6.8 ppm (dd, 1H, —SO$_2$CH=). The degree of end group conversion, as shown by NMR, was found to range from 95 to 98%. Gel permeation chromatography was used to confirm that the starting material (PEG-OH) and the end-functionalized PEG-VS have identical molecular weight distributions.

Example 2

Production of Exemplary Inventive Multifunctional Fusion Proteins

The following exemplary multifunctional fusion proteins (herein also determined as GyrB variants) were cloned and expressed:

| | | | | | | |
|---|---|---|---|---|---|---|
| pRG116 N- | GyrB | RGD$_2$ | His$_6$ | Cys | -C | |
| pRG107 N- | Cys | GyrB | RGD$_2$ | His$_6$ | Cys | -C |
| pRG111 N- | ZZ | GyrB | His$_6$ | Cys | -C | |
| pRG116 N- | GyrB | RGD$_2$ | His$_6$ | Cys | -C | |
| pRG107 N- | Cys | GyrB | RGD$_2$ | His$_6$ | Cys | -C |
| pRG111 N- | ZZ | GyrB | His$_6$ | Cys | -C | |

The plasmid pRG116 contains the N-terminal sequence of E. coli Gyrase B (aa 1-220) followed a double RGD-sequence (2×GRGDSP), a hexahistidine-tag for purification and a cysteine residue for coupling to the PEG-VS.

The plasmid pRG107 contains, additionally to pRG116, an N-terminal cysteine residue.

The plasmid pRG111 contains 2 synthetic Fc-binding Z-domains from protein A (ZZ, derived from vector pEZZ-18, GE healthcare) followed by the N-terminal sequence of E. coli Gyrase B (aa 1-220), a hexahistidine-tag for purification and a cysteine residue for coupling to the PEG-VS.

The corresponding GyrB expression plasmid (pRG107, pRG111, pRG116) was transformed into E. coli BL21 STAR™ (DE3) (Invitrogen, Carlsbad, Calif., cat. no. C601003) and protein production was induced at $OD_{600}=1$ with 1 mM IPTG for 3 h at 37° C. The cell pellet was resuspended in PBS (40 ml per 1000 ml initial culture volume, 50 mM $NaH_2PO_4$, 300 mM NaCl, 10 mM imidazole, pH 8.0), disrupted using a French press (Thermo Fisher Scientific, Waltham, Mass.) and cell debris was eliminated by centrifugation at 30,000×g for 30 min. The cleared cell lysate was loaded onto an NTA-agarose Superflow column (Qiagen, Hilden, Germany, cat. no. 30210) which was subsequently washed with 10 column volumes PBS, 10 column volumes wash buffer (50 mM $NaH_2PO_4$, 300 mM NaCl, 20 mM imidazole, pH 8.0) and eluted with 2 column volumes elution buffer (50 mM $NaH_2PO_4$, 300 mM NaCl, 250 mM imidazole, pH 8.0). To the eluate, 500 mM EDTA pH8 was added to a final concentration of 10 mM.

Example 3

Hydrogel Assembly

Prior to coupling the inventive multifunctional fusion proteins to the PEG-VS polymer the inventive multifunctional fusion proteins were reduced using a reducing agent, preferably with TCEP. This step prevents the thiol moiety reacting to a disulfide bond and is necessary for coupling the inventive multifunctional fusion proteins to the PEG-VS. Subsequently to reacting the inventive multifunctional fusion proteins with the reducing agent, the inventive multifunctional fusion proteins are preferably purified to remove or at least substantially remove the reducing agent, to prevent interference of the reducing agent, e.g. TCEP, with the reduced multifunctional fusion proteins and/or the PEG-VS polymer during the coupling reaction.

In this context, a 20-fold molar excess of TCEP (Tris(2-carboxyethyl)phosphine hydrochloride, Sigma Aldrich, St. Louis, Mo., cat. no. C4706) was added to the corresponding protein eluate and incubated at room temperature for 1 h. Subsequently, the buffer of the reduced protein samples was exchanged to PBS, 2 mM EDTA pH 8 by 2× separation on a size-exclusion column (Thermo Fisher Scientific, Waltham, Mass., cat. No. 43233) and concentrated up to a concentration of 150 µg/µl by ultrafiltration (10 kDa MWCO, Sartorius, Gottingen, Germany, cat. no. VS0202) under continuous nitrogen atmosphere.

The hydrogels were prepared by mixing 5 molar amounts of reduced $GyrB_{116}$ with 1 molar amount of reduced $GyrB_{102}$ to a protein end concentration of 100 µg/µl. Reduced $GyrB_{111}$ was added to an end concentration of 1 µg/µl. The protein solution was then mixed with coumermycin (Sigma Aldrich, St. Louis, Mo., cat. no. C9270, 50 mg/ml in DMSO) at a molar ratio of GyrB:coumermycin=2:1. After incubation at RT for 1 h, PEG-VS was added at a molar ratio of GyrB:VS groups=1:1. Hydrogel formation was achieved by incubation at 37° C. in a humidified atmosphere for 10 h.

Example 4

Growth Factor Incorporation

The growth factors are produced in mammalian cells (HEK293-T) with a C-terminal hexahistidine and an Fc-tag. Via its Fc-subunit, the growth factor can be incorporated into the hydrogel by binding to the ZZ-domain of $GyrB_{111}$. Upon addition of novobiocin leading to hydrogel dissolution, the growth factor will also be released.

Example 5

Cell Adhesion Experiments

In order to evaluate the optimized cellular adhesion capacity of the developed RGD-functionalized hydrogel, two cell types of the oral cavity, human gingival fibroblasts (hGF) and immortalized human gingival keratinocytes (IHGK), were seeded at a cell density of $5 \times 10^4$ per hydrogel and cultivated for 24 h under standard cell culture conditions. Documentation of cellular growth behaviour and morphology was performed by phase contrast microscopy (PCM). The experimental setup includes comparison of the two different cell types cultivated on hydrogels with or without RGD-functionalization. PCM on hydrogels without RGD-sequences revealed an atypical morphology for hGF and IHGK. Both cell types appeared less attached to the hydrogel surface as indicated by their morphology and showed a very low proliferation rate which was corroborated by the formation of only small cell islands (FIG. 1, left column). In clear contrast, the cellular behaviour on hydrogels with RGD-sequences (RGD-functionalization) illustrated that this type of modification results in a comfortable environment for the cell types under study. In more detail, hGF and IHGK showed their natural cellular morphology and in contrast to the cells growing on hydrogels without RGD-sequences, they displayed a drastic increase in proliferation rate, which was evidence by a nearly complete cell carpet revealed by the PCM mode (FIG. 1, right column). To verify proper cell adhesion and regular cell morphology, hGF and IHGK cultivated on both hydrogel configurations (+/−RGD) were fixed with paraformaldehyde and subjected to immunostaining protocols. To illustrate cell morphology, cells were treated with the staining dye (phalloidin) which specifically intercalates into the actin filaments of the cytoskeleton. Comparison of the red fluorescent staining pattern of hGF and IHGK on the hydrogel configurations (+/−RGD) confirmed the observation from the phase contrast microscopy and revealed the irregular rotund shaped cell morphology on the hydrogels without RGD-sequences (FIG. 2, left column). In contrast, hGF and IHGK cultivated on hydrogels +RGD-sequences displayed again their regular cell morphology, which was highlighted by the observation of the actin filament orientation at the cell's periphery (FIG. 2, right column).

RGD-sequences are cellular adhesion points in the extracellular matrix and are constituents of the matrix molecules collagen type I and fibronectin. Cells can adhere to these RGD-sequences via certain integrin subunits including the integrin subunit β1. Therefore, the integrin subunit PI distribution in hGF and IHGK seeded on the two hydrogel configurations (+/−RGD) was analyzed. The comparison of the integrin β1-specific green fluorescent signal distribution revealed again the accumulation at the cell periphery on the +RGD hydrogel configuration which points to proper cell adhesion, the formation of focal contacts and the development of a regular cell morphology (FIG. 3, right column). In contrast, the integrin β1 distribution in cells cultivated on the −RGD hyrogel configuration suggest that the cells cannot find proper adhesion points at the surface and therefore remained as an irregular rotund shaped morphology (FIG. 3, left column). Moreover, the integrin β1-specific green fluorescent signal remained very weak which points to a decreased integrin β1 expression due to the lack of adhesion sites (FIG. 3, left column). In summary, the RGD-sequence incorporation into the hydrogel represents an optimization of the invented medical device with respect to proliferation and adhesion of hGF and IHGK.

Example 6

Additional Cell Adhesion Experiments with Inventive Hydrogels

Aim

To observe morphological changes, proliferation and growth characteristics of gingival fibroblasts and gingival (or corneal) keratinocytes seeded out on inventive hydrogels with and without RGD (Arg-Gly-Asp) sequences as prepared according to Example 1.

Method

Hydrogels

The hydrogels used in this example were produced following the protocol outlined for Example 1 by functionalizing a "Star"-PEG (Polyethyleneglycol) molecule with the Gyrase-B protein as defined and prepared in previous examples shown above. GyrB is involved in the folding of DNA within bacteria and as such is targeted by the antibiotic novobiocin. Accordingly, a hydrogel is produced when the Gyrase-B functionalized Star-PEG molecule is mixed with coumermycin, a molecule which conceptually resembles a novobiocin dimer and serves to link proximal Gyrase-B proteins to form a 3D gel network. Upon the addition of novobiocin to the hydrogel, which is a molecule that possesses a competitive affinity for the Gyrase-B moiety, the hydrogel can be dissolved. RGD sequences were incorporated into the hydrogel in order to provide binding sites for cells to adhere to the hydrogel.

Field Phase Contrast Inverted Microscopy $1 \times 10^5$ ginginval fibroblast (GF) and gingival keratinocyte (GK) cells were seeded out in 2 ml media onto a 12 well plate, in which each well contain a hydrogel of 40 µL, half of which possessed RGD sequences (+RGD) and half of which did not (−RGD). Cells were incubated for 48 hours, after which an inverted microscope was used to examine confluence and morphology.

Immunohistochemical Staining

Horse Radish Peroxidase Precipitation

6x−RGD and 4x+RGD hydrogels (40 uL each) were prepared in 12 well plates. GF and GK cells were plated out onto the gels at $1 \times 10^5$ cells per well and incubated for 24 hours. Media was then aspirated and the gels washed twice with 2 mL PBS. Antibody solutions were prepared as shown below in Table 1 for staining.

TABLE 1

Primary antibodies used to stain cells on + and − RGD hydrogels

| Cell type | Antibody | Dilution (in PBS with 0.05% Tween) | Vol. (µL) |
|---|---|---|---|
| GK | K19 | 1:50 | 100 |
| GF | INTβ3 | 1:50 | 100 |

Cells were fixed with 4% formaldehyde (diluted in PBS) for 20 minutes in the 12 well plate. The gels were then washed 3 times with 2 mL PBS. Hydrogels were subsequently scraped from the bottom of the wells and inverted onto 50 µL of antibody solution placed on a ~2 cm square of parafilm. Hydrogels were left for 1 hour to soak in the 1° anti-solution, after which they were gently raised out of the solution by spatula and inverted onto another piece of parafilm. The hydrogels were subsequently washed three times with 50 µL PBS solution. Thereafter, 100 µL of the appropriate 2° antibody was (rabbit, goat) was pipetted onto the hydrogel and left for 40 minutes. Next the 2° antibody was aspirated and the hydrogel washed three times with 500 µL PBS. 100 µL pre-prepared DAB solution (20 µL DAB in 1 mL DAB diluent) was pipetted onto the hydrogel and left for 10 minutes. After removal of the DAB solution, the hydrogels were washed with water and mounted on a cover slip with glycerine.

Figure 10:
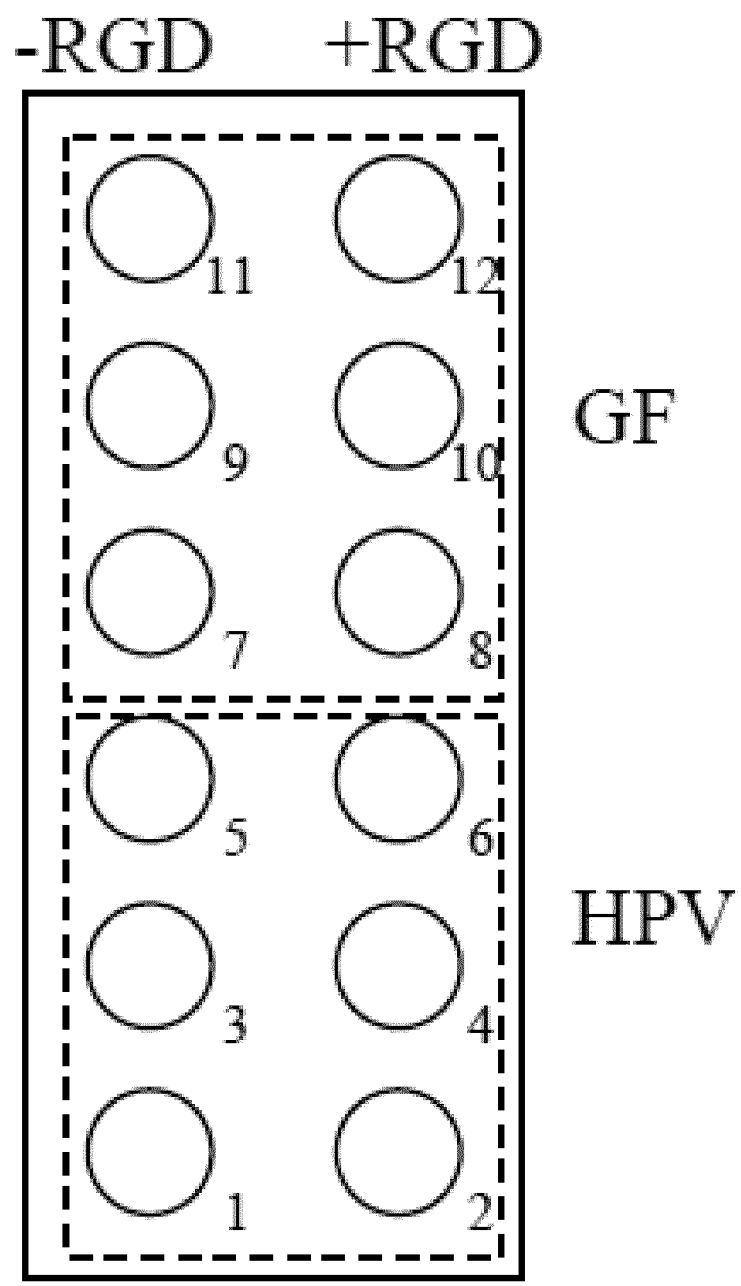

Phalloidin-Rhodamine Immunohistochemical Staining of Corneal Keratinocytes and Gingival Fibroblasts for F-Actin Hydrogels (40 µL) plated in a 12 well silicone plate as prepared according to Example 1 were arranged as shown in FIG. 10. Corneal keratinocytes (C-K) were employed in place of gingival keratinocytes. GF and C-K cells were plated out at $7 \times 10^3$ cells/well equating to $3.5 \times 10^4$ cells/well in 200 µL of media on top of the hydrogels. Cells were left to grow for 5 days, after which cells were examined and photographed with an inverted microscope before further treatment.

Medium was aspirated from above the wells containing hydrogels, the hydrogels were washed twice with 200 µL PBS after which the cells were fixed for half an hour with 200 µL 4% formaldehyde. After removal of the formaldehyde, the hydrogels were washed twice with 200 µL PBS and then treated for 3 hours with undiluted bovine serum albumin (BSA). Thereafter, BSA was aspirated and the hydrogels washed twice with 200 µL PBS. Cells on each hydrogel were then treated with 30 µL rhodamine-phalloidin diluted at 1:40 for 20 minutes. Subsequently, the rhodamine-phalloidin solution was aspirated and the hydrogels within the wells were washed 3 times with 200 µL PBS solution. Cells were then stained with 30 µL 300 nM DAPI for 10 minutes and subsequently washed 3 times with 200 µL PBS. The silicone well structure was then removed from the glass slide to which it was attached, the hydrogels were mounted in Vectorshield and a glass slide was placed on top of the hydrogel. Samples were observed and photographs taken using a fluorescence microscope with a 60× oil objective.

Integrin αV and Integrin β1 Immunohistochemical Staining of Gingival Keratinoctyes and Gingival Fibroblasts Hydrogels were placed in silicone wells as presented in FIG. 10. Cells were seeded out onto the hydrogels at $7 \times 10^3$ cells per well in 200 µL medium, gingival fibroblasts and gingival keratinocytes. Cells were incubated for 24 hours, examined under inverted microscope and photographs taken using the inverted microscope. Thereafter, cells were stained immunochemically with antibodies as outlined below in Table 2.

TABLE 2

| Cell type with primary antibody stained | |
|---|---|
| HPV-16 GK | GF |
| αV integrin | β1 integrin |

Staining protocol: Medium was removed and each well was washed twice with 200 μL PBS. Thereafter, cells were fixed with 4% paraformaldehyde (PF) for a half hour. PF was removed and the cells washed twice with PBS. Thereafter PBS was removed and 200 μL BSA was pipetted onto the cells and left for 1 hour. The BSA was removed and the gels washed with PBS. Primary antibodies were diluted 1:50 in PBT (PBS and Tween) and secondary antibodies were diluted at 1:300. 30 μL of each primary antibody were pipetted onto the gels and left overnight at 4° C. overnight.

Results

Field Phase Contrast Inverted Microscopy

Inverted microscopic images of the cells on the hydrogels showed superior proliferation and/or adhesion on the +RGD hydrogels, when compared to the −RGD hydrogels. This is shown in FIG. 11 where the −RGD hydrogel is visible in top left. Clearly visible is the lack of fibroblast cells growing on the hydrogel surface in comparison to the well surface at the periphery of the hydrogel. This is in stark contrast to the +RGD hydrogels where a continuous carpet of cells was observed and no hydrogel edge was discernable, shown in FIG. 12.

This pattern of growth and for adhesion was mirrored in the appearance of the gingival keratinocytes. The margin of the hydrogel was lined by a near confluent carpet of keratinocyte cells in a marked contrast to the sparse density of cells on the hydrogel surface. This is shown in FIG. 13, and contrasts to FIG. 14 where the cells growing on the hydrogel were not as dense as those growing on the plate surface, but markedly more than those cells on the −RGD hydrogel surface.

Immunohistochemical Precipitation Staining—Horse Radish Peroxidase

Cytokeratin 19 immunohistochemical staining revealed a strong contrast in the morphology of those gingival keratinocyte cells growing on +RGD hydrogels and −RGD hydrogels, as shown in FIG. 15 showing microscope pictures of +RGD and −RGD hydrogels left and right respectively.

A higher magnification photograph of K19 staining of gingival keratinocytes in FIG. 16 shows in greater detail the distribution of the keratin 19 protein.

Immunohistochemical staining of gingival fibroblasts for integrin β3 using the DAB kit horse radish peroxidase system illustrated profound differences in morphology between cells growing on +RGD hydrogels and −RGD hydrogels presented below in FIG. 17. The almost complete carpet of cells on the +RGD hydrogel contrasted to the appearance of only occasional cells on the −RGD hydrogel with atypical morphology.

Through phalloidin-rhodamine staining the F-actin filaments within the cell were revealed under fluorescence microscopy as shown in FIG. 2 for gingival fibroblasts and for corneal keratinocytes. For both cell types, cells grown on the +RGD hydrogels displayed a significantly more expansive morphology in comparison to those grown on the −RGD hydrogels.

Fluorescence microscopy was carried out under 20×/0.75 Plan Apo Objective. Quality image definition was difficult to achieve because of significant non specific background fluorescence. In spite of this, integrin β1 staining revealed an obvious difference in the morphology, proliferation and spreading of the cell cultivated on the +RGD hydrogels in comparison to the −RGD cells, which is shown in FIG. 3.

The integrin βV immunochemical staining on GK cells showed a similar disparity between cells cultivated on +RGD and −RGD hydrogels to those seen for integrin β1 for GF cells. This difference is clearly visible in FIG. 3.

Discussion

All forms of characterisation of the produced inventive PEG hydrogels revealed that both gingival fibroblasts and gingival keratinocytes (in one analysis—corneal keratinocytes) attached and proliferated on the +RGD hydrogel. In the case of gingival fibroblasts, the rate of proliferation appeared to be similar to that of the cells on the plate bottom as indicated by the absence of a line of demarcation between hydrogel and plate bottom shown in FIG. 12. This appeared not to be the case for gingival keratinocyte cells as shown in FIG. 13 and FIG. 14, where a denser carpet of cells was seen around the periphery of the −RGD hydrogel than those growing on the +RGD hydrogel. However, this phenomenon is also explained by considering the shape of the hydrogel, which was of a convex disk. Therefore, it is possible that upon settling, many cells rolled off the −RGD hydrogel, due to limited capability to adhere to the PEG material, leading to a cell concentrating effect on the plate surface at the hydrogel periphery. By contrast, adherence of cells to the +RGD hydrogel would have had an equalising effect on the density distribution of the cells overall. Cytokeratin 19 (K19) staining using the DAB horse radish peroxidase method was useful in contrasting the morphology between GK cultivated on +RGD and −RGD hydrogels. Here we see many cells on the +RGD hydrogels with normal morphologies compared to the sparsely populated −RGD hydrogel with balled cells. K19 is not normally expressed in keratinizing keratinocytes, but is seen in non-keratinizing epthilial basal cells (see Schön, M. and J. G. Rheinwald (1996), "A Limited Role for Retinoic Acid and Retinoic Acid Receptors RAR[agr] and RAR[beta] in Regulating Keratin 19 Expression and Keratinization in Oral and Epidermal Keratinocytes." 107(3): 428-438), as well as in both normal and benign hyperplastic non-keratinized basal mucosal cells (see Lindberg, K. and J. G. Rheinwald (1989), American Journal of Pathology 134(1): 89-98). There is some evidence of increased cytokeratin 19 expression in HPV-16 immortalised ectocervical and foreskin keratinocytes (see Sun, Q., K. Tsutumi, et al. (1993), International Journal of Cancer 54: 656-662), as well as embryonal keratin K19 in HPV-16 immortalised gingival keratinocytes (see Oda, D., L. Bigler, et al. (1996), Experimental Cell Research 10(1): 164-169). The expression of K19 seen in the currently presented results is consistent with the observations of these authors. Similarly, staining of the cell attachment protein integrin β3 for GF cells on +RGD hydrogels revealed a near complete coverage of the protein over the surface of the hydrogel indicating comprehensive cell attachment. The −RGD hydrogel however exhibited few cells with a highly atypical morphology. Rhodamine-phalloidin staining for F-actin on GF and corneal keratinocytes again highlighted the difference between cells on +RGD and −RGD hydrogels, with those on +RGD a displaying normal distribution of F-actin throughout the cell. Immunohistochemical staining of GK showed a significantly greater signal for adhesion protein αV from cells on the +RGD hydrogel than the −RGD. αVβ6 intergrin is expressed by keratinocytes in mucosal wound conditions and in vitro after sub-culturing (see Haapasalmi, K., K. Zhang, et al. (1996). "Keratinocytes in Human Wounds Express [agr]v[beta]6 Integrin." 106(1): 42-48). Although, a large amount of background fluorescence was observed, integrin β1 staining showed also considerably more of this adhesion protein on the +RGD hydrogels compared to the −RGD hydrogels. Integrin β1 has been shown to be expressed in gingival fibroblasts and is important for adhesion to enamel matrix proteins (see Van Der Pauw, M. T. M., V. Everts, et al. (2002), Journal of Periodontal Research 37(5): 317-323), while its metabolism and distribution has been shown to be affected by nicotine in cigarette smoke possibility leading to weaker periodontal attachment (see Snyder, H., G. Caughman, et al. (2002), Journal of Periodontology J Periodontol 73(5): 505-10)

Conclusion

Self-releasing PEG hydrogels formed with Gyrase-B and coumermycin with RGD sequences according to the present invention proved to be a vastly superior cell culturing substrate in comparison to hydrogels without RGD and comparable to cell culture plates.

Example 7

Test of Viscoelastic Properties of Hydrogels with RGD Sequence and Hydrogels without RGD In a further test the viscoelastic properties of inventive PEG-hydrogels with RGD sequence as prepared according to Example 1 and comparative hydrogels without PEG-RGD have been tested (see FIGS. 29 to 30). For mechanical hydrogel characterization, hydrogel disks (40 µl volume, 1 mm height) were prepared between two siliconized glass cover slips and swollen in synthetic body fluid for 1 h. The storage and loss moduli (G' and G") were obtained in small-strain oscillatory-shear experiments using a modular advanced rheometry system II (Thermo Scientific) at 20° C. with a 20 mm parallel steel plate and a gap size of 0.5 mm. Measurements were conducted in a constant strain (20%) mode as a function of frequency (from 0.1 to 10 Hz) to obtain the mechanical spectra. In this context FIG. 29 shows the results of the test of frequency dependent viscoelastic properties of the hydrogels with RGD sequence (upper graph) and comparative hydrogels without RGD (lower graph), wherein the results have been depicted in Hertz (Hz). FIG. 30 shows the results of the test of frequency dependent viscoelastic properties of hydrogels with RGD sequence (upper graph) and hydrogels without RGD (lower graph), wherein the results have been depicted in angular frequency ω (rad/sec). Both tests prove the gel-like properties of the inventive PEG-hydrogels with and without RGD sequence as prepared according to Example 1.

Example 8

Dissolution Kinetics of GyrB-PEG Hydrogels in Synthetic Body Fluid

In a further example the dissolution kinetics of inventive GyrB-PEG hydrogels in synthetic body fluid dependent on different concentrations of novobiocin have been investigated (see FIG. 31). To remove unbound components, the hydrogels were initially incubated in synthetic body fluid at 4° C. for 24 h. Afterwards, the hydrogels were transferred to synthetic body fluid containing corresponding concentrations of novobiocin and incubated at 4° C. Hydrogel dissolution was monitored by the quantification of released protein in the supernatant using the Bradford method. The results prove the dose-adjustable dissolution kinetics of the inventive GyrB-PEG hydrogels. The inventive GyrB-PEG hydrogels are inventive PEG-hydrogels with RGD sequence as prepared according to Example 1.

Example 9

Hydrogel Longterm Stability (Storage at 4° C.)

Additionally, hydrogel longterm stability (storage at 4° C.) of inventive PEG-hydrogels with RGD sequence as prepared according to Example 1 has been investigated. For this purpose, the gels have been incubated in synthetic body fluid at 4° C. for 24 h. Then, the hydrogels were transferred to synthetic body fluid and stored at 4° C. for 25 days. Addition of 1 mM novobiocin after 25 days led to complete dissolution of the hydrogels as monitored by the quantification of the released protein in the supernatant using the Bradford method. Incubation without novobiocin didn't lead to hydrogel dissolution. As a result the hydrogels as prepared according to Example 1 appear to be stable over a long term storage time and can then still be dissolved with novobiocin (see FIG. 32).

Example 10

Production of scFv Hydrogels

Intro

The hydrogel design of the present example is based on a branched polymer which is grafted with a single-chain variable fragment (scFv) which specifically binds to fluorescein (a common contrast agent in ophthalmology) and some of its derivatives such as fluoresceinisothiocyanate (FITC). Gel formation is achieved by the crosslinking of the scFv protein mediated by FITC-decorated bovine serum albumin (BSA). Addition of fluorescein allows for dose- and time-adjustable dissolution of the hydrogel.

Polymer Synthesis

As a polymer used in the context of the present Example poly(AAm-co-Ni$^{2+}$-NTA-AAm) was used as an estimate of the properties of a corresponding PEG polymer. The polymer was prepared initially. The synthesis of poly(AAm-co-Ni$^{2+}$-NTA-AAm) has been described in: (see Ehrbar et al., (2008), *Nat Mater* 7 (10), S. 800-804). A preparation of a corresponding inventive PEG polymer follows.

Protein Production

Furthermore, scFv fragments were produced. These scFv were directed against fluorescein and have been named FITC-E2 as published in Vaughan et al. 1996 (see Vaughan et al., (1996), *Nat. Biotechnol* 14 (3), S. 309-314). For production the scFv was recombinantly produced as a C-terminal hexahistidine tagged version in established expression systems as described for example by:

(Pedrazzi et al., (1997), *FEBS Lett* 415 (3), S. 289-293), expression in the periplasm of *E. coli*
(see Rippmann et al., (1998), *Appl. Environ. Microbiol.* 64 (12), S. 4862-4869), expression in L-form cells of *Proteus mirabilis*

The protein sequence of the produced scFv is shown in FIG. 33 (SEQ ID NO: 69) (after removal of the periplasmic signal sequence).

The cell pellet after expression was resuspended in PBS (40 ml per 1000 ml initial culture volume, 50 mM NaH$_2$PO$_4$, 300 mM NaCl, 10 mM imidazole, pH 8.0), disrupted using a French press (Thermo Fisher Scientific, Waltham, Mass.) and cell debris was eliminated by centrifugation at 30,000×g for 30 min. The cleared cell lysate was loaded onto an NTA-agarose Superflow column (Qiagen, Hilden, Germany, cat. no. 30210) which was subsequently washed with 10 column volumes PBS, 10 column volumes wash buffer (50 mM NaH$_2$PO$_4$, 300 mM NaCl, 20 mM imidazole, pH 8.0) and eluted with 2 column volumes elution buffer (50 mM NaH$_2$PO$_4$, 300 mM NaCl, 250 mM imidazole, pH 8.0). The buffer of the protein eluate was exchanged to 50 mM NaH$_2$PO$_4$, 300 mM NaCl, 10 mM imidazole, pH 8.0 by 2× separation on a size-exclusion column (Thermo Fisher Scientific, Waltham, Mass., cat. No. 43233) and concentrated to 40 mg/ml by ultrafiltration (10 kDa MWCO, Sartorius, Gottingen, Germany, cat. no. VS0202).

FITC-BSA Production

Bovine serum albumin (BSA, Sigma Aldrich, St. Louis, Mo., cat. no. 05479, 1 mg/ml in 100 mM sodium carbonate buffer pH 9) was mixed with a 10× molar excess of Fluoresceinisothiocyanate (FITC, Sigma Aldrich, St. Louis, Mo., cat. no. F3651, 1 mg/ml in anhydrous DMSO) and incubated for 12 h at 4° C. The reaction was stopped by the addition of NH$_4$Cl to an end concentration of 50 mM. Subsequently, the buffer was exchanged to 50 mM NaH$_2$PO$_4$, 300 mM NaCl, 10 mM imidazole, pH 8.0 by 2× separation on a size-exclusion column (Thermo Fisher Scientific, Waltham, Mass., cat. No. 43233) and upconcentrated to 100 mg/ml by ultrafiltration (10 kDa MWCO, Sartorius, Gottingen, Germany, cat. no. VS0202). The obtained molar ratio of coupled FITC to BSA was 2.9 to 1 as determined by measuring the absorbance at 495 nm and 280 nm respectively.

Hydrogel Assembly 5 volumes of purified scFv (40 mg/ml in 50 mM NaH$_2$PO$_4$, 300 mM NaCl, 10 mM imidazole, pH 8.0) were added to 1 volume of FITC-BSA (100 mg/ml in 50 mM NaH$_2$PO$_4$, 300 mM NaCl, 10 mM imidazole, pH 8.0) and 2 volumes of poly(AAm-co-Ni$^{2+}$-NTA-AAm) (as 0.6% w/v solution in 50 mM NaH$_2$PO$_4$, 300 mM NaCl, 10 mM imidazole, pH 8.0) and mixed by gently stirring. The hydrogel formed immediately and was further incubated in a humidified atmosphere for 12 h at RT.

Validation of the scFv Hydrogels

To remove unbound components, the hydrogels were initially incubated in 1 ml of 50 mM NaH$_2$PO$_4$, 300 mM NaCl, 10 mM imidazole, pH 8.0 at RT for 24 h. Afterwards, the hydrogels were transferred to 1 ml of 50 mM NaH$_2$PO$_4$, 300 mM NaCl, 10 mM imidazole, pH 8.0 containing 1 mM fluorescein (and 0 mM fluorescein as a control, respectively). Released protein in the supernatant was quantified after 1 day using the Bradford method (see FIG. 34):

The invention claimed is:

1. A stimulus-responsive dissolvable poly(ethylene glycol) hydrogel (PEG-hydrogel) comprising a matrix of PEG-polymers, which are modified to contain at least one multifunctional fusion protein, the multifunctional fusion protein comprising as components a single chain variable fragment (scFv fragment), a repetitive arginine-glycine-aspartic acid binding peptide (RGD-binding peptide), and at least one N- and/or C-terminal linker, wherein the at least one multifunctional fusion protein is covalently bound to the PEG polymer, and wherein the scFv fragment is the scFv fragment according to SEQ ID NO: 69 or the amino acid sequence showing at least 97.5% identity to said sequence.

2. The stimulus-responsive dissolvable PEG-hydrogel according to claim 1, wherein the PEG-polymer is a multiarm Star-PEG-polymer.

3. The stimulus-responsive dissolvable PEG-hydrogel according to claim 1, wherein the repetitive RGD-binding peptide has the formula (RGD)$_n$, wherein n is 1, 2, 3, 4, or 5, and wherein the RGD sequence is selected from the amino acid sequences according to any of SEQ ID NO: 3, 4, 6-12.

4. The stimulus-responsive dissolvable PEG-hydrogel according to claim 1, wherein the PEG-polymer is modified to allow a covalent linkage (cross-link) to the at least one multifunctional fusion protein via a thioether bond.

5. The stimulus-responsive dissolvable PEG-hydrogel according to claim 1, wherein the linker is selected from the group consisting of a thiol-containing moiety, a thiol-modified or a thiol-containing amino acid, a cysteine, an N-terminal cysteine, a homocysteine, a thiol coupled to maleimide, a vinylsulfone-moiety, peptide sequences, peptide bonds, a halotag, a SNAP-tag, a CLIP-tag, a transglutaminase reaction bond, amino acids, or chelate-forming entities NTA or polyhistidine binding to a multivalent metal ion, a lysine, a glutamine, an amine and a carboxyl group.

6. The stimulus-responsive dissolvable PEG-hydrogel according to claim 1, further containing a tag for purification, wherein the tag for purification is selected from the group consisting of a His$_6$-tag, a FLAG-tag, an HA-tag, and a MYC tag.

7. The stimulus-responsive dissolvable PEG-hydrogel according to claim 1, wherein the multifunctional fusion protein comprises as components a substrate binding peptide (SBP), a repetitive RGD-binding peptide (RGD)$_n$ a tag for purification, and at least one N- and/or C-terminal linker moiety.

8. The stimulus-responsive dissolvable PEG-hydrogel according to claim 1, wherein cells are incorporated into the stimulus-responsive dissolvable PEG-hydrogel selected from the group consisting of osteoblasts, cementoblasts, fibroblast cells derived from connective tissues, gingival-, skin or corneal fibroblasts, alone or together with periodontal ligament fibroblasts, periodontal ligament fibroblasts, keratinozytes, gingival keratinozytes, keratinocytes from the oral cavity or the upper aerodigestive tract, the skin or the ocular surface, cells of the central nervous system, neuronal cells, endothelial cells of vascular and corneal tissue, pericytes, myocytes, adipocytes, astrocytes and melanocytes.

9. The stimulus-responsive dissolvable PEG-hydrogel according to claim 1, wherein further components are incorporated into the stimulus-responsive dissolvable PEG-hydrogel selected from the group consisting of cells, proteins, polypeptides, growth factors, proteases, antibiotics, antibodies, antimicrobial polymers, and non-steroidal clinically permitted antiphlogistics, including derivates of (i) acelylsalicylacid, (ii) arylpropionacid, (iii) arylacticacid, (iv) indolaceticacid, (v) anthranilacid, and Oxicams, and selective COX-2-inhibitors.

10. The stimulus-responsive dissolvable PEG-hydrogel according to claim 1 for use as a medicament, a medical device or a medical product.

11. The stimulus-responsive dissolvable PEG-hydrogel according to claim 1 for use in the implantology, dermatology in the treatment of carcinomas in the upper aerodigestive tract, during otorhinolaryngology or ear nose throat medicine, for the treatment of wounds of the oral cavity, for the treatment of wounds in the oral cavity due to tumor diseases, during oral and maxillofacial surgery, alveolar bone augmentation coverage, for alveolar crest prevention after tooth extraction, in the treatment of periodontal defects, including periodontal ligament, for treatment of diseases in the field of ophthalmology, for the treatment of diseases of the human cornea in a patient to be treated, of the endothelial or epithelial layer of the cornea and for the treatment of Fuchs' endothelial dystrophy of the cornea, for use in burn dressings, hemostatic patches, in the treatment of lesions, in the surgical dressing, for wound treating, for soft and hard tissue regeneration, in the field of implantology, for preparing a cell implant for, integrally or partially, regenerating or reconstructing damaged or ill or removed tissues, for preparing an implant of central nervous system cells as neuronal cells for, integrally or partially, regenerating or reconstructing neuronal tissue, or as drug delivery devices or cell matrices for in vitro, in vivo and/or ex vivo applications.

12. A kit of parts, comprising the stimulus-responsive dissolvable PEG-hydrogel according to claim 1, and instructions for use.

* * * * *